(12) United States Patent
Murakami et al.

(10) Patent No.: US 6,358,267 B1
(45) Date of Patent: *Mar. 19, 2002

(54) TREATMENT TOOL FOR OPERATION

(75) Inventors: Eiji Murakami, Hachioji; Katsumi Sasaki, Tokyo; Toshihiko Hashiguchi, Sagamihara; Kenichi Kimura, Hachioji; Akira Shiga, Hidaka, all of (JP)

(73) Assignee: Olympus Optical Co., Ltd., Tokyo (JP)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/254,804

(22) PCT Filed: Jul. 16, 1998

(86) PCT No.: PCT/JP98/03208
§ 371 Date: Mar. 12, 1999
§ 102(e) Date: Mar. 12, 1999

(87) PCT Pub. No.: WO99/03405
PCT Pub. Date: Jan. 28, 1999

(30) Foreign Application Priority Data

Jul. 16, 1997 (JP) .............................................. 9-191159
Jul. 7, 1998 (JP) ........................................... 10-192017

(51) Int. Cl.[7] .............................................. A61B 17/28
(52) U.S. Cl. ..................................................... 606/205
(58) Field of Search ................................ 606/205, 206, 606/174, 1, 607, 608, 609

(56) References Cited

U.S. PATENT DOCUMENTS

| | | |
|---|---|---|
| 3,911,241 A | 10/1975 | Jarrard |
| 5,344,428 A | 9/1994 | Griffiths |
| 5,352,235 A | 10/1994 | Koros et al. |
| 5,354,312 A * | 10/1994 | Brinkerhoff et al. ......... 606/207 |
| 5,478,351 A * | 12/1995 | Meade et al. ................ 606/205 |
| 5,499,992 A * | 3/1996 | Meade et al. ................ 606/170 |
| 5,593,402 A | 1/1997 | Patrick |
| 5,849,022 A * | 12/1998 | Sakashita et al. ............ 606/174 |

FOREIGN PATENT DOCUMENTS

| | | |
|---|---|---|
| DE | 3343867 A1 | 6/1985 |
| DE | 93 17 535 U | 3/1994 |
| DE | 4307539 A1 | 9/1994 |
| DE | 94 18 094 U | 2/1995 |
| EP | 0 633 002 A1 | 1/1995 |
| EP | 0 738 501 A1 | 10/1996 |
| WO | WO 94/00059 | 1/1994 |
| WO | WO 96/04856 | 2/1996 |
| WO | WO 97/24072 | 7/1997 |

OTHER PUBLICATIONS

European Office Action dated Sep. 4, 2001 (5 pages) issued in European Application No. 98 932 558–4 (counterpart to present U.S. application).

* cited by examiner

Primary Examiner—David O. Reip
Assistant Examiner—Tan-Uyen Ho
(74) Attorney, Agent, or Firm—Frishauf, Holtz, Goodman, Langer & Chick, P.C.

(57) ABSTRACT

A treatment tool for operation comprises an insertion section (3) inserted into a living body, an operating section (5) including a fixed handle (6) removably connected to the base end side of the insertion section and a movable handle (77) adapted to operate with respect to the fixed handle, and a treatment section drive unit (2) including a treatment section operable and arranged at the forward end side of the insertion section, a drive unit (23) for driving the treatment section and a drive shaft (24) for connecting the drive unit to the operating section and transmitting the operating force of the operating section to the drive unit for operating the treatment section. An engaging section (121) is arranged at the forward end side of the fixed handle, and an engaging/disengaging member (111) is arranged at the base end of the insertion section and is adapted to engage the engaging section as required. A biasing member 108 is provided for energizing the disengaging/engaging member toward the position of engagement between the engaging/disengaging member and the engaging section.

11 Claims, 50 Drawing Sheets

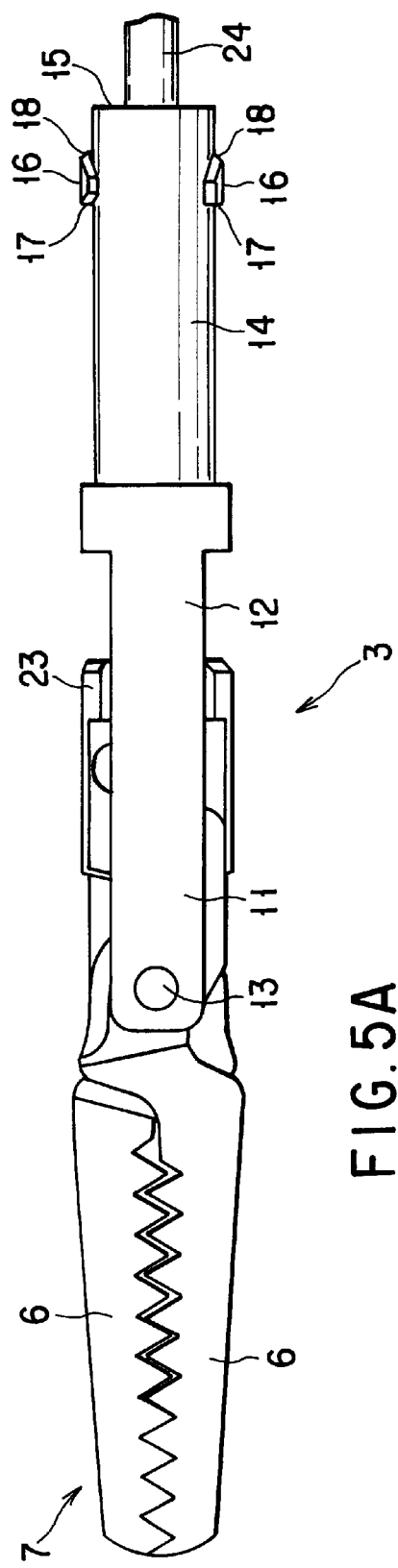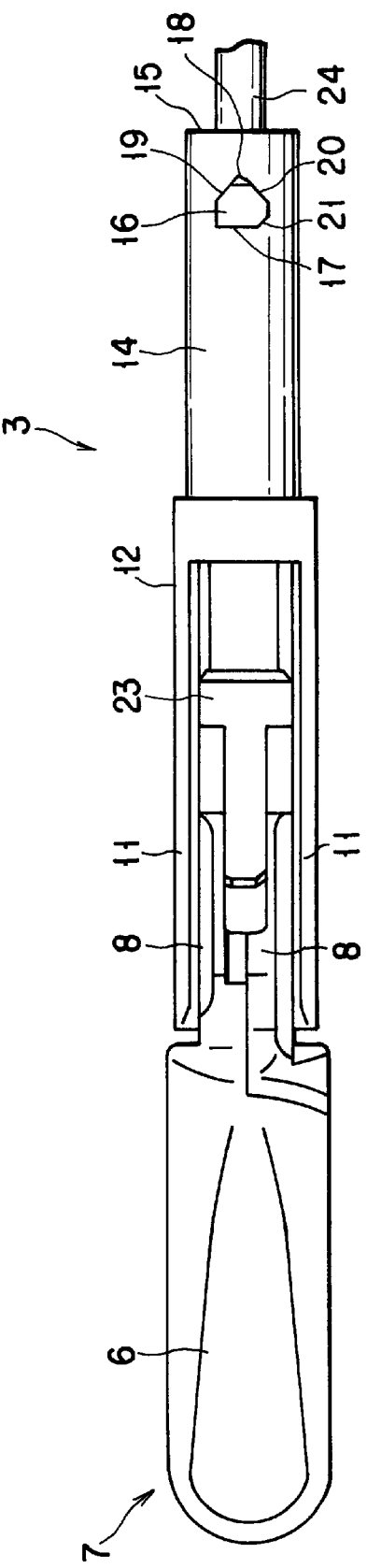
FIG.5A
FIG.5B

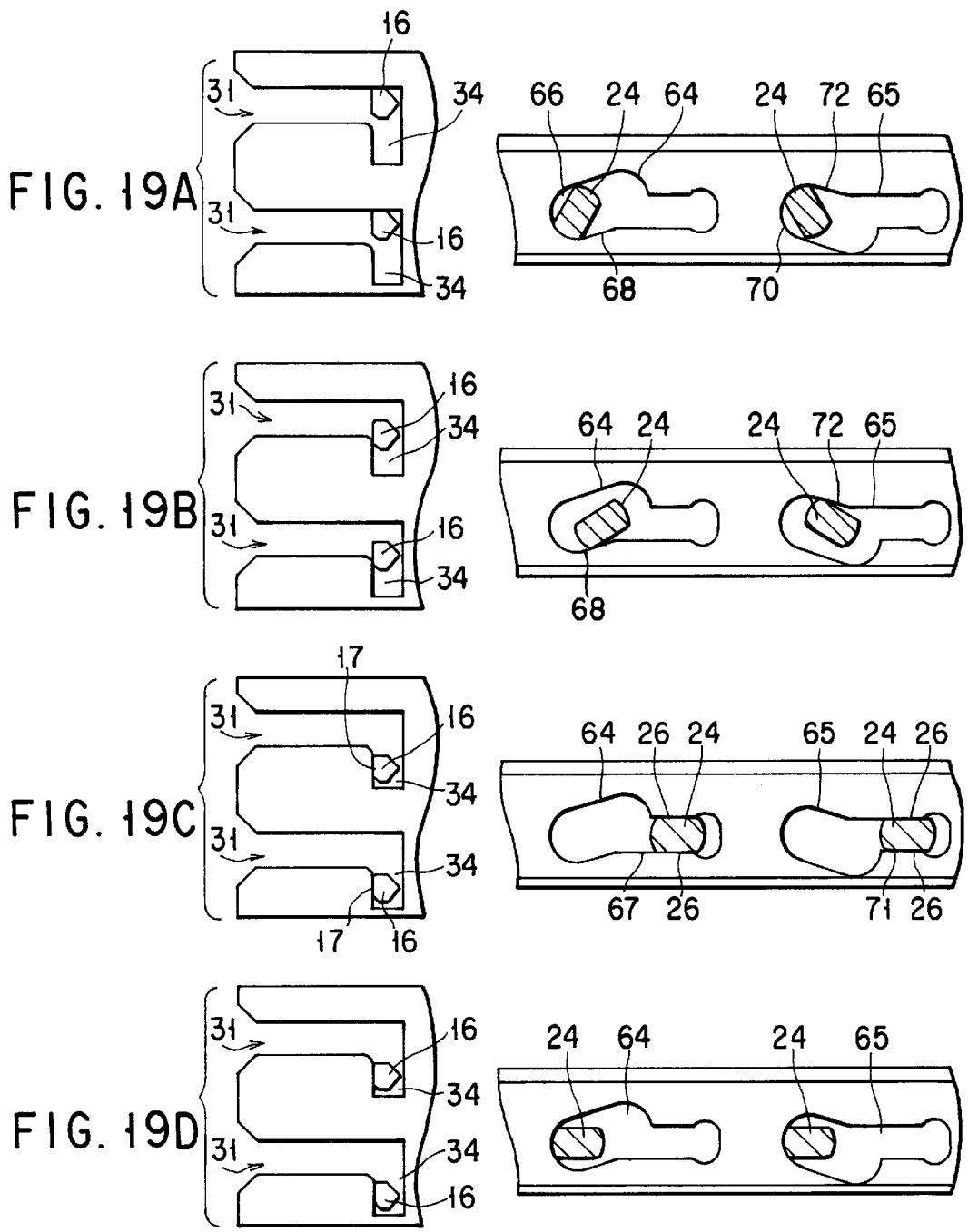

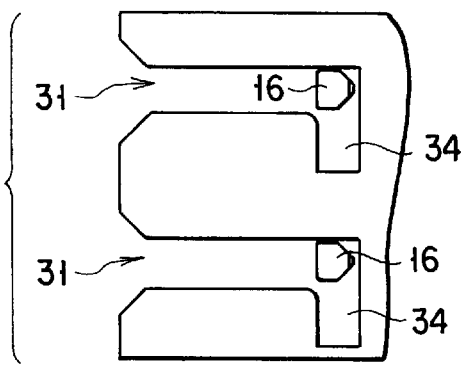
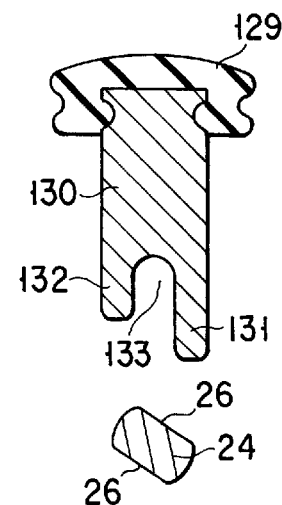
FIG. 28A
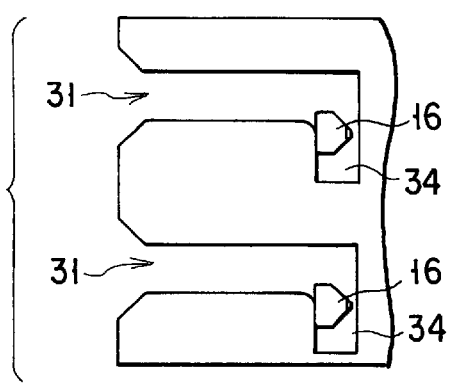
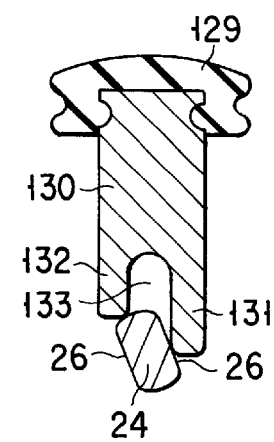
FIG. 28B
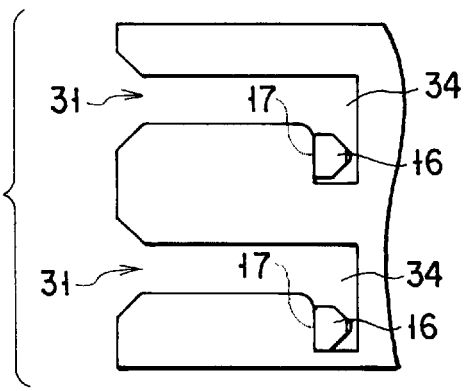
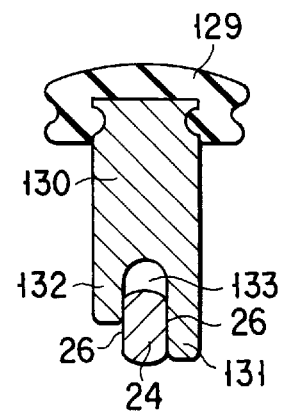
FIG. 28C

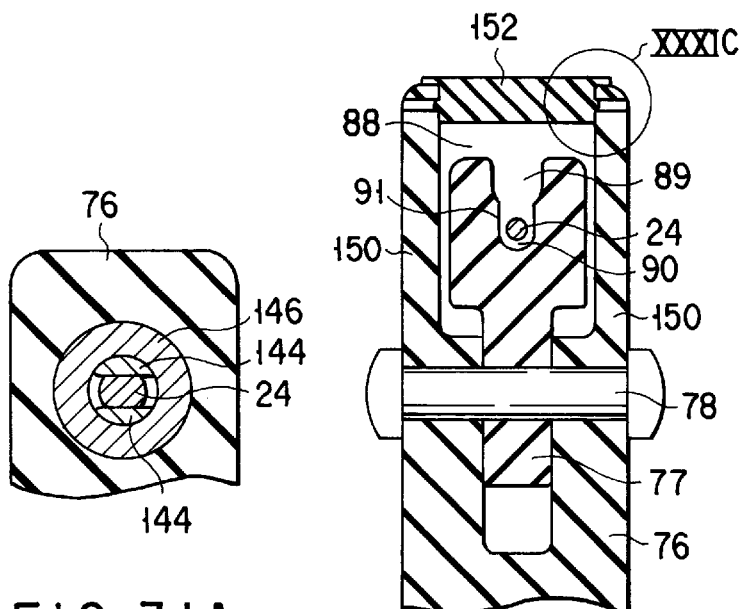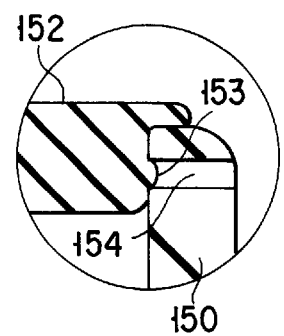
FIG. 31A
FIG. 31B
FIG. 31C
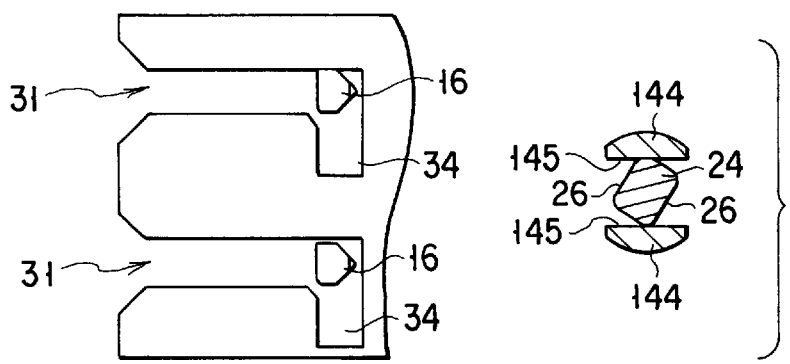
FIG. 32A
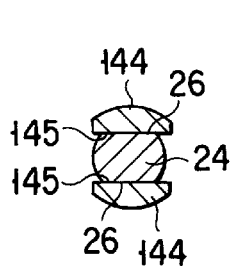
FIG. 32B

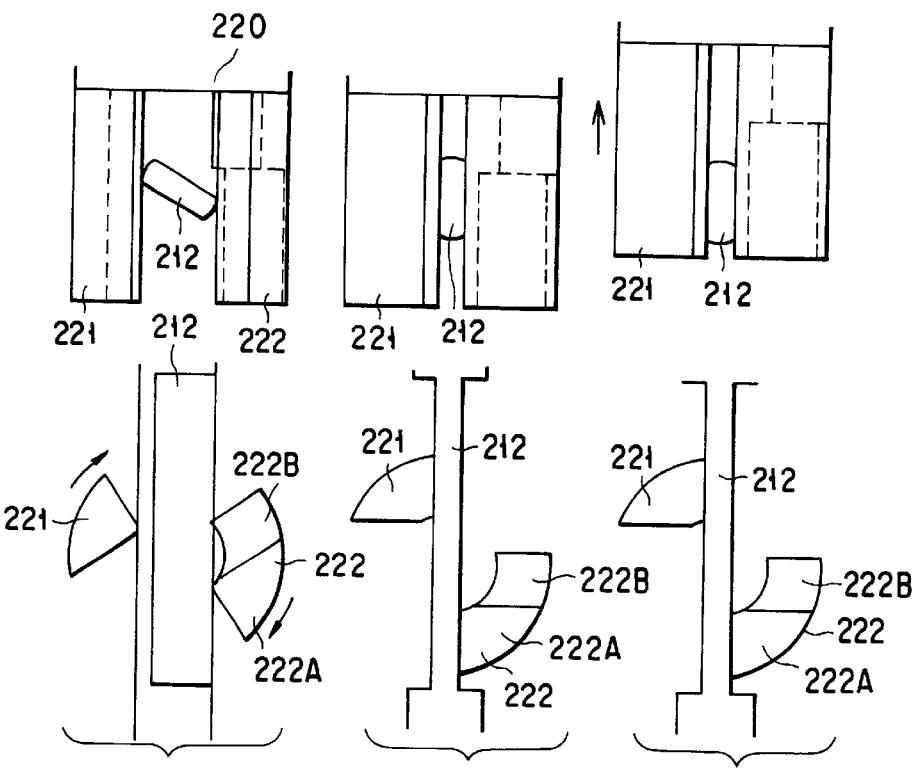
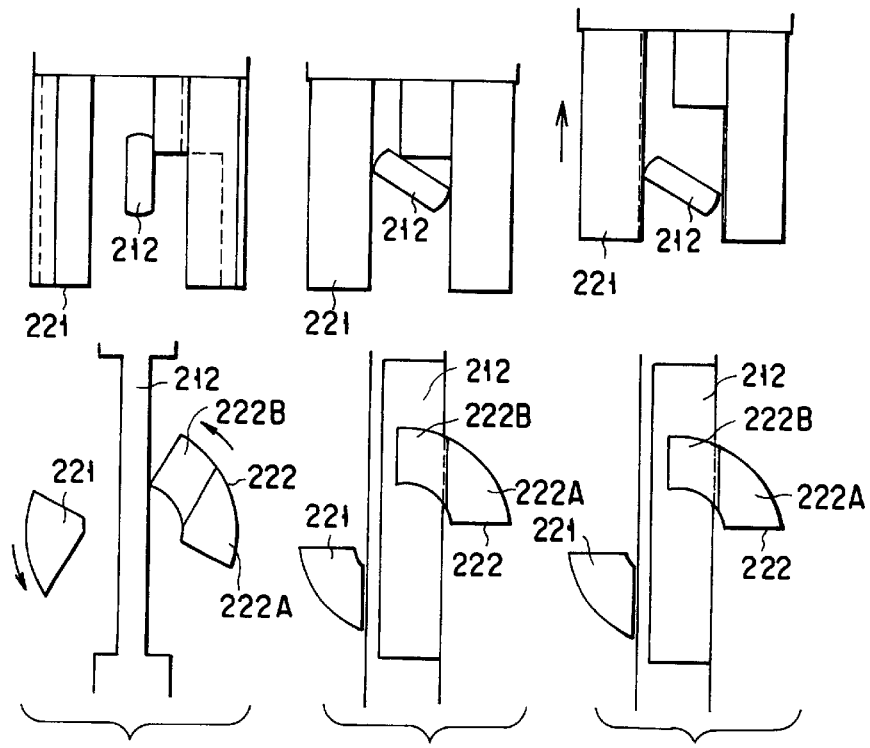
FIG.47A  FIG.47B  FIG.47C
FIG.47D  FIG.47E  FIG.47F

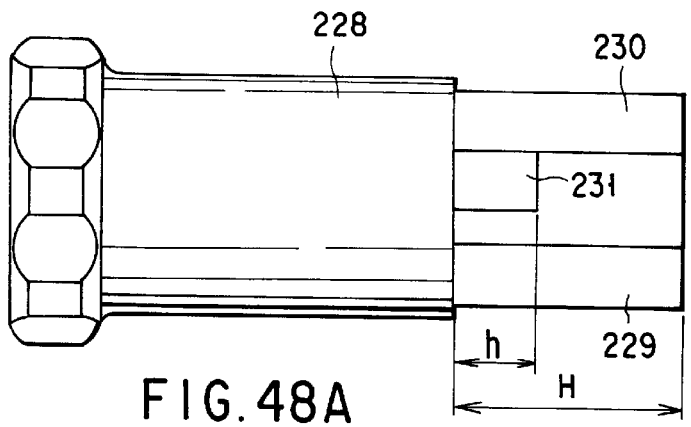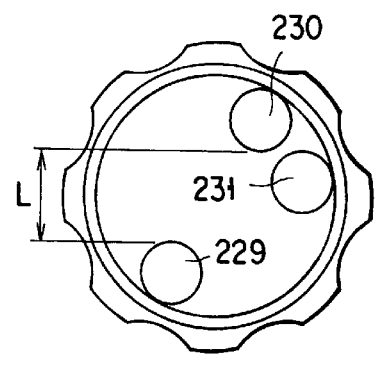
FIG. 48A  FIG. 48B
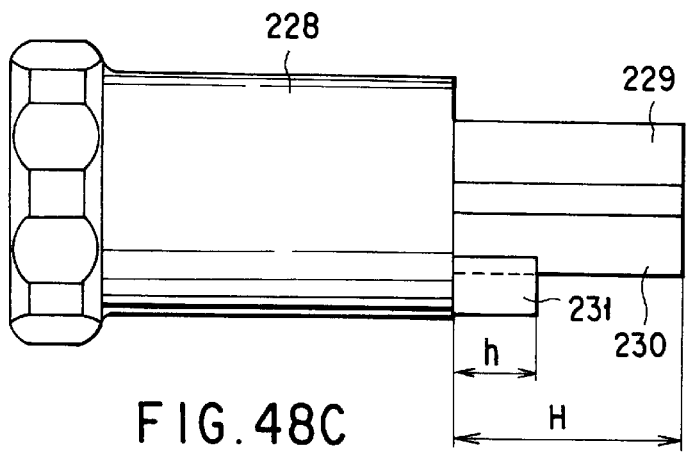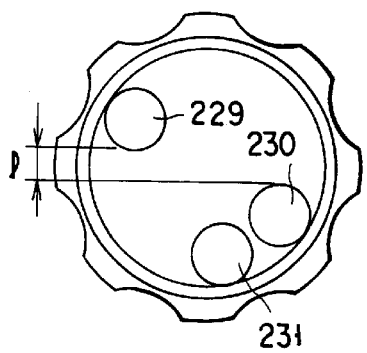
FIG. 48C  FIG. 48D (I) (II) (III) (IV)

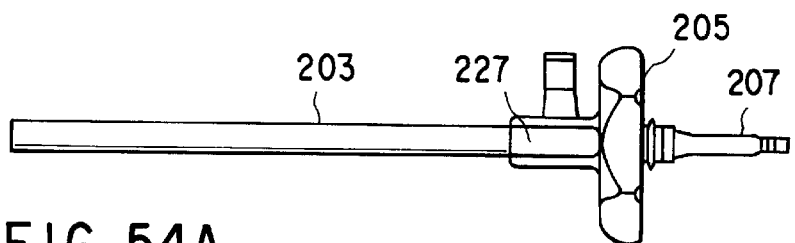
FIG. 54A
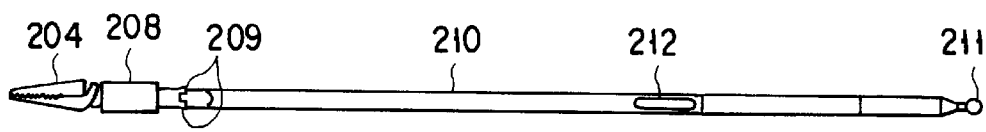
FIG. 54B
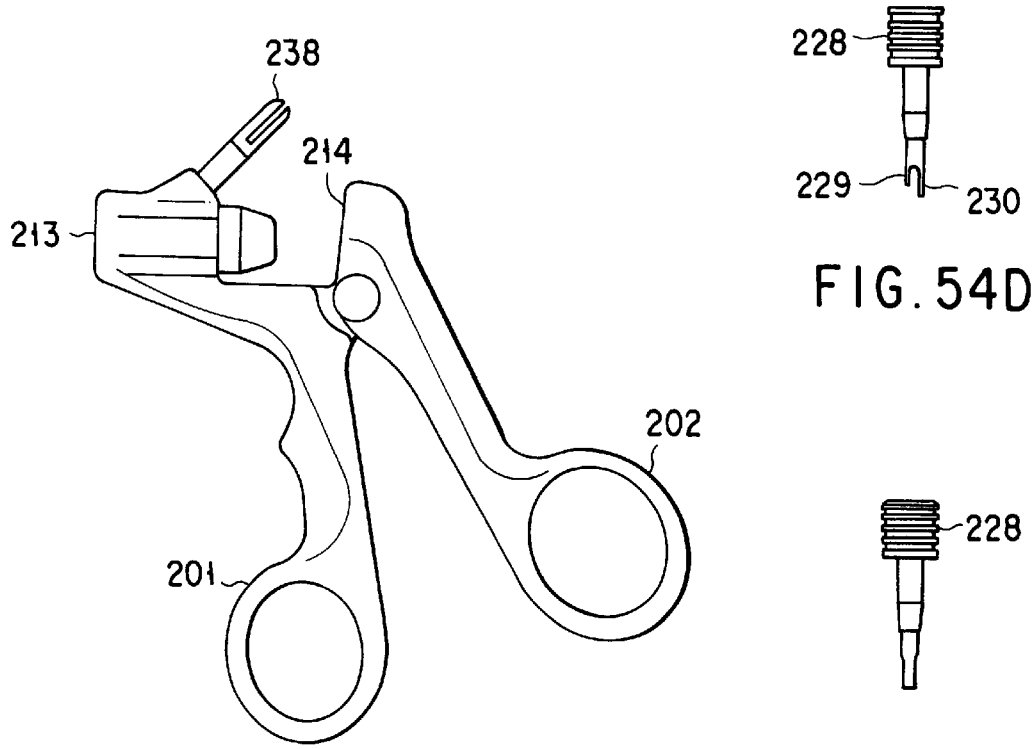
FIG. 54C
FIG. 54D
FIG. 54E

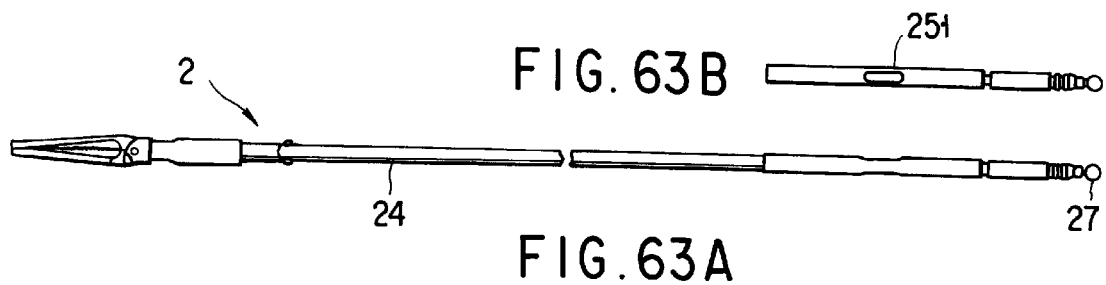
FIG. 63B
FIG. 63A
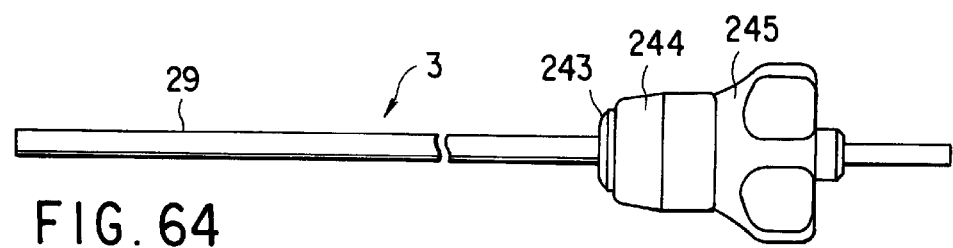
FIG. 64
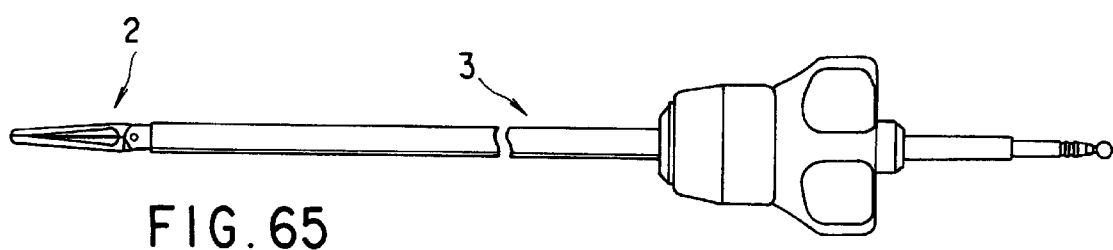
FIG. 65
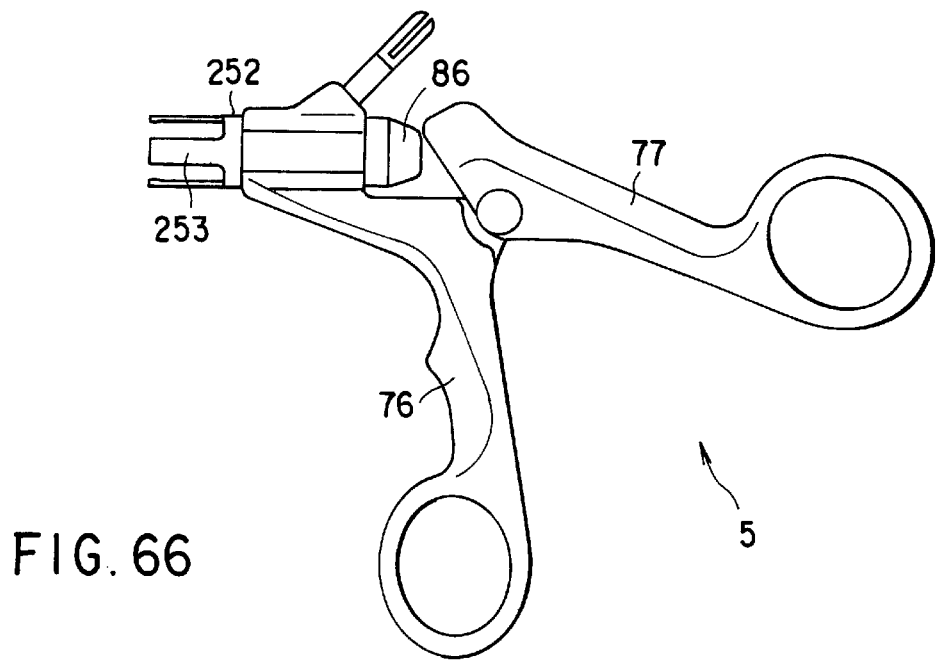
FIG. 66

US 6,358,267 B1

TREATMENT TOOL FOR OPERATION

TECHNICAL FIELD

The present invention relates to a treatment tool for operation inserted into a body cavity for treating the tissue of an affected part.

BACKGROUND ART

The conventional treatment tool for operation such as disclosed in DE4307539A1 or DE4323093A1 comprises three component parts including an operating section, an insertion section and a treatment section drive unit, and is so configured as to be separated into the above-mentioned three component parts to permit only damaged parts to be partially replaced and the interior of the insertion section to be easily washed. In this case, the insertion section and the operating section are removably coupled to each other by a screw-type coupling mechanism.

With the conventional treatment tool for operation, however, the use of the screw-type coupling mechanism for the connector of the insertion section and the operating section makes the mounting and demounting a troublesome job, and the job of mounting and demounting consumes considerable time. Also, the dust and dirt, body fluid and blood generated during an operation often stay on and contaminate the thread tops and roots of the screw-type coupling mechanism. Further, the thread tops and roots of the screw-type coupling mechanism are hard to wash. The screw-type coupling mechanism, therefore, is not desirably used with such equipment as medical ones which require a high degree of cleanliness.

This invention has been developed in view of the above-mentioned situation, and the object thereof is to provide a treatment tool for operation suitable as a medical equipment requiring a high degree of cleanliness which can be disassembled and assembled easily within a short time.

SUMMARY OF THE INVENTION

In order to achieve the above-mentioned object, according to this invention, there is provided a treatment tool for operation comprising: an insertion section inserted into a living body; an operating section including a fixed handle connected removably to the base end of the insertion section and a movable handle operable with respect to the fixed handle; a treatment section drive unit combined with the insertion section, and including a treatment section operable and arranged at the forward end of the insertion section, drive means for driving the treatment section, and a drive shaft for connecting the drive means to the operating section and transmitting the operating force of the operating section to the drive means for actuating the treatment section; an engaging section arranged at the forward end of the fixed handle; an engaging/disengaging member arranged at the base end of the insertion section for engaging the engaging section removably; and biasing means for energizing the engaging/disengaging member toward the position of engagement with the engaging section.

With this configuration, the treatment section drive unit and the insertion section can be disassembled and assembled easily within a short time by rotating the rotary engaging means with respect to the insertion section.

BRIEF DESCRIPTION OF DRAWINGS

FIG. 5A is a side view of the forward end of the treatment section drive unit;

FIG. 5B is a plan view of the treatment section drive unit;

FIGS. 19A to 19D are diagrams showing relative positions of protrusions and engaging grooves and relative positions of a cylindrical cam slot and a drive shaft for the disassembly/assembly work of the treatment tool for operation of FIG. 1;

FIGS. 28A to 28C are diagrams showing relative positions between protrusions and engaging grooves and between a drive shaft and a fork member for the disassembly and assembly work of the treatment tool for operation of FIG. 24;

FIG. 31A is a sectional view taken in line O—O in FIG. 29;

FIG. 31B is a sectional view taken in line P—P in FIG. 29;

FIG. 31C is an enlarged sectional view of a part XXXIC shown in FIG. 31B;

FIGS. 32A and 32B are diagrams showing relative positions of protrusions and the engaging grooves for the disassembly and assembly work of the treatment tool for operation of FIG. 29 and a sectional view taken in line Q—Q in FIG. 30 corresponding to the relative positions;

FIGS. 47A to 47F are diagrams showing the operation of the button and the rotary engaging member of the operating shaft of the treatment tool for operation of FIG. 42;

FIGS. 48A and 48C are side views of the button of a treatment tool for operation according to an eighth embodiment of the invention;

FIGS. 48B and 48D are front views of the button of a treatment tool for operation according to an eighth embodiment of the invention;

FIG. 54A is a side view of the sheath unit constituting the treatment tool for operation of FIG. 53;

FIG. 54B is a side view of the treatment section drive unit constituting the treatment tool for operation of FIG. 53;

FIG. 54C is a side view of the operating section constituting the treatment tool for operation of FIG. 53;

FIGS. 54D and 54E are side views of a rotary fixing member constituting the treatment tool for operation of FIG. 53;

FIGS. 63A and 63B are side views of the treatment section drive unit;

FIG. 64 is a side view of the insertion section;

FIG. 65 is a side view of an assembly in which the treatment section drive unit is assembled in the insertion section;

FIG. 66 is a side view of the operating section;

DETAILED DESCRIPTION

Figure 1:
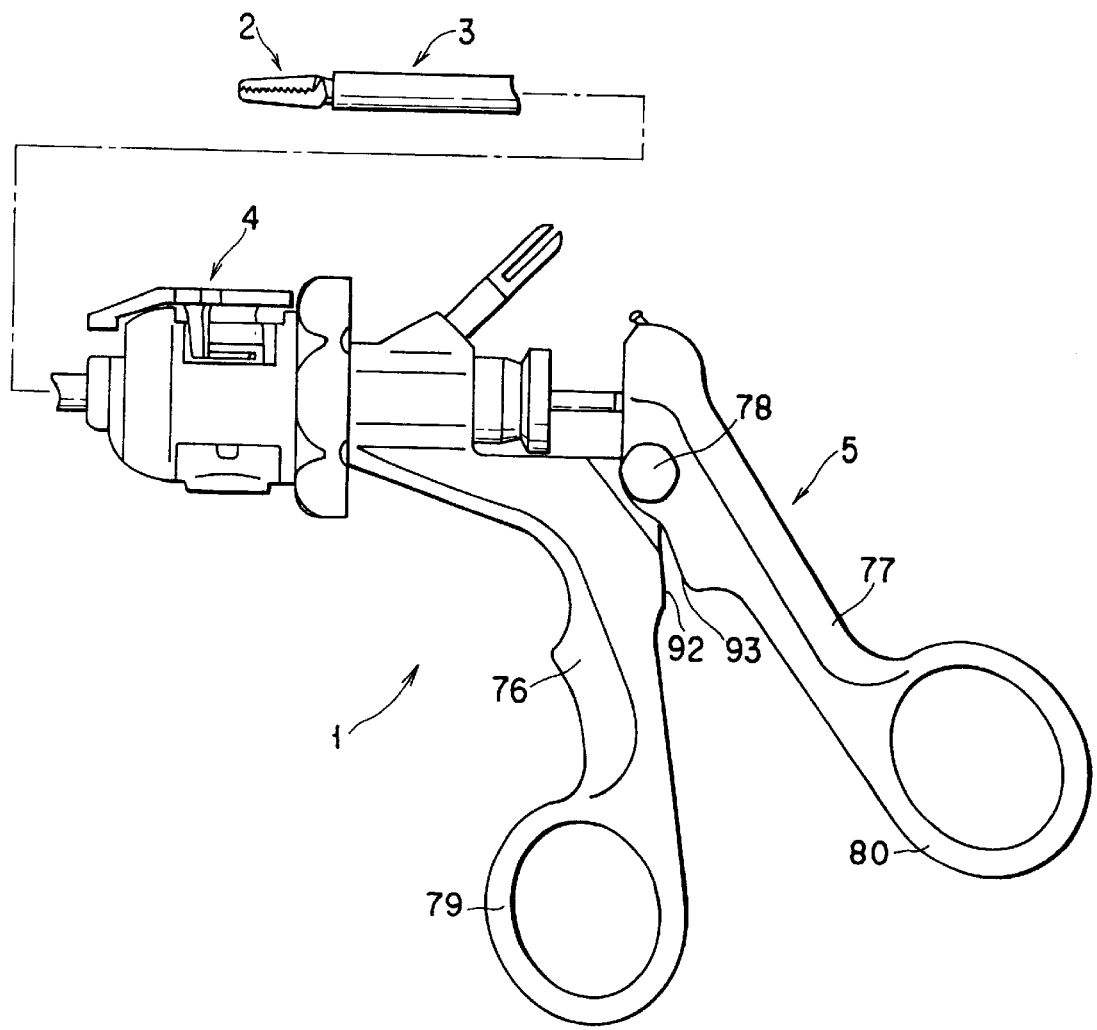
FIG. 1 is a side view of a treatment tool for operation according to a first embodiment of the present invention.
Figure 2A:
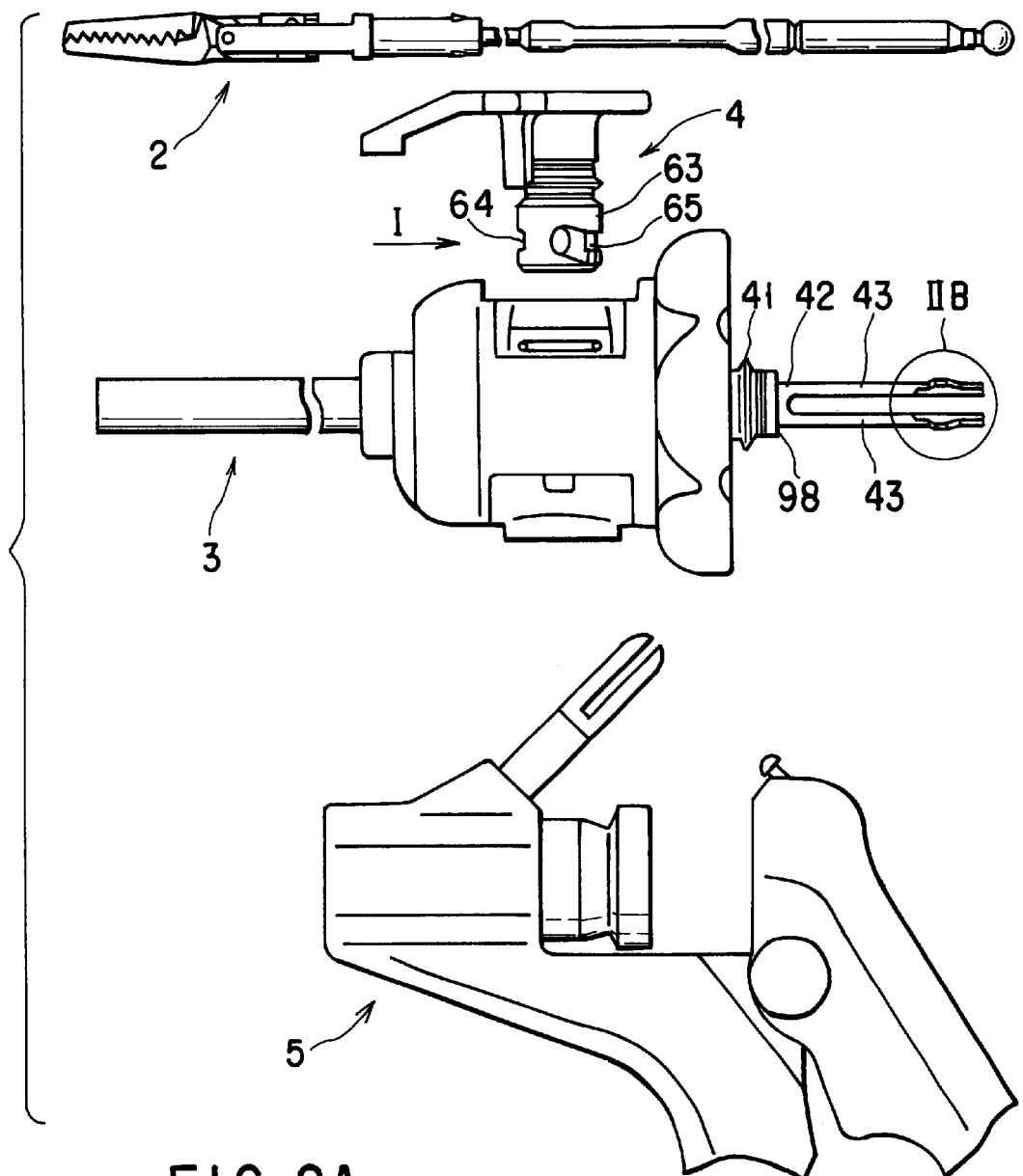
FIG. 2A is a side view showing the state of the treatment tool for operation of FIG. 1 disassembled into the treatment section drive unit, the insertion section, the rotary engaging member and the operating section.
Figure 2B:
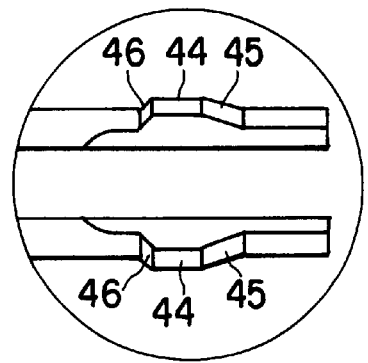
FIG. 2B is an enlarged view of a part IIB shown in FIG. 2A.

FIGS. 1 to 19D show a first embodiment of the invention. A treatment tool for operation 1 according to this embodiment can be separated, as shown in FIG. 1, into four component parts, i.e. a treatment section drive unit 2, an insertion section 3, a rotary engaging member 4 constituting rotary engaging means, and an operating section 5. As shown in FIGS. 2A and 2B, the treatment tool for operation 1 can be separated into the four component parts 2, 3, 4, 5.

Figure 3A:
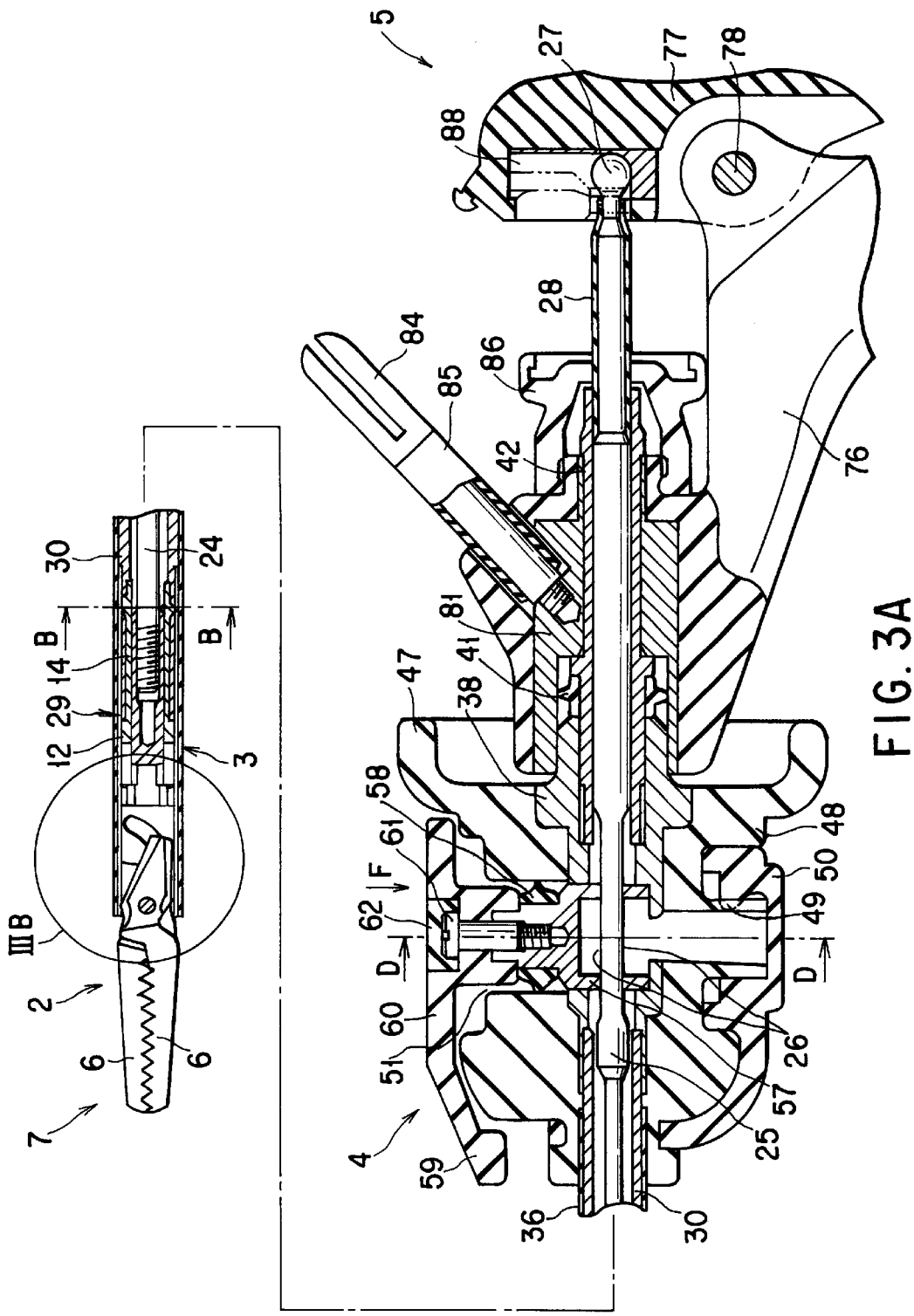
FIG. 3A is a side sectional view of the treatment tool for operation of FIG. 1.
Figure 3B:
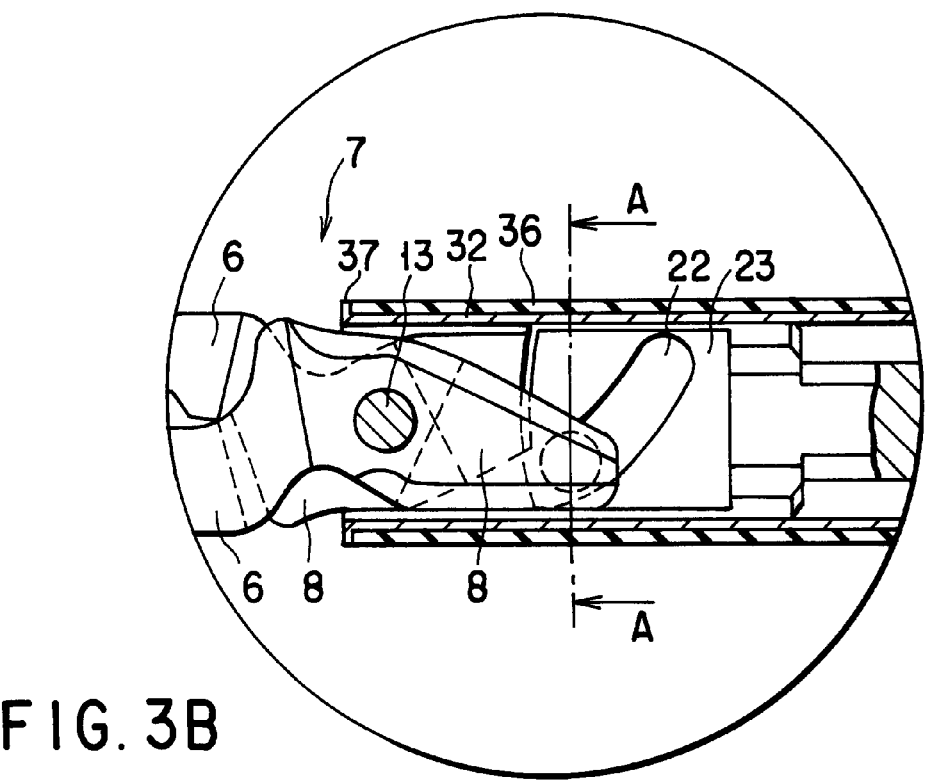
FIG. 3B is an enlarged view of a part IIIB shown in FIG. 3A.
Figure 4:
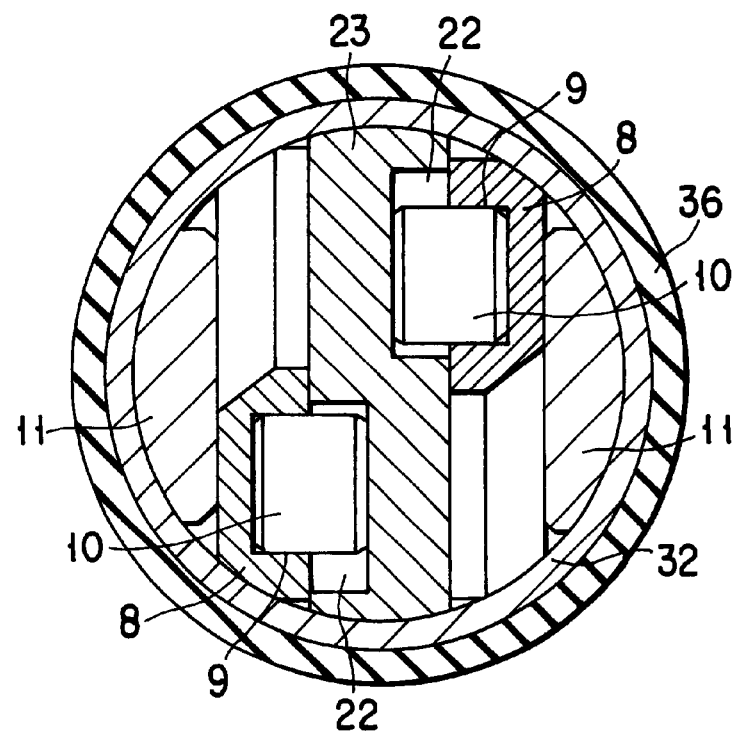
FIG. 4 is a sectional view taken in line A—A in FIG. 3B.

As shown in FIGS. 3A and 3B, a treatment section 7 is arranged at the forward end side of the treatment section drive unit 2. This treatment section 7 includes a pair of openable holding members (treatment members) 6, 6. The base end side of each holding member 6 is formed integrally with a link arm 8. As shown in FIG. 4 (sectional view taken in line A—A in FIG. 3B), the base end of the link arm 8 is formed with a fitting hole 9, in which a slide pin 10 is rotatably provided.

As shown in FIGS. 3A, 3B and 4, the base end of the holding members 6, 6 is provided with a support member 12 having two support arms 11, 11 located in such a position as to sandwich the link arms 8, 8 from the two sides. In this case, the holding members 6, 6 (link arms 8, 8) are rotatably coupled to the support member 12 through a pin 13 fixed on the support arms 11, 11.

As shown in detail in FIGS. 5A and 5B, the base end side of the support member 12 is formed with a cylindrical connector 14. The base end of the connector 14 is formed with a butt surface 15. The outer peripheral surface of the base end side of the connector 14 is formed with two protrusions 16, 16 symmetric about the center axis of the connector 14. The protrusions 16, 16 each include a butt surface 17 located at the forward end thereof, a slope surface 18 located at the base end side, slope surfaces 19, 20 located at the sides of the base end, and a slope surface 21 located at the sides of the forward end thereof.

As shown in FIGS. 3A to 5B, the base end side of the holding members 6, 6 is provided with a drive member (drive means) 23 sandwiched between the link arms 8, 8. This drive member 23 has cam slots 22, 22 which slide pins 10, 10 slidably engage. Also, the drive member 23 has the base end side thereof inserted through the inner hole of the support member 12, and adapted to be movable longitudinally by being supported on the support member 12. By the way, the outer surface of the slide pins 10, 10, the fitting holes 9, 9 and the cam slots 22, 22 may be coated with a material of a superior sliding characteristic such as fluoric resin.

The drive member 23 is provided integrally with a drive shaft 24. The drive shaft 24 extends from the base end of the drive member 23 and has a large-diameter portion 25 at the base end thereof (see FIGS. 3A, 5A and 5B). The large-diameter portion 25 is formed with two mutually parallel planes 26, 26. Also, the base end of the drive shaft 24 is provided with a ball-shaped coupler 27. Further, the outer periphery of the base end of the drive shaft 24 is covered with a tube 28 made of an electrically insulating material, as shown in FIGS. 3A and 3B.

Figure 6:
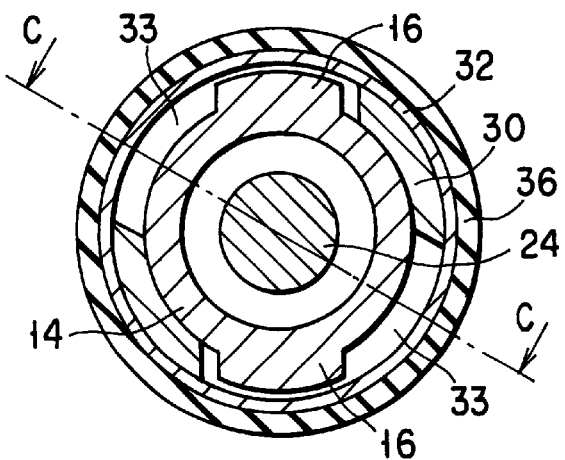
FIG. 6 is a sectional view taken in line B—B in FIG. 3A.

The treatment section drive unit 2 having the above-mentioned configuration is inserted into a sheath 29 of the insertion section 3 which in turn is inserted into a living body. The sheath 29 is configured by covering a tube 36 made of an electrically insulating material on the outer periphery of a pipe (connector) 30 and a forward end pipe 32. As shown in FIG. 6 (sectional view taken in line B—B in FIG. 3A), FIG. 7 (sectional view taken in line C—C in FIG. 6) and FIG. 8, the forward end of the pipe 30 is provided substantially L-shaped engaging grooves 31, 31 including engaging sections 34, 34 and insertion guides 33, 33 engageable with the protrusions 16, 16 on the connector 14, which grooves are arranged symmetrically about the center axis of the pipe 30. As shown in detail in FIG. 8, each engaging groove 31 is formed with slope surfaces 31a, 31b at the forward end thereof, and a slope surface 31c at the base end thereof.

Figure 7:
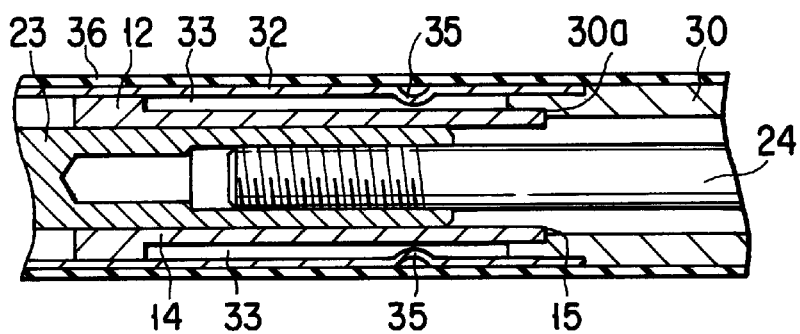
FIG. 7 is a sectional view taken in line C—C in FIG. 6.
Figure 8:
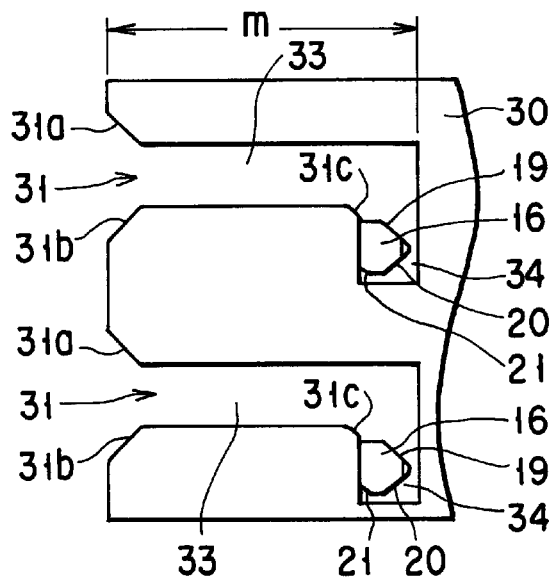
FIG. 8 is a development of a pipe at the forward end of the insertion section of the treatment tool for operation shown in FIG. 1.

As shown in FIG. 7, the inner peripheral surface at the forward end side of the pipe 30 is formed with an annular butt surface 30a adapted to come into contact with the butt surface 15 of the connector 14. Also, the portion of the forward end pipe 32 covering the forward end of the pipe 30 is formed with hemispherical inner protrusions 35, 35 protruded inward toward the insertion guides 33, 33 of the engaging groove 31. These inner protrusions 35, 35 are protruded inward to such an extent as to interfere with the protrusions 16, 16 of the connector 14 inserted in engagement into the insertion guides 33, 33. When interfering with the protrusions 16, 16, the inner protrusions 35, 35 are deformed elastically outward by the protrusions 16, 16 and thus allow a further insertion of the protrusions 16, 16. By the way, as shown in FIGS. 3A and 3B, the forward end of the forward end pipe 32 is formed with a large-diameter section 37 for preventing forward displacement of the tube 36.

Figure 9:
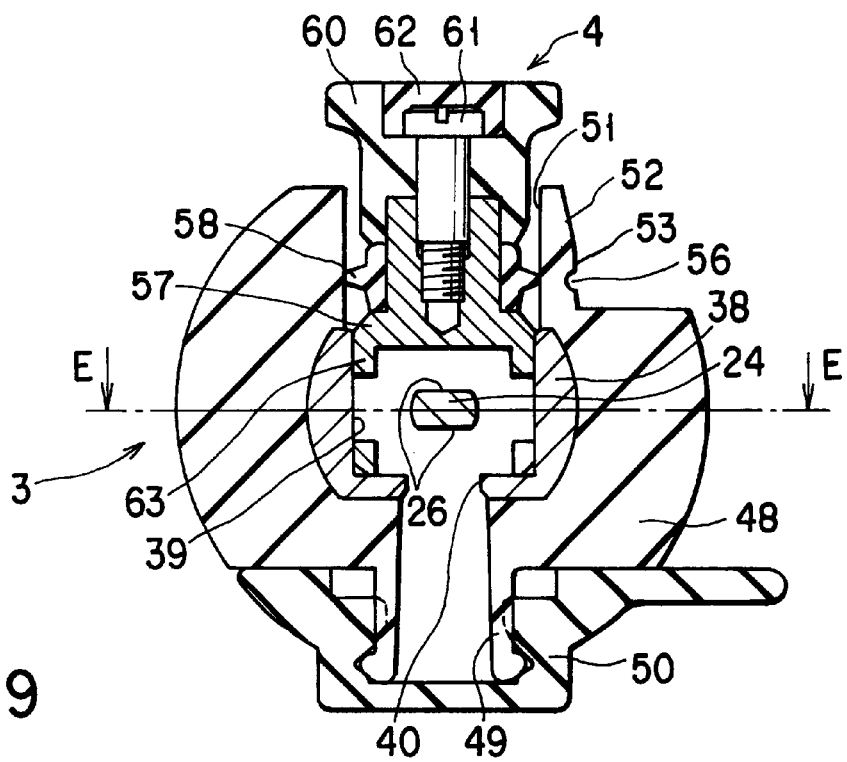
FIG. 9 is a sectional view taken in line D—D in FIG. 3A.
Figure 10:
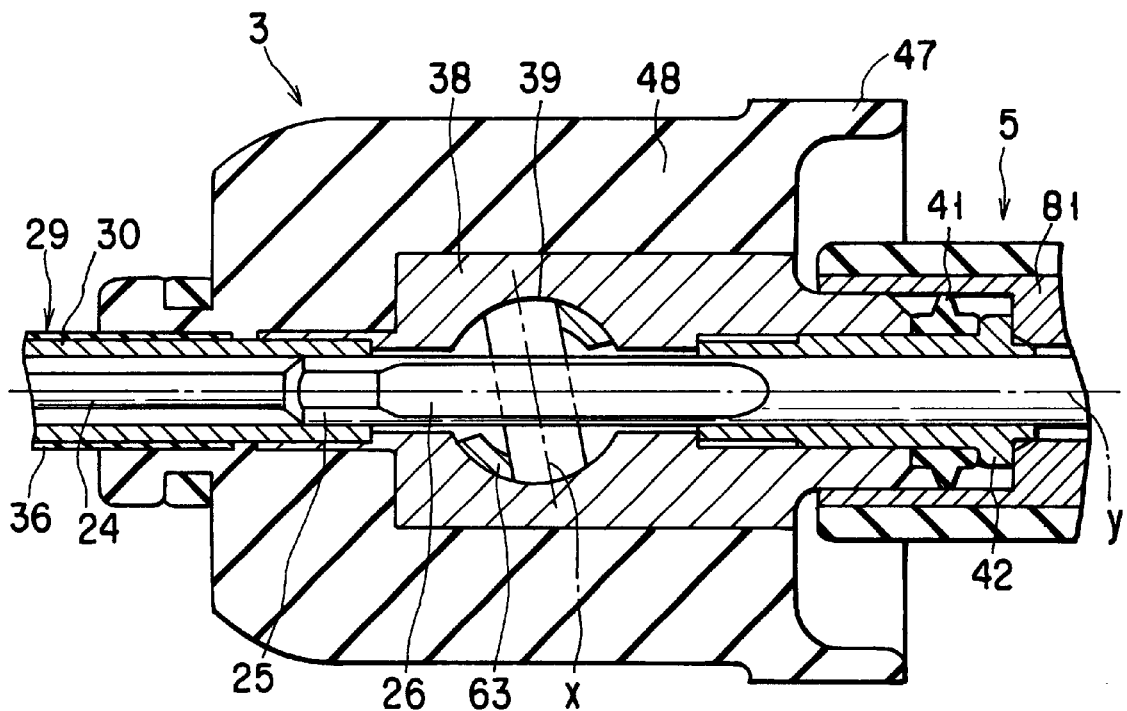
FIG. 10 is a sectional view taken in line E—E in FIG. 9.
Figure 11:
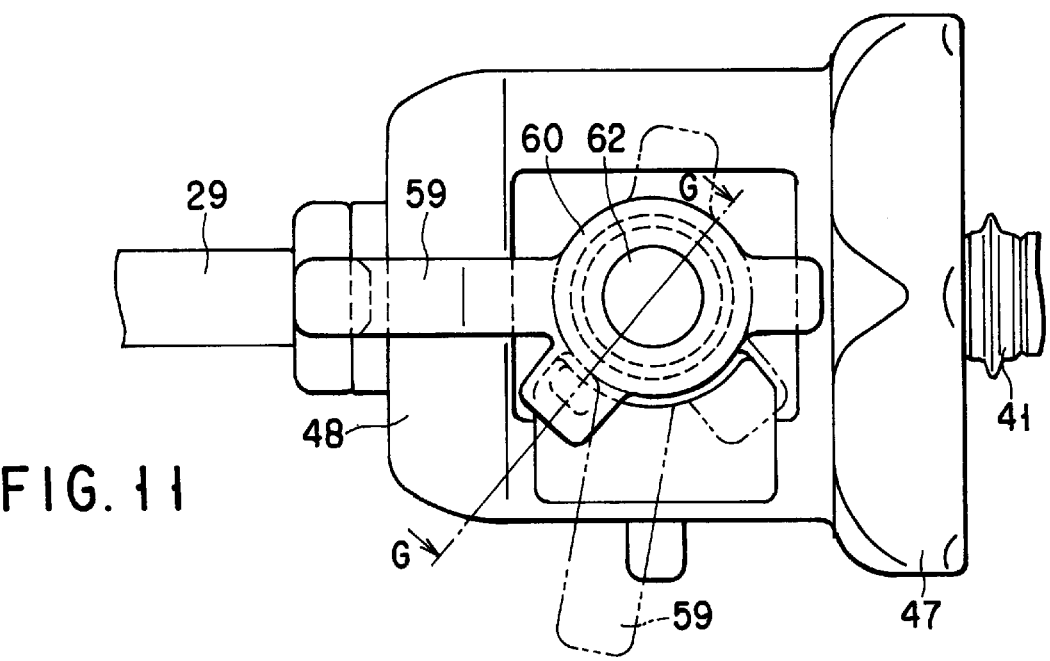
FIG. 11 is a view taken along the direction of arrow F in FIG. 3A.

As shown in FIGS. 3A and 3B, the base end of the pipe 30 is provided integrally with a holding member 38 for holding the rotary engaging member 4. As shown in FIG. 9 (sectional view taken in line D—D in FIG. 3A), the holding member 38 is formed with two holes 39, 40. These holes 39, 40 extend in the direction perpendicular to the center axis of the sheath 29. The base end side of the holding member 38 is provided integrally with a snap fit member 42 connected removably to the operating section 5. By the way, as shown in FIGS. 3A and 3B and FIG. 10 (sectional view taken in line E—E in FIG. 9), an annular rubber packing 41 is mounted on the outer periphery at the forward end of the snap fit member 42.

As shown in FIGS. 2A and 2B, the forward end side of the snap fit member 42 is formed with a butt surface 98. Also, the snap fit member 42 is formed with two snap fit arms 43, 43 of cantilever type. A protrusion 44 is formed on the outer periphery at the forward end of each snap fit arm 43. This protrusion 44 is formed with a slope surface 45 at the forward end thereof and a slope surface 46 at the base end thereof.

Figure 12:
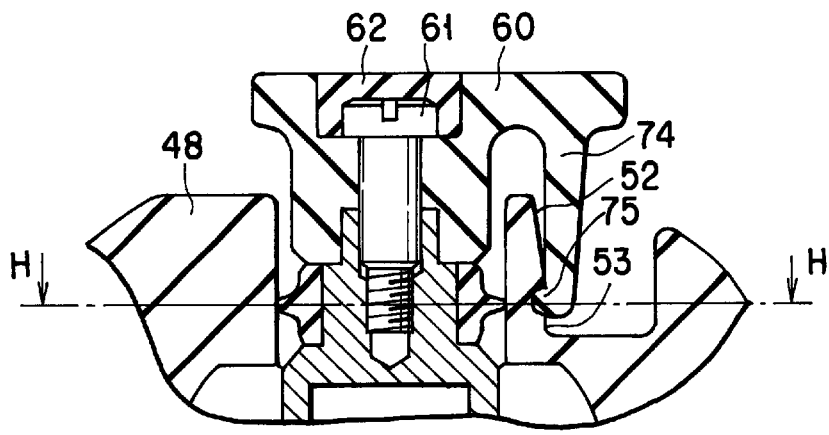
FIG. 12 is a sectional view taken in line G—G in FIG. 11.

As shown in FIGS. 3A, 3B, 9, 10 and 11 (view in the direction F along arrow in FIG. 3A), the outer periphery of the holding member 38 is provided integrally with a knob 48 made of an electrically insulating material. The knob 48 has a rotary operating section 47 for rotating the insertion section 3 with respect to the operating section 5. The knob 48 also has a washing stem 49 connected to the hole 40 of the holding member 38, and a rubber plug 50 is mounted on the washing stem 49 for openably closing the same. Also, the insertion hole of the knob 48 into which the rotary engaging member 4 is inserted is formed with a hole 51 communicating to the hole 39 of the holding member 38. Also, the outer periphery of the insertion hole section of the knob 48 is formed, as shown in FIG. 9 and FIG. 12 (sectional view taken in line G—G in FIG. 11), with a slope surface 52 extending in a direction at a predetermined angle to the center axis of the hole 51 and a cylindrical surface 53 extending along the center axis of the hole 51. As shown in detail in FIG. 13 (sectional view taken in line H—H in FIG. 12), the cylindrical surface 53 is formed with an engaging groove (engaging/disengaging portion) 56 having protrusions 54, 55 at two positions thereof.

As shown in FIGS. 3A, 3B, 9, 11, 12, the rotary engaging member 4 removably mounted on the knob 48 includes an engaging member 57 inserted into the hole 39 of the holding member 38 and held rotatably, an annular rubber packing 58 in contact with the inner surface of the hole 51 of the knob 48, and a lever 60 made of an electrically insulating material having a lever member 59 for rotating the engaging member 57. The lever 60 is fixed on the engaging member 57 by a screw 61. The upper portion of the screw 61 is covered with a cover 62 made of an electrically insulating material. The forward end of the engaging member 57 is formed with a cylindrical section 63. The cylindrical section 63 is formed with a pair of cam slots 64, 65 in opposed relation to each other as shown in FIGS. 2A and 2B.

Figure 14:
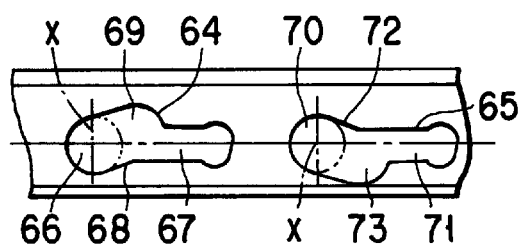
FIG. 14 is a diagram showing the development of a cylindrical section as viewed along the direction I in FIG. 2A.

As shown in FIG. 14 (development of the cylindrical portion 63 as viewed from direction I in FIG. 2A), the cam slot 64 includes a circular hole 66 having an inner diameter larger than the outer diameter of the drive shaft 24, a slope section 68 extending diagonally upward from the hole 66 for rotating the drive shaft 24, parallel grooves 67 extending in the direction perpendicular to the center axis of the cylindrical portion 63 from the slope section 68 and adapted to engage two parallel planes 26, 26 of the drive shaft 24, and a relief 69 for avoiding the interference with the drive shaft 24. In this case, the hole 66 is formed in such a manner that the center axis thereof coincides with the center axis of the sheath 29 with the rotation of the cylindrical portion 63. By the way, the cam slot 65, like the cam slot 64, includes a hole 70, a parallel groove 71, a slope section 72 and a relief 73.

As shown in FIG. 12, an elastically deformable arm 74 extends downward from the lever 60. The forward end of the arm 74 is formed with a hemispherical portion (engaging/disengaging portion) 75 adapted to engage the engaging slot 56 in the cylindrical surface 53 of the knob 48.

Figure 15:
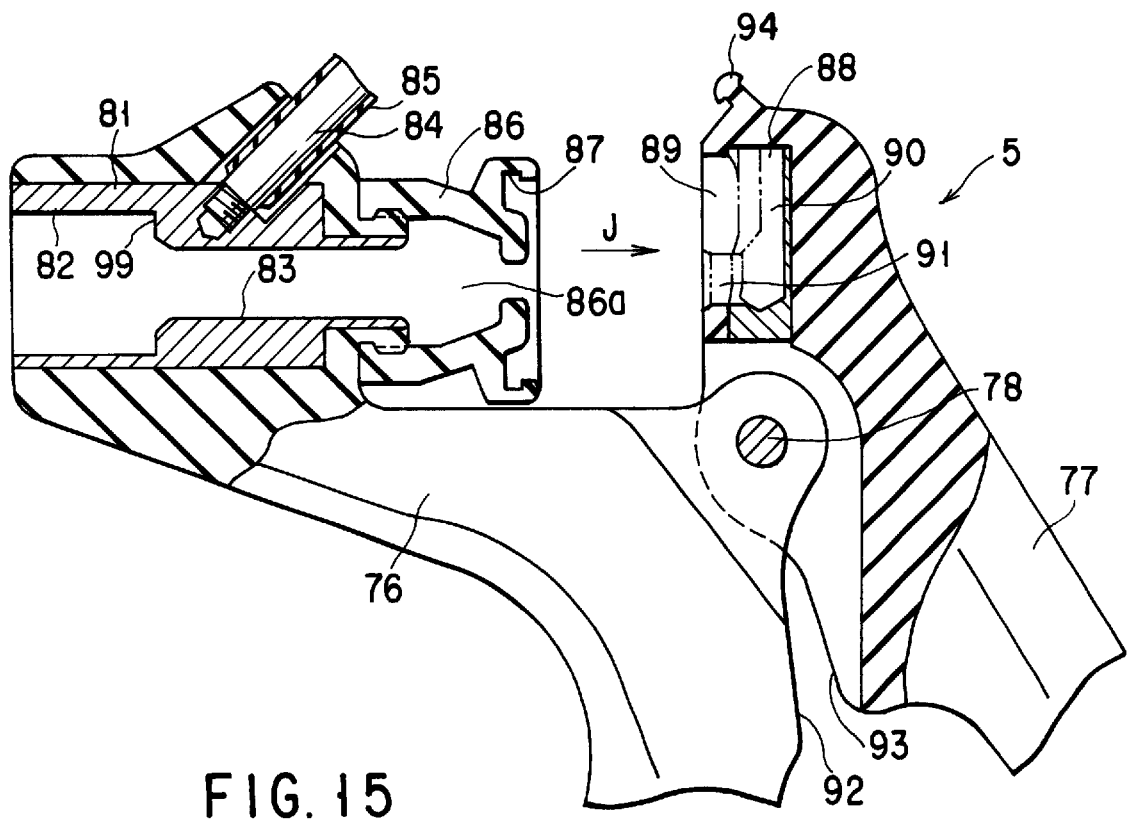
FIG. 15 is a partial sectional view of the operating section of the treatment tool for operation of FIG. 1.

As shown in FIG. 15, the operating section 5 removably mounted on the treatment section drive unit 2 and the insertion section 3 includes a substantially L-shaped fixed handle 76 and a movable handle 77 made of an electrically insulating material. The movable handle 77 is rotatably coupled to the fixed handle 76 through a fulcrum pin (supporting point member) 78 arranged in the L-shaped curved portion of the fixed handle 76. An end of the fixed handle 76 is formed with a ring 79 for inserting a finger, and an end of the movable handle 77 is formed with a ring 80 for finger insertion. Also, a tubular insertion section connector 81 is arranged above the movable handle 76. The insertion section connector 81 has formed therein a large-diameter section 82 for accommodating the rubber packing 41 of the insertion section 3, and a small-diameter section 83 for accommodating the snap fit member 42 of the insertion section 3. By the way, a butt surface 99 is formed between the large-diameter section 82 and the small-diameter section 83.

The insertion section connector 81 has fixed thereon an electrode pin 84 for supplying a high-frequency current, and a cover 85 made of an electrically insulating material for covering the electrode pin 84. A rubber cap 86 is removably arranged at the upper portion of the fixed handle 76. The rubber cap 86 is formed with a hole 86a for inserting the drive shaft 24 of the treatment section drive unit 2 and an annular groove 87.

Figure 16:
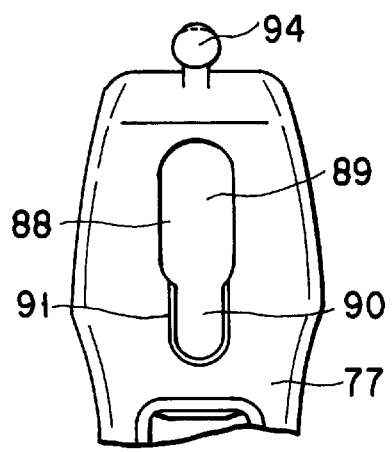
FIG. 16 is a view taken along the direction of arrow J in FIG. 15.
Figure 17:
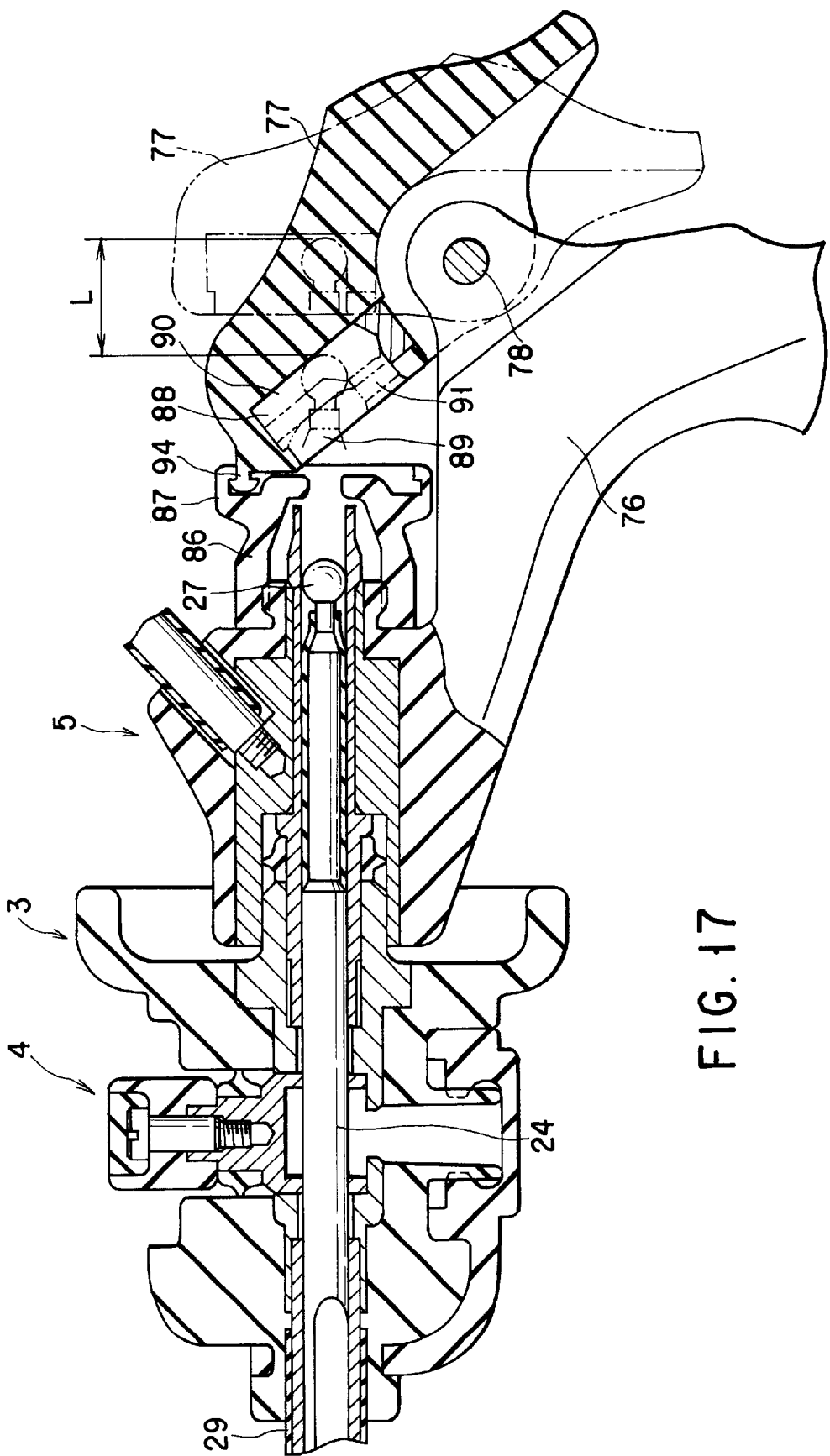
FIG. 17 is a sectional view showing the state of the treatment section drive unit of the treatment tool for operation of FIG. 1 assembled in the correct mounting positions of the insertion section and the operating section.

As shown in FIGS. 15 and 16 (diagram as viewed in the direction of arrow J in FIG. 15), a connection groove 88 with the coupler 27 of the treatment section drive unit 2 inserted and engaged therein is formed at the upper portion of the movable handle 77. This connection groove 88 has the upper portion thereof formed as an inlet hole 89 having substantially the same diameter as the coupler 27. A guide hole 90 for guiding the coupler 27 downward is formed vertically in the depth of the connection groove 88. Also, the front edge of the lower portion of the connection groove 88 is formed with an engaging section 91 having a width smaller than the diameter of the coupler 27 for engaging the coupler 27. Further, the fixed handle 76 and the movable handle 77 are formed with flat butt sections 92, 93, respectively, in the neighborhood of the pivotally-supported portions thereof. As a result of the butt sections 92 and 93 coming into contact with each other, the motion of the movable handle 77 in the closing direction is restricted. Also, the upper portion of the movable handle 77 is formed with a mushroomed protrusion 94 adapted to removably engage the groove 87 of the rubber cap 86 in the case where the movable handle 77 is operated in the opening direction.

Now, explanation will be given of the case in which the treatment tool for operation 1 according to this embodiment is assembled.

As shown in FIGS. 2A and 2B, from the state in which the treatment tool for operation 1 is disassembled into component parts, the first step is to assemble the rotary engaging member 4 on the insertion section 3. In the process, the cylindrical portion 63 of the rotary engaging member 4 is inserted into the hole 39 of the holding member 38 of the insertion section 3. As a result, the hemispherical portion 75 of the lever 60 moves while sliding on the slope surface 52 and the cylindrical surface 53 of the knob 48, so that the arm 74 of the lever 60 is deformed elastically outward. Pushing in the rotary engaging member 4 further causes the hemispherical portion 75 to engage the engaging groove 56 of the knob 48, so that the arm 74 is released from the elastic deformation. Under this condition, the lever member 59 of the lever 60 is rotated to the point designated by two-dot chain in FIG. 1. Then, the elastic deformation of the arm 74 causes the hemispherical portion 75 to override the protrusion 55 of the engaging groove 56 and move to the position indicated by two-dot chain in FIG. 13. As a result, the hemispherical portion 75 engages the engaging groove 56, so that the rotary engaging member 4 is fixed with respect to the insertion section 3. Also, the common center axis x of the holes 66, 70 of the cam slots 64, 65 come to coincide with the center axis y of the sheath 29.

Then, the insertion section 3 with the rotary engaging member 4 mounted thereon is assembled on the operating section 5. In the process, the snap fit member 42 of the insertion section 3 is inserted into the small-diameter section 83 from the large-diameter section 82 of the insertion section connector 81 of the fixed handle 76. At the same time, the protrusions 44, 44 of the snap fit member 42 are smoothly inserted into the small-diameter portion 83 from the large-diameter portion 82 by being guided along the slope surfaces 45, 45, and thus move sliding in the small-diameter portion 83. Also, the snap fit arms 43, 43 are elastically deformed inward under the force from the inner surface of the small-diameter portion 83.

From this state, push in the snap fit number 42 further. The butt surface 98 of the snap fit member 42 comes into contact with the butt surface 99 of the insertion section connector 81. At the same time, the protrusions 44, 44 are pushed out of the small-diameter portion 83 and the elastic deformation of the snap fit arms 43, 43 are released.

Then, the treatment section drive unit 2 is assembled on an assembly including the insertion section 3 and the operating section 5 integrated with each other. First, the movable handle 77 is operated in the opening direction, the portion of the rubber cap 86 in the neighborhood of the groove 87 is elastically deformed by the protrusion 94 of the movable handle 77 thereby causing the protrusion 94 to engage the groove 87. At the same time, the movable handle 77 is held at the position indicated by solid line in FIG. 17, and the inlet hole 89 of the movable handle 77 substantially coincides with the center axis y of the sheath 29. Specifically, the movable handle 77 is in a specified position permitting correct assembly. Continue to insert the coupler 27 of the treatment section drive unit 2 into the sheath 29 from the forward end of the sheath 29. The s lope surface 19 (20) of the protrusions 16, 16 of the connector 14 comes into contact with the slope surface 31a (31b) of the engaging groove 31 of the pipe 30, so that the protrusions 16, 16 are guided by the insertion guide 33 of the engaging groove 31. Push in the treatment section drive unit 2 further The coupler 27 is inserted in the inlet hole 89 of the movable handle 77. Under this condition, push in the treatment section drive unit 2 while rotating the movable handle 77 to the position indicated by two-dot chain in the closing direction. The portion of the rubber cap 86 in the neighborhood of the groove 87 is elastically deformed so that the protrusion 94 and the groove 87 are disengaged from each other. At the same time, the coupler 27 is guided downward of the connection groove 88 along the guide hole 90 and comes to engage the engaging portion 91. Also, this operation causes the protrusions 16, 16 guided by the insertion guide 33 to proceed along the insertion guide 33 and, overriding by elastically deforming the inner protrusions 35, 35 of the forward end pipe 32, move to the position in the engaging groove 31 shown in FIG. 19A. At the same time, the butt surface 15 of the connector 14 comes into contact with the butt surface 30a of the pipe 30.

Under this condition, the treatment section drive unit 2 fails to move forward as long as the protrusion 16 of the treatment section drive unit 2 exerts a sufficient force on the treatment section drive unit 2 to elastically deform the inner protrusions 35, 35 of the forward end pipe 32.

Figure 13:
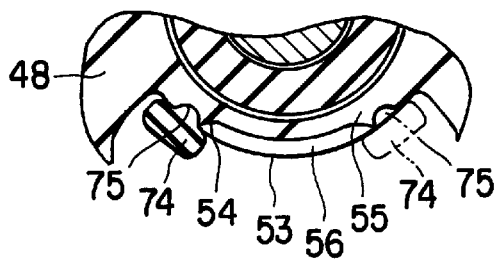
FIG. 13 is a sectional view taken in line H—H in FIG. 12.

Next, upon rotation of the lever member 59 of the lever 60 from the position indicated by two-dot chain to the position indicated by solid line, the hemispherical portion 75 overrides the protrusions 55, 54 of the engaging groove 56 and moves to the position indicated by solid line in FIG. 13, so that the rotary engaging member 4 is fixed in the insertion section 3. At this time, the relative positions between the protrusions 16, 16 and the engaging groove 31 and the relative positions between the cylindrical cam slots 64, 65 and the drive shaft 24 change from the one shown in FIG. 19A to the one shown in FIG. 19B and then to the one shown in FIG. 19C. Specifically, the rotation of the lever 60 causes the rotation of the cylindrical portion 63. Then, the slope sections 68, 72 of the cylindrical cam slots 64, 65 cause the drive shaft 24 to rotate about the center axis thereof. As a result, the treatment section drive unit 2 is rotated with respect to the insertion section 3, and the protrusions 16, 16 are guided to the engaging section 34 of the engaging slot 31. At the same time, even if the protrusions 16, 16 are displaced somewhat forward of the engaging section 34, the slope surfaces 21, 31c guide the protrusions 16, 16 toward the engaging section 34.

In the state shown in FIG. 19C, the protrusions 16, 16 are located at the engaging section 34 of the engaging groove 31, and the butt surface 17 of the protrusion 16 is in contact with the front surface of the engaging section 34. Also, the two parallel planes 26, 26 of the drive shaft 24 are located in the parallel grooves 67, 71 of the cylindrical cam slots 64, 65. Consequently, the engagement of the connector 14 with the pipe 30 restricts the movement of the treatment section drive unit 2 longitudinally of the insertion section 3. Since the drive shaft 24 is located in the cylindrical cam slots 64, 65, the rotation of the treatment section drive unit 2 with respect to the insertion section 3 is restricted.

With the treatment tool for operation 1 assembled in the above-described manner, once the movable handle 77 is rotated, the drive shaft 24 is moved longitudinally through the coupler 27 and the holding members 6, 6 are opened or closed through the drive member 23. Also, the rotation of the rotary operation section 47 of the knob 48 rotates the insertion section 3 and the treatment section drive unit 2 with respect to the operating section 5.

According to this embodiment, the amount L (see FIG. 17) by which the movable handle 77 moves from the correct assembly position (the position indicated by solid line in FIG. 17) to the position where the butt surface 15 of the connector 14 and the butt surface 30a of the pipe 30 come into contact with each other (the position indicated by two-dot chain in FIG. 17) is set smaller than the length m (see FIG. 8) of the engaging groove 31. As a result, as long as the protrusion 16 is not inserted into the engaging groove 31, the coupler 27 is not coupled with the movable handle 77.

Figure 18:
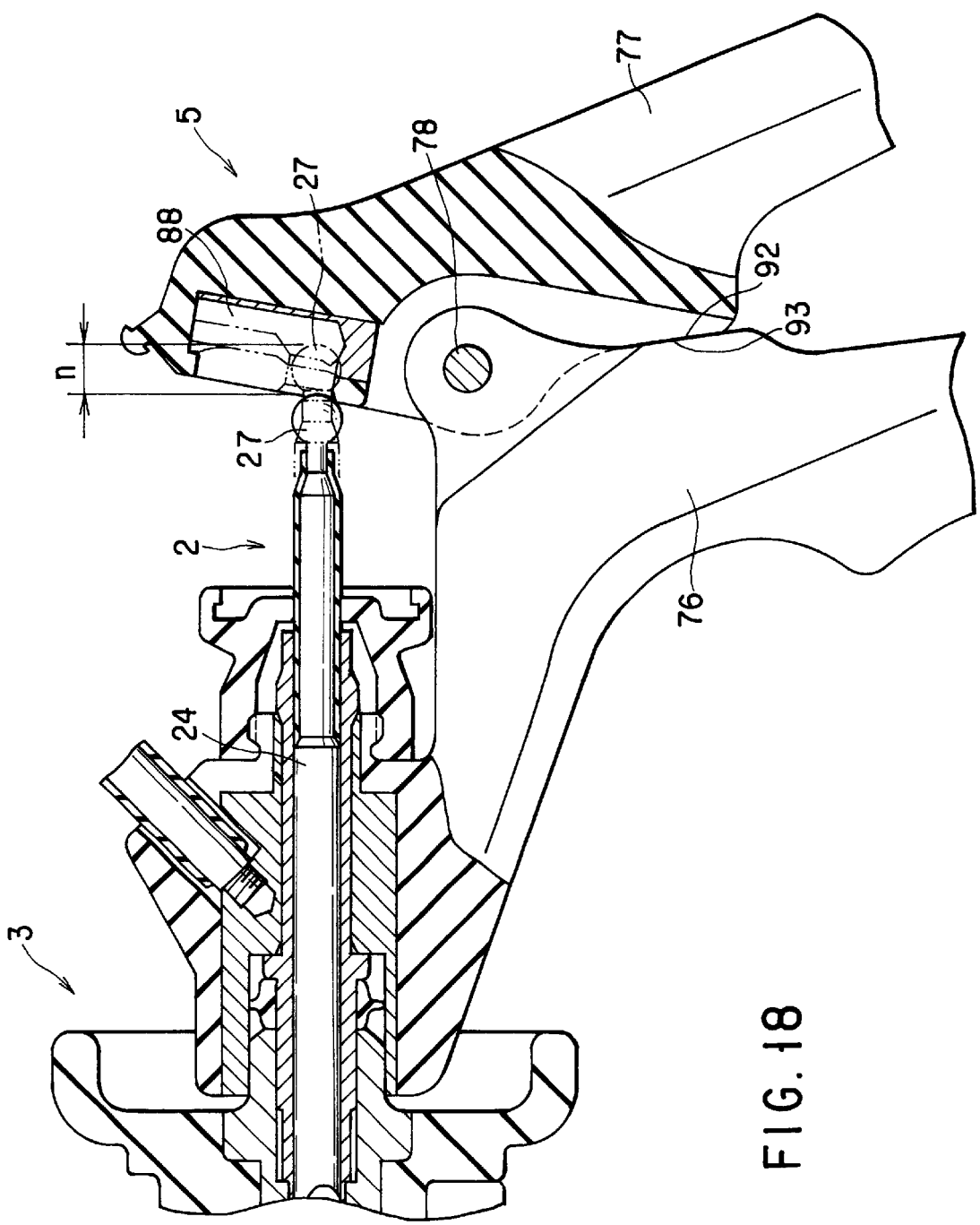
FIG. 18 is a sectional view showing the state of the treatment section drive unit of the treatment tool for operation of FIG. 1 about to be assembled in wrong mounting positions of the insertion section and the operating section.

Also, according to this embodiment, an attempt to assemble the treatment section drive unit 2 under a condition not allowing the movable handle 77 to rotate in the opening direction at the time of assembly leads to the situation shown in FIG. 18. Specifically, the end surface of the coupler 27 is butted with the front surface of the connection groove 88 of the movable handle 77. At the same time, the motion of the movable handle 77 to closing direction is restricted by the butting of the butt sections 92, 93. Therefore, the treatment section drive unit 2 cannot be pushed in further toward the user from the state shown in FIG. 18. Also, since the protrusion 16 is at a position not to be engaged by the engaging section 34 of the engaging groove 31, the treatment section drive unit 2 is not connected to the insertion section 3.

The state in which the coupler 27 is assembled by the right assembly method is shown by two-dot chain in FIG. 18 (or in FIGS. 3A and 3B). According to this embodiment, the displacement n is set larger than the maximum coverage of the drive shaft 24 moved forward for driving the holding members 6, 6. As a result, an attempt to assemble the tool with the holding members 6, 6 open would fail to cause the protrusion 16 to engage the engaging section 34 and fail to cause the treatment section drive unit 2 to be connected to the insertion section 3. Specifically, the treatment section drive unit 2 is not connected to the insertion section 3 unless coupled to the operating section 5.

Now, explanation will be given of the case in which the assembled treatment tool for operation 1 is disassembled. First, the lever member 59 of the lever 60 is rotated from the position indicated by solid line to the position indicated by two-dot chain in FIG. 11. The hemispherical portion 75 moves to the position indicated by two-dot chain in FIG. 13 over the protrusions 54, 55 of the engaging groove 56. By the way, even under this condition, the rotary engaging member 4 is kept fixed on the insertion section 3. Also, under this condition, the relative positions of the protrusions 16, 16 and the engaging groove 31 and the relative positions of the cylindrical cam slots 64, 65 and the drive shaft 24 are as shown in FIG. 19D. From this state, rotate the treatment section drive unit 2 by holding the holding members 6, 6 with respect to the insertion section 3. The state as shown in FIG. 19A is attained. After that, operate to open the movable handle 77 to the position indicated by solid line in FIG. 17, and pull the treatment section drive unit 2 toward the forward end. The protrusions 16, 16 cause the elastic deformation of the inner protrusions 35, 35 of the forward end pipe 32, so that the protrusions 16, 16 proceed forward over the inner protrusions 35, 35 along the insertion guide 33. At the same time, the drive shaft 24 and the coupler 27 pass through the holes 70, 66 of the cylindrical cam slots 65, 64. The treatment section drive unit 2 thus is separated from the insertion section 3.

Next, for separating the rotary engaging member 4 and the insertion section 3 from the operating section 5, the insertion section 3 is pulled forward with respect to the operating section 5. As a result, the protrusions 44, 44 of the snap fit member 42 are inserted in the small-diameter section 83 by being guided by the slope surfaces 46, 46 and move while sliding within the s mall-diameter section 83. At the same time, the snap fit arms 43, 43 are elastically deformed inward. When the insertion section 3 is pulled further forward, the protrusions 44, 44 are projected outside of the small-diameter section 83, and the elastic deformation of the snap fit arms 43, 43 is canceled. In other words, the rotary engaging member 4 and the insertion section 3 are separated from the operating section 5.

Next, in order to separate the rotary engaging member 4 from the insertion section 3, the rotary engaging member 4 is pulled upward with respect to the insertion section 3. By doing so, the arm 74 is elastically deformed and the hemispherical portion 75 is disengaged from the engaging groove 56, so that the hemispherical portion 75 is moved while sliding along the slope surface 52 and the cylindrical surface 53 of the knob 4B. When the engaging member 4 is pulled further upward under this condition, as shown in FIGS. 2A and 2B, the rotary engaging member 4 is separated from the insertion section 3.

As described above, according to this embodiment, the component elements c an be easily disassembled and assembled within a short time. Also, the rotary engaging member 4 for fixing the treatment section drive unit 2 in the rotational direction with respect to the insertion section 3 can be disassembled. The connector of the component parts lacks a screw-type coupling mechanism. Therefore, portions difficult to clean such as the tops and roots of the thread of the screw-type coupling mechanism are eliminated. Consequently, the treatment tool for operation 1 according to this embodiment is suitably used as a medical equipment requiring a high degree of cleanliness.

Also, according to this embodiment, unless the protrusion 16 is inserted in the engaging groove 31, the engaging section 27 is never coupled to the movable handle 77. Also, the treatment section drive unit 2, unless coupled to the operating section 5, is never connected to the insertion section 3. As a result, it is not necessary to repeat the assembly and disassembly due to an assembly error. Further, the pipe 30, the connector 14 and the coupler 27 are prevented from being broken by an excessive operating force which would be exerted on them while the assembly work is erroneous.

FIGS. 20A to 23 show a second embodiment of the invention. This embodiment is different from the first embodiment only in the method of connecting the insertion section 3 and the operating section 5. Only the differences from the first embodiment will be explained below.

Figure 20A:
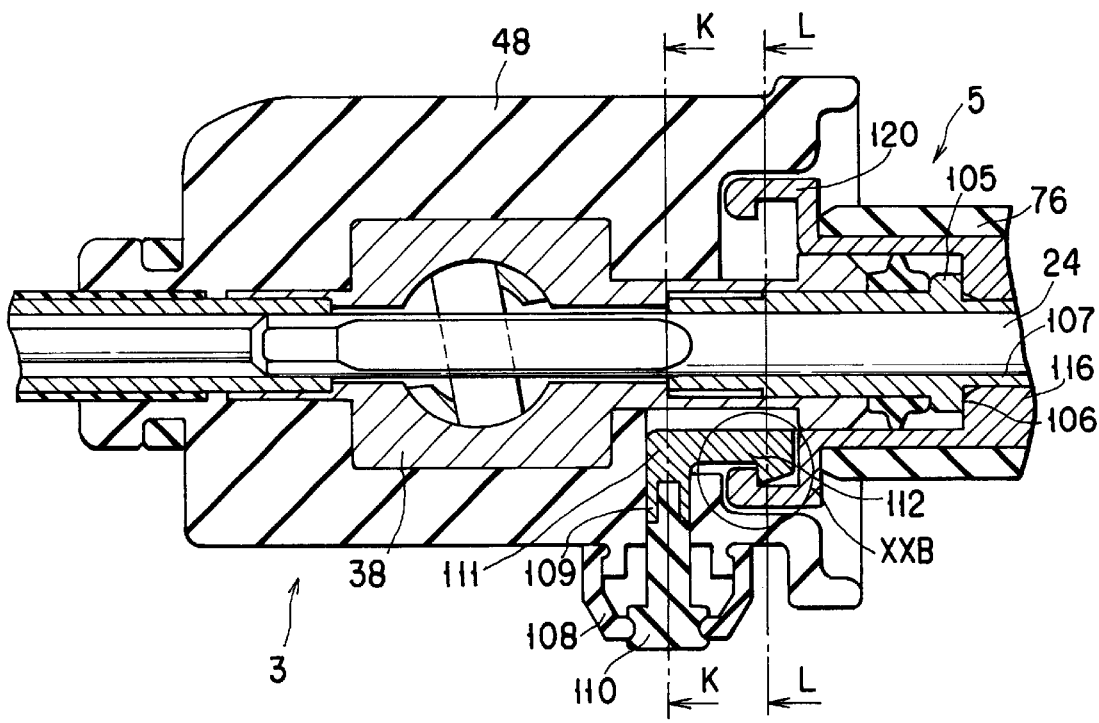
FIG. 20A is a cross sectional view of a treatment tool for operation according to a second embodiment of the invention.
Figure 20B:
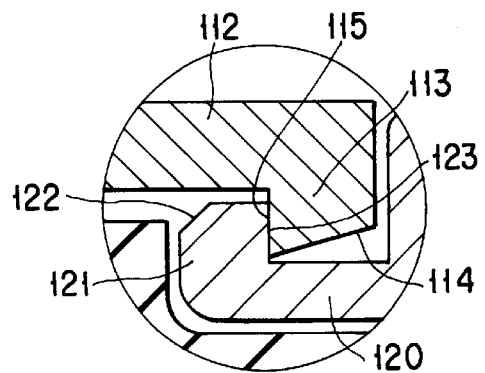
FIG. 20B is an enlarged sectional view of a part XXB shown in FIG. 20A.

As shown in FIGS. 20A and 20B, the drive shaft support member 105 is integrated with the base end of the holding member 38. The drive shaft support member 105 is formed with a butt surface 106. Also, the base end side of the drive shaft support member 105 is formed with a cylindrical portion 107 for inserting the drive shaft 24 therethrough.

As shown in FIGS. 20A to 22, a deformable rubber spring (biasing means) 108 made of an elastic material such as synthetic rubber is arranged removably on the knob 48. A guide member (pressure section) 110 made of an electrically insulating material is removably arranged on the rubber spring 108. This guide member 110 is supported movably only in vertical direction (vertical direction in FIGS. 20A, 20B and 22) by the guide hole 109 formed in the knob 48.

As shown in detail in FIGS. 20A and 20B, the extreme end of the guide member 110 is formed integrally with an operating section engaging/disengaging member (engaging/disengaging member) 111. The operating section engaging/disengaging member 111 is formed with a support 112 extending rearward, and the forward end of the support member 112 is formed with an engaging protrusion 113. The engaging protrusion 113 is formed with a slope surface 114 and a butt surface 115.

Figure 21:
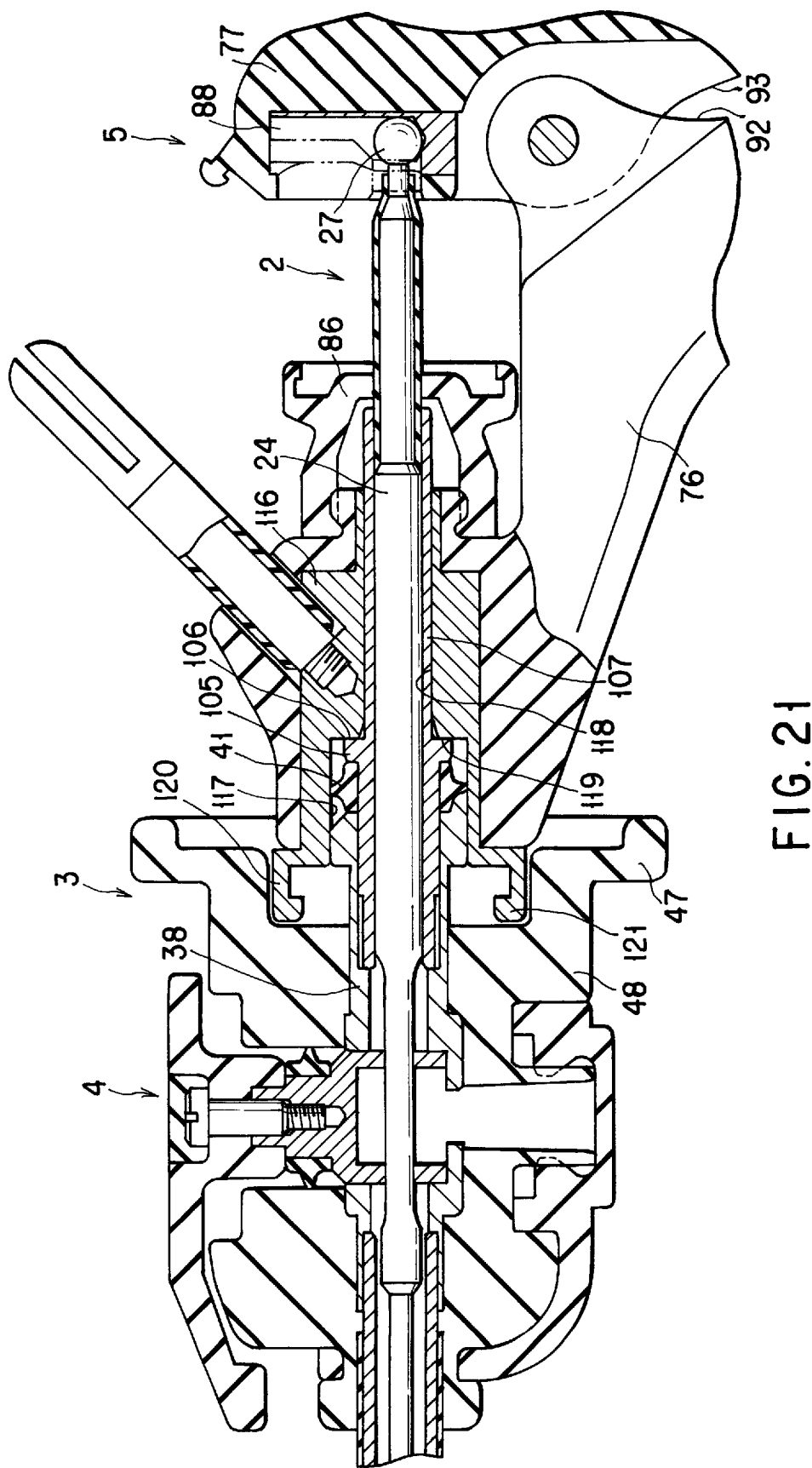
FIG. 21 is a longitudinal sectional view showing the treatment tool for operation of FIG. 20A.
Figure 22:
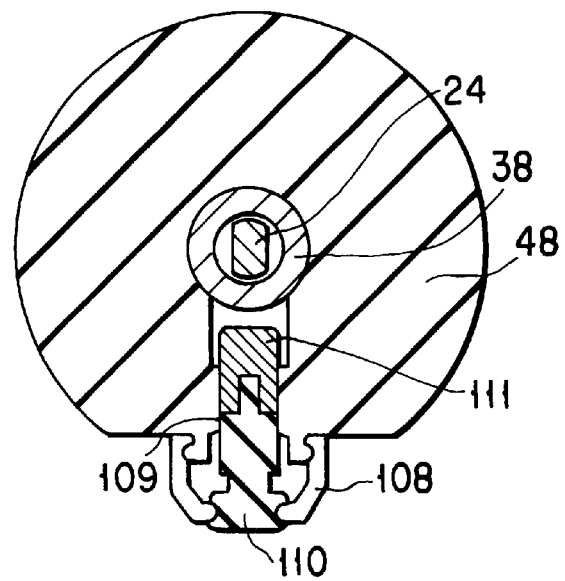
FIG. 22 is a sectional view taken in line K—K in FIG. 20A.
Figure 23:
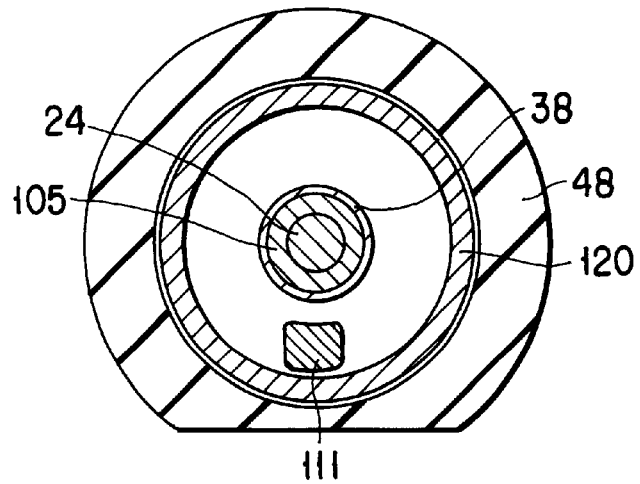
FIG. 23 is a sectional view taken in line L—L in FIG. 20A.
Figure 24:
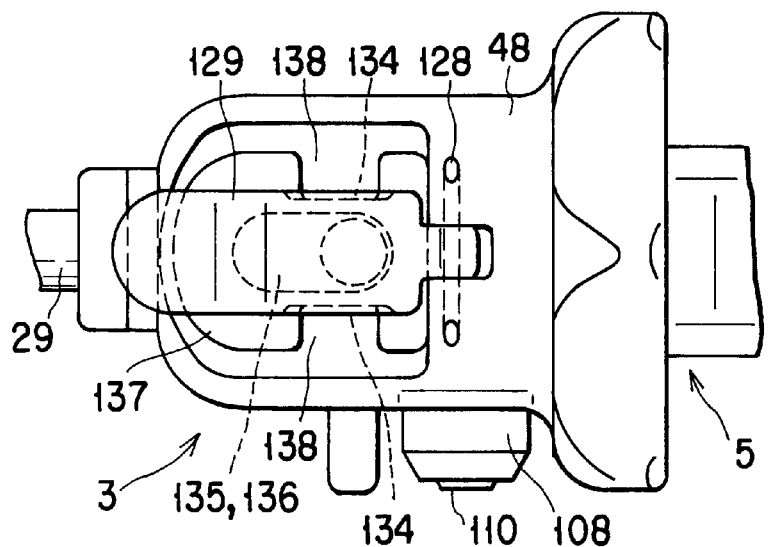
FIG. 24 is a plan view of a treatment tool for operation according to a third embodiment of the invention.

As shown in FIG. 21, an insertion section connector 116 is arranged above the fixed handle 76. The insertion section connector 116 has formed therein a large-diameter section 117 for accommodating the rubber packing 41 of the insertion section 3, and a small-diameter section 118 located rearward of the large-diameter section 117 for accommodating the cylindrical portion 107 of the drive shaft support member 105. A butt surface 119 for contacting the butt surface 106 of the drive shaft support member 105 is formed between the large-diameter section 117 and the small-diameter section 118. A cylindrical section 120 having an inner diameter larger than the large-diameter section 117 is formed forward of the large-diameter section 117. An engaging section 121 for engaging the engaging protrusion 113 is formed at the forward end of the cylindrical portion 120. As shown in detail in FIG. 20, the engaging section 121 is formed with a slope surface 122 and a butt surface 123 adapted for contacting the butt surface 115 of the engaging protrusion 113.

Now, the operation of the second embodiment will be explained.

For assembling the insertion section 3 on the operating section 5, the first step is to insert the cylindrical surface 107 of the drive shaft support member 105 of the insertion section 3 into the small-diameter section 118 from the large-diameter section 117 of the insertion section connector 116 of the fixed handle 76. In the process, the slope surface 114 of the engaging protrusion 113 comes into contact with the slope surface 122 of the engaging section 121, so that the guide member 110 and the operating section engaging/disengaging member 111 are guided by the guide hole 109 of the knob 48 against the elastic force of the rubber spring 108 and thus moves upward in FIGS. 20A and 20B. Further, when the insertion section 3 is pushed further into the operating section 5, the butt surface 106 of the drive shaft support member 105 comes into contact with the butt surface 119 of the insertion section connector 116. At the same time, the restitutive power of the rubber spring 108 causes the guide member 110 and the operating section engaging/disengaging member 111 to move downward in FIGS. 20A and 20B by being guided by the guide hole 109. Specifically, as shown in FIGS. 20A and 20B, the butt surface 115 of the engaging protrusion 113 and the butt surface 123 of the engaging section 121 assume a state butted with each other, thus completing the assembly of the insertion section 3 in the operating section 5.

Next, explanation will be given of the case in which the insertion section 3 is separated from the operating section 5. First, under the condition shown in FIGS. 20A and 20B, the guide member 110 is pushed upward against the elasticity of the rubber spring 108. The operating section engaging/disengaging member 111 is also moved upward, and the engaging protrusions 113 comes off from the engaging section 121. When the insertion section 3 is moved forward of the operating section 5 while the guide member 110 is kept pushed up, the insertion section 3 is separated from the operating section 5.

By the way, according to the first embodiment, it is impossible, by reason of the construction, to assemble or separate the insertion section 3 on or from the operating section 5 with the treatment drive unit 2 assembled on the insertion section. This is due to the fact that the snap fit arm 43 cannot be elastically deformed inward with the drive shaft 24 inserted in the snap fit member 42 of the insertion section 3. In the configuration of the present embodiment, however, the insertion section with the treatment section drive unit 2 assembled thereon can be assembled on or separated from the operating section 5. Specifically, in the case where an assembly having the treatment section drive unit 2 mounted on the insertion section 3 using the rotary engaging member 4 is assembled on the operating section 5 or separated from the operating section 5, what is required is to cause the coupler 27 of the treatment section drive unit 2 described with reference to the first embodiment to engage or disengage from the connection groove 88 of the movable handle 77, as well as to do the job of disassembling/assembling the insertion section 3 and the operating section 5 described in this embodiment. In the process, an attempt to mount the above-mentioned assembly by pushing it into the operating section 5 without rotating the movable handle 77 in the opening direction would cause the butt sections 92 and 93 to come into contact with each other, and the motion of the movable handle 77 in the closing direction is restricted, so that the end surface of the coupler 27 contacts the front surface of the connection groove 88 of the movable handle 77. The above-mentioned assembly thus cannot be pushed in to the position where the engaging protrusion 113 of the insertion section 3 engages the engaging section 121 of the operating section 5. In other words, an erroneous assembly is prevented.

As described above, according to this embodiment, the treatment section drive unit 2 alone or the operating section 5 alone can be mounted or demounted with ease and rapidity. As a result, the treatment section drive unit 2 or the operating section 5 which are damaged can be replaced with rapidity, or the treatment section drive unit 2 or the operating section 5 having different profiles or functions can be replaced with rapidity.

FIGS. 24 to 28C show a third embodiment of the invention. The treatment tool for operation according to this embodiment is different from the second embodiment only in the means for restricting the rotation of the treatment section drive unit 2 relative to the insertion section 3. Therefore, only those component parts different from the second embodiment will be explained.

Figure 25:
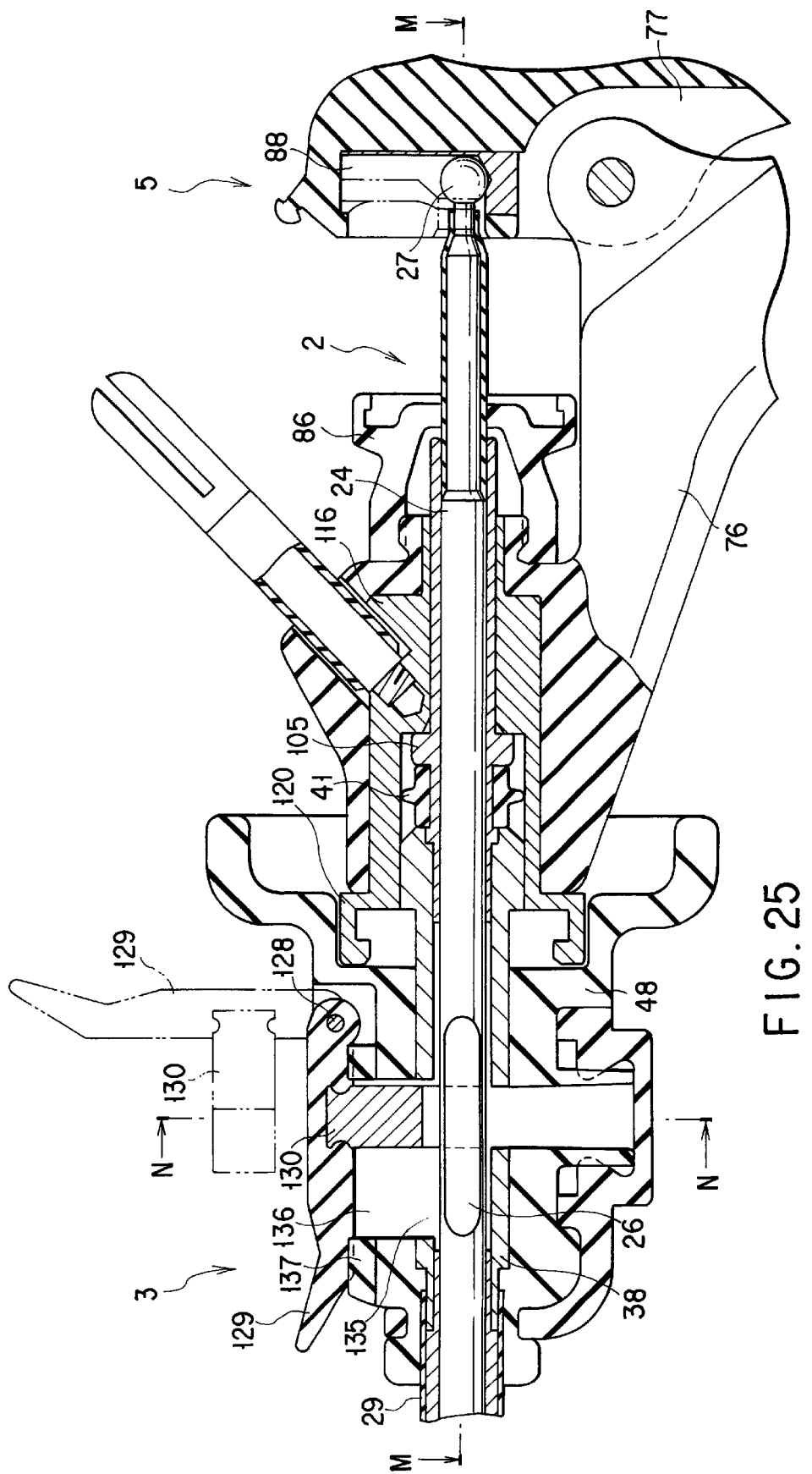
FIG. 25 is a longitudinal sectional view of the treatment tool for operation of FIG. 24.

As shown in FIG. 25, a lever 129 made of an electrically insulating material is rotatably mounted on the knob 48 through a pin 128. The lever 129 is integrated with a circular cylindrical fork member (rotary engaging member) 130.

Figure 27:
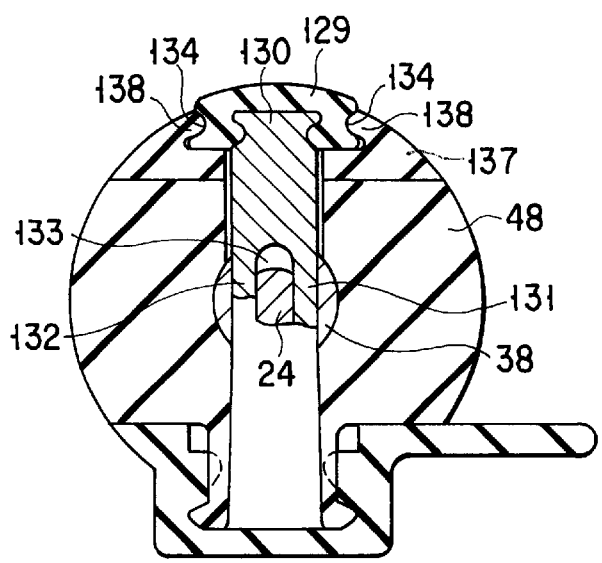
FIG. 27 is a sectional view taken in line N—N in FIG. 25.

As shown in FIG. 27 (sectional view taken in line N—N in FIG. 25), the forward end of the fork member 130 is formed with a long leg (leg) 131 and a short leg (leg) 132. A groove 133 parallel to and adapted to engage two parallel planes 26, 26 of the drive shaft 24 is formed between the long leg 131 and the short leg 131. Also, recesses (mounting/demounting section) 134, 134 are formed on the side of the lever 129. In order that the fork 130 rotating with the lever 129 may not interfere with the holding member 38 and the knob 48, the holding member 38 and the knob 48 are formed with slots 135, 136 as shown in FIG. 25.

Figure 26:
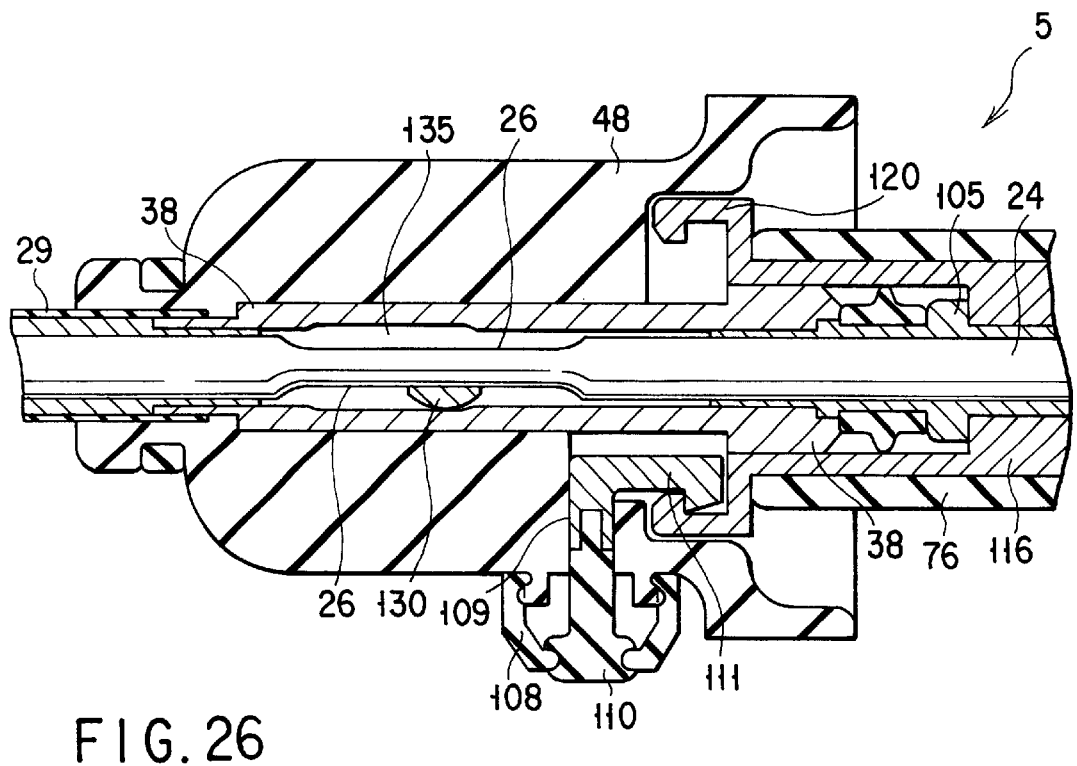
FIG. 26 is a sectional view taken in line M—M in FIG. 25.

Also, the knob 48 is integrated with a rubber packing 137 made of an elastic material such as synthetic rubber. This rubber packing 137 maintains the interior of the insertion section 3 in hermetic state by contacting the lever 129. Also, the rubber packing 137 is formed with ears (mounting/demouning sections) 138, 138 adapted to removably engage the recesses 134, 134 of the lever 129, as shown in FIGS. 25 to 27.

Next, the operation of the third embodiment will be explained.

In the case where the treatment section drive unit 2 is assembled on the insertion section 3, the first step is to rotate the lever 129 up to the position indicated by two-dot chain in FIG. 25. In this case, the lever 129 can be held at the position indicated by the two-dot chain by a holding means not shown. Under this condition, the next step is to insert the coupler 27 of the treatment section drive unit 2 into the forward end of the sheath 29, and the treatment section drive unit 2 is pushed into the insertion section 3 until the butt surface 15 of the connector 14 comes into contact with the butt surface 30a of the pipe 30. The relative positions of the protrusion 16 and the engaging groove 31 with the butt surface 15 in contact with the butt surface 30a are shown in FIG. 28A.

From this state, the lever 129 is rotated downward to the position indicated by solid line in FIG. 25. The ear 138 of the rubber packing 137 is elastically deformed and engages the recess 134 (see FIG. 27) of the lever 129, so that the lever 129 is fixed on the insertion section 3. At this time, the relative positions of the protrusions 16, 16 and the engaging groove 31 and the relative positions of the fork member 130 and the drive shaft 24 undergo a change from the state shown in FIG. 28A to the state shown in FIG. 28B and further to the state shown in FIG. 28C. Specifically, with the rotation of the lever 129, the long leg 131 of the fork member 130 pushes one of the planes of the drive shaft 24 and causes the drive shaft 24 to rotate about the center axis thereof. As a result, the protrusion 16 is guided to the engaging section 34 of the engaging groove 31. Finally, as shown in FIG. 28C, the protrusion 16 is located on the engaging section 34 of the engaging groove 31, so that the butt surface 17 of the protrusion 16 comes into contact with the front surface of the engaging section 34. At the same time, the two parallel planes 26, 26 of the drive shaft 24 engage the parallel groove 133 of the fork member 130. In other words, the treatment section drive unit 2 is assembled on the insertion section 3.

In the case where the treatment section drive unit 2 is separated from the insertion section 3, on the other hand, the lever 129 is rotated upward to the position indicated by two-dot chain in FIG. 25. At the same time, the ear 138 of the rubber packing 137 is elastically deformed so that the recess 134 of the lever 129 is disengaged from the ear 138. After that, the treatment section drive unit 2 is rotated with respect to the insertion section 3 by holding the holding members 6, 6 of the treatment section drive unit 2 thereby to set the unit 2 in the state shown in FIG. 28A. Under this condition, the treatment section drive unit 2 is pulled toward the forward end thereof. Then, the treatment section drive unit 2 can be separated from the insertion section 3. By the way, according to the present embodiment, like the second embodiment, the order of disassembly or assembly of the treatment section drive unit 2, the insertion section 3 and the operating section 5 is not limited.

As described above, according to this embodiment, the fork member 130 for restricting the rotation of the treatment section drive unit 2 with respect to the insertion section 3 is rotatably mounted on the insertion section 3 through the lever 129. Therefore, the loss of the fork member 130 is prevented. Also, according to this embodiment, the disassembly/assembly work of the component elements can be easily accomplished within a short length of time. Also, the treatment tool for operation according to this embodiment has no parts difficult to w ash, and therefore provides a suitable medical equipment requiring a high degree of cleanliness. Especially, when the lever 129 is rotated upward with the treatment section drive unit 2 separated from the insertion section 3, the washability of the interior of the insertion section 3 can be improved.

FIGS. 29 to 34 shows a fourth embodiment of the invention. The treatment tool for operation according to this embodiment is different from the second embodiment only in the means for restricting the rotation of the treatment section drive unit 2 with respect to the insertion section 3. Therefore, only the components different from the second embodiment will be explained.

In the first to third embodiments, the tube 28 made of an electrically insulating material is provided in the neighborhood of the base end of the drive shaft 24 of the treatment section drive unit 2. This embodiment lacks such a tube.

Figure 29:
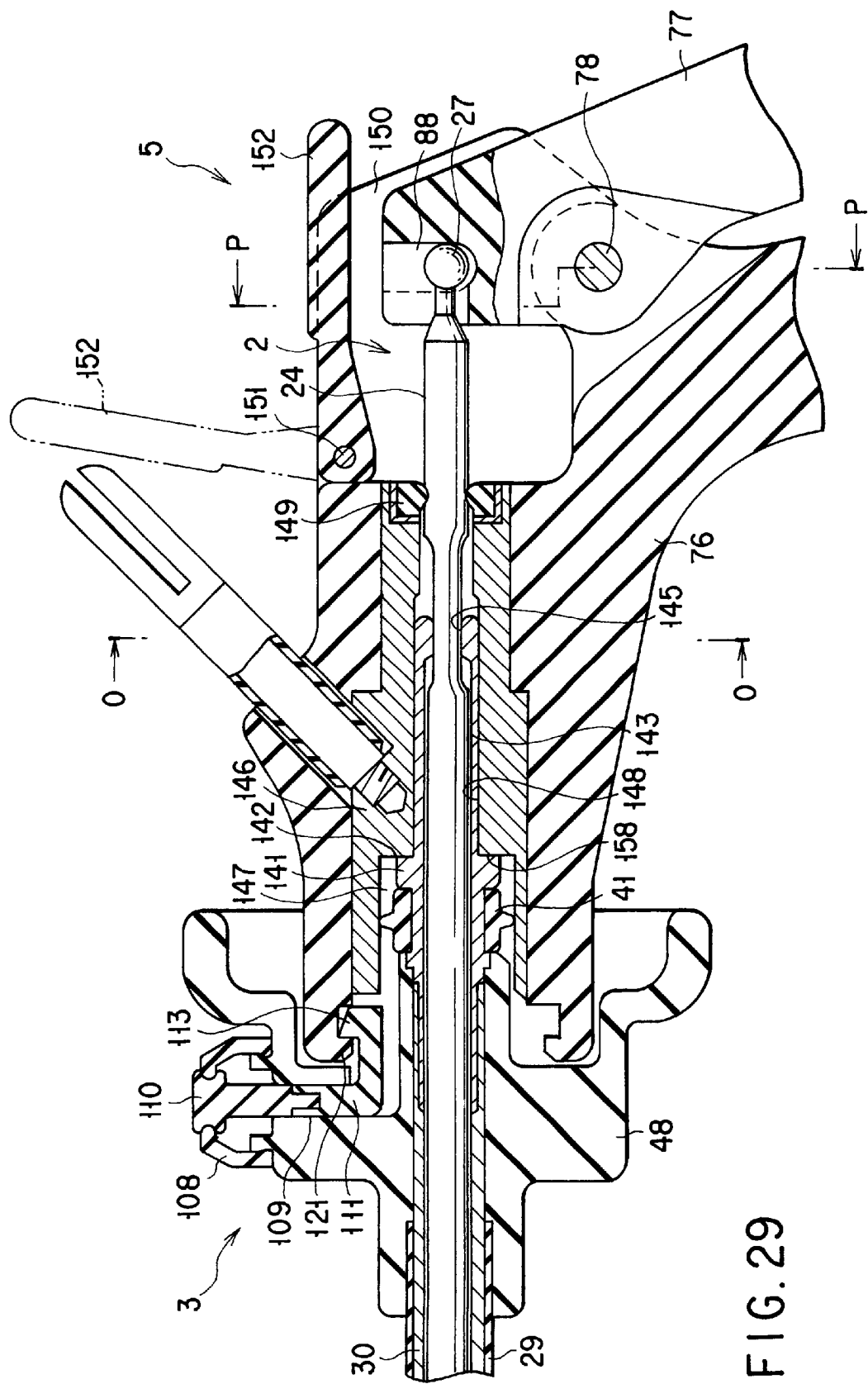
FIG. 29 is a partial sectional view of a treatment tool for operation according to a fourth embodiment of the invention.
Figure 30:
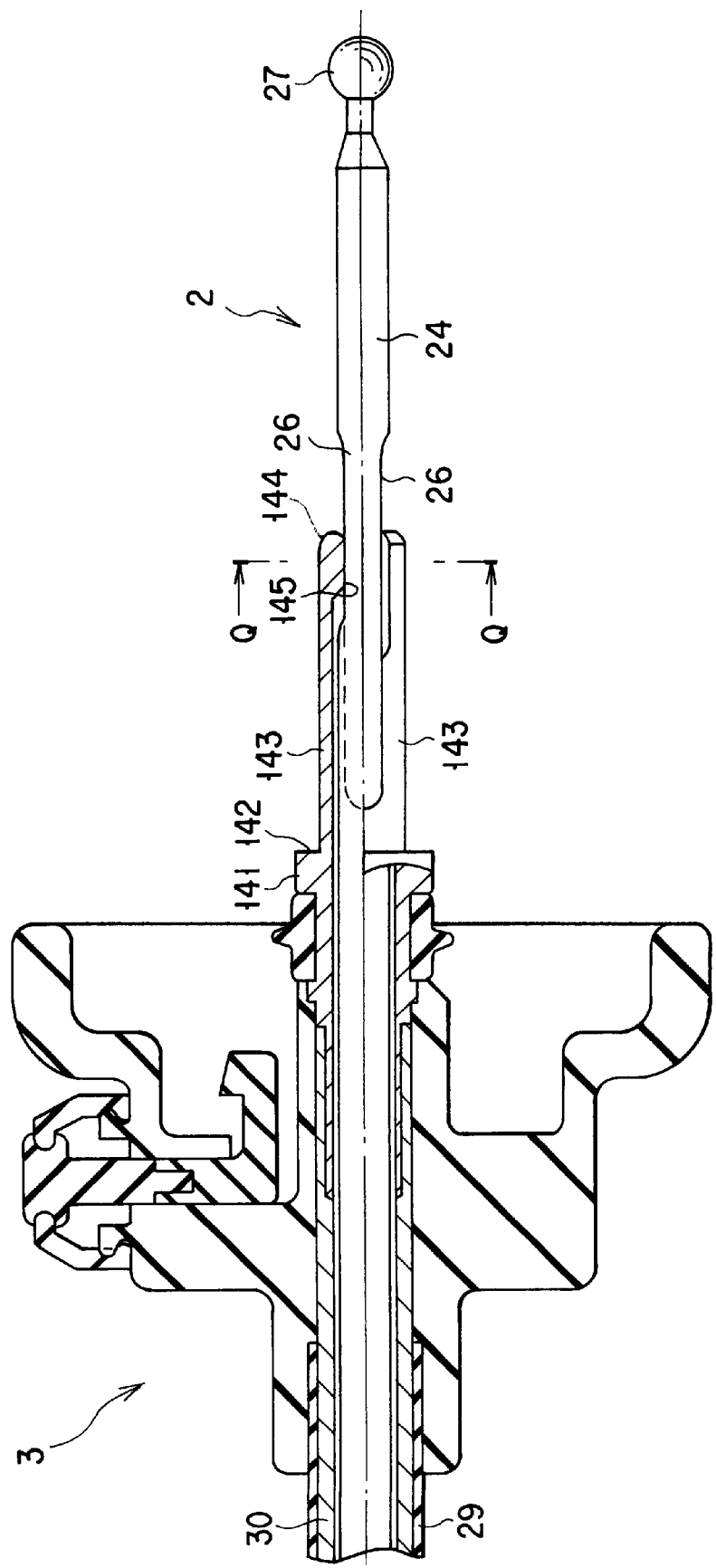
FIG. 30 is a sectional view showing the state of the treatment section drive unit of the treatment tool for operation of FIG. 29 assembled in the insertion section.

As shown in FIGS. 29 and 30, the base end of the pipe 30 of the insertion section 3 is formed integrally with the rotary engaging member 141. The rotary engaging member 141 is formed with a butt surface 142 and two snap fit arms 143, 143 of cantilever type. A protrusion 144 is erected from the inside at the forward end of each snap fit arm 143. The protrusion 144 is formed with a parallel section 145 adapted to engage the two parallel planes 26, 26 of the drive shaft 24.

An insertion section holder 146 is arranged above the fixed handle 76. The insertion section holder 146 has formed therein a large-diameter section 147 for accommodating the rubber packing 41 of the insertion section 3, and a small-diameter section 148 formed rearward of the large-diameter section 147 for accommodating the snap fit arm 143 of the rotary engaging member 141. A butt surface 158 is formed between the large-diameter section 147 and the small-diameter section 148. Also, an annular rubber packing 149 through which the drive shaft 24 is inserted is arranged at the base end of the insertion section holder 146. According to this embodiment, an engaging section 121 for engaging the engaging protrusion 113 of the operation section engaging/disengaging member 111 of the insertion section 3 is formed on the fixed handle 76.

Walls 150, 150 for covering the vicinity of the connection groove 88 of the movable handle 77 are formed above the fixed handle 76. The walls 150, 150 have rotatably mounted thereon a cover 152 made of an electrically insulating material through a pin 151. This cover 152 covers the upper part of the neighborhood of the connection groove 88 of the movable handle 77. As shown in detail in FIG. 31B (sectional view taken in line P—P in FIG. 29), the cover 152 is formed with hemispherical protrusions 153, 153. Also, the walls 150, 150 are formed with holes 154, 154 adapted to engage the protrusions 153, 153.

Figure 33:
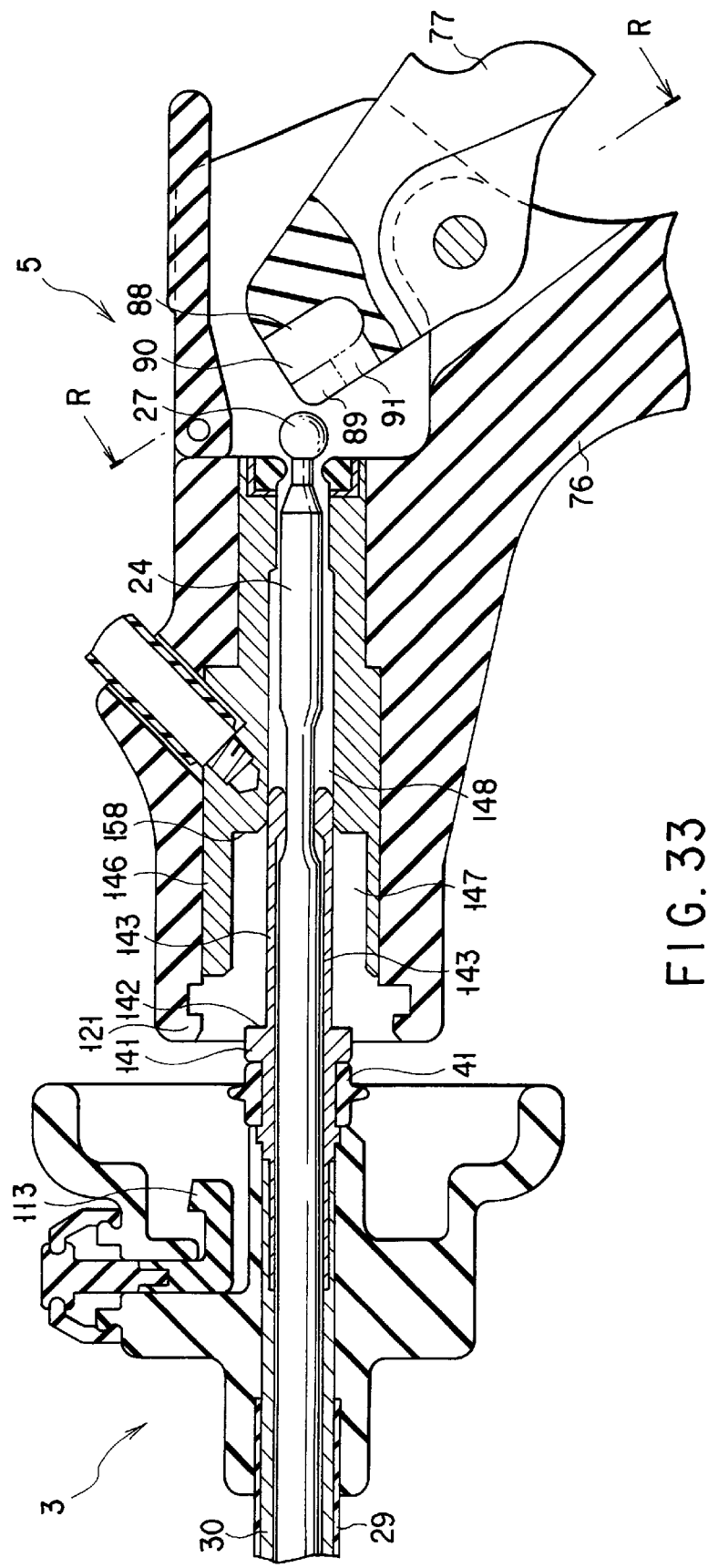
FIG. 33 is a sectional view showing the state of the treatment section drive unit and the insertion section of the treatment tool for operation of FIG. 29 assembled in correct mounting positions of the operating section.
Figure 34:
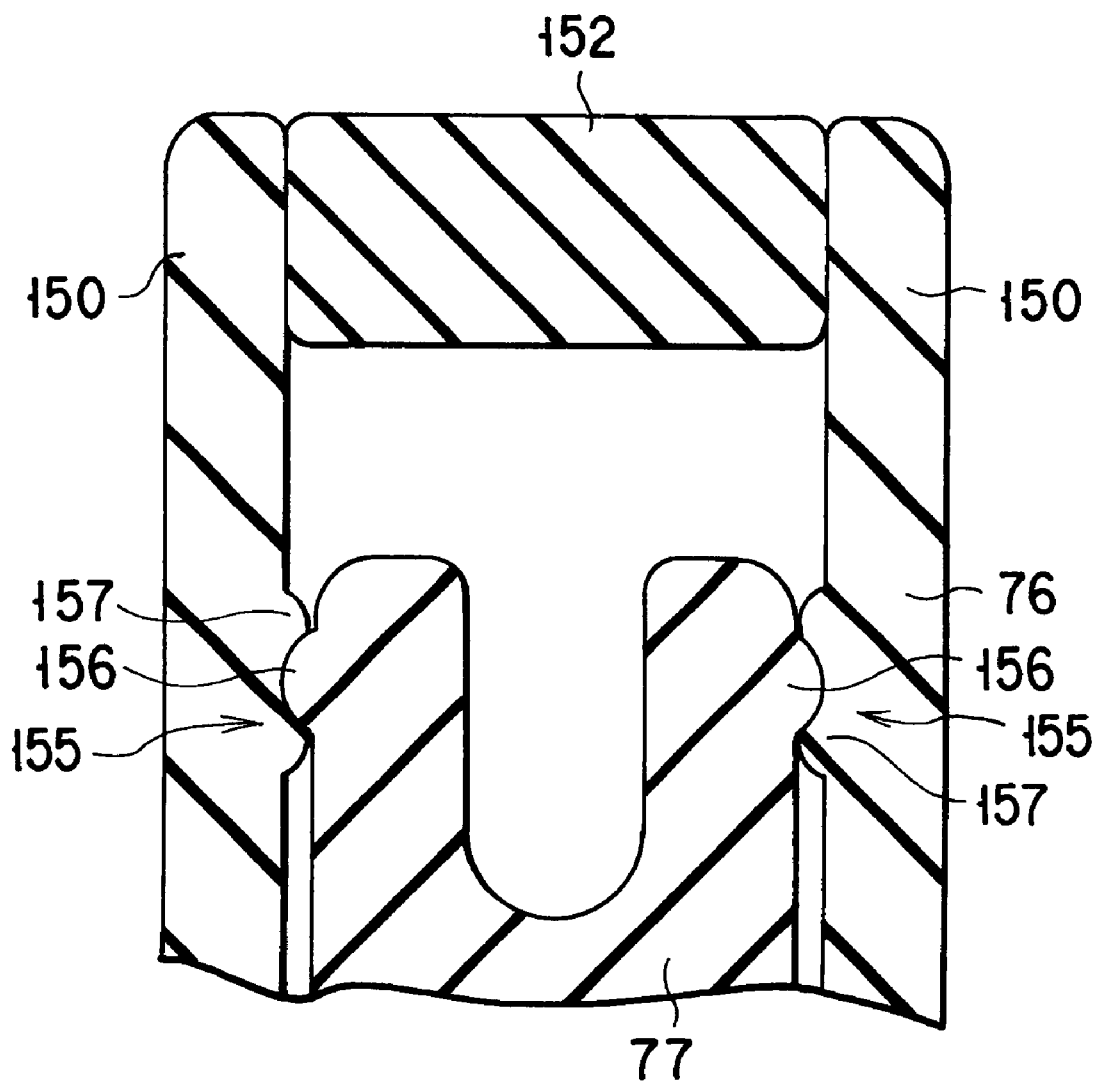
FIG. 34 is a sectional view taken in line R—R in FIG. 33.
Figure 35:
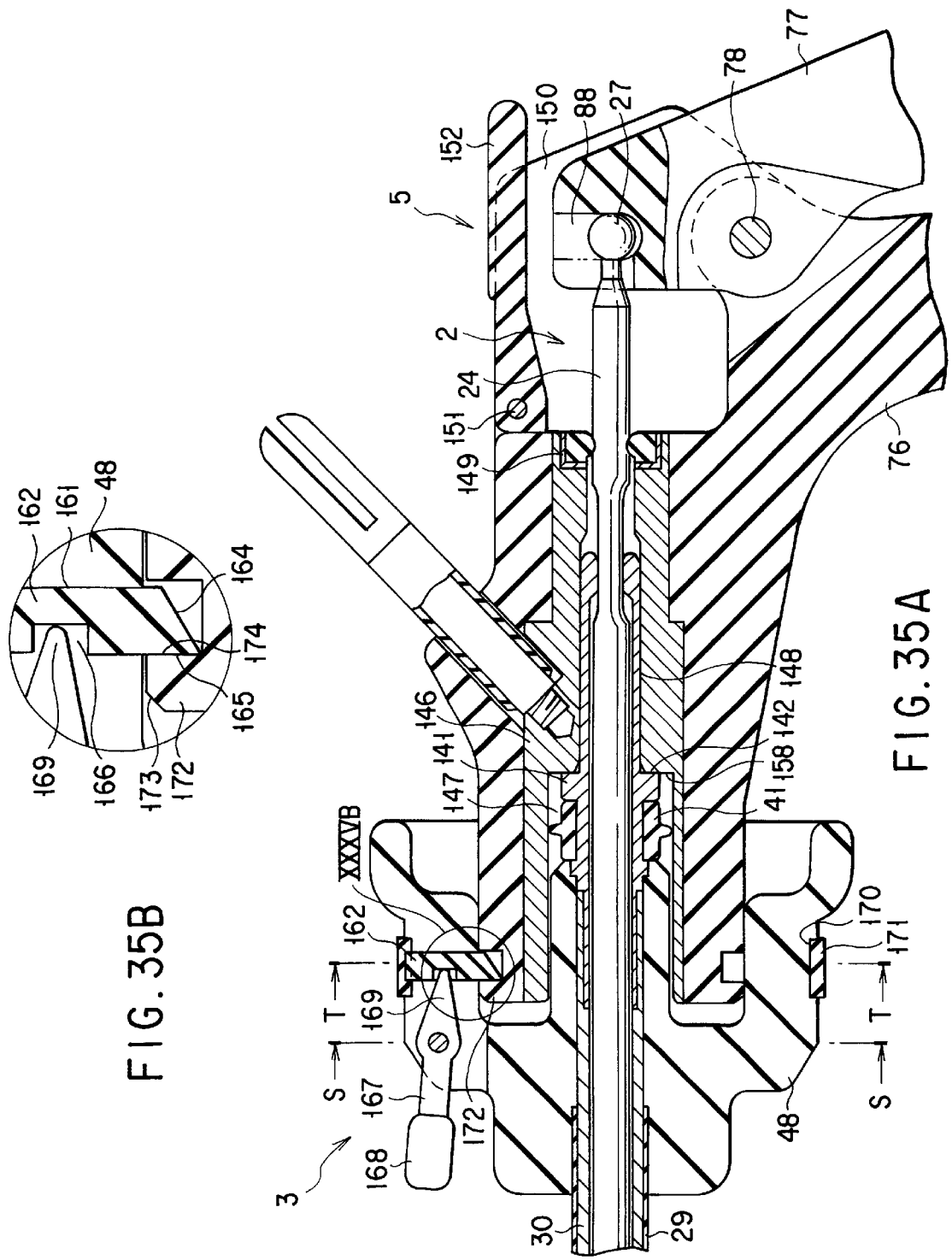
FIG. 35A is a partial sectional view of a treatment tool for operation according to a fifth embodiment of the invention.
FIG. 35B is an enlarged sectional view of a part XXXVB shown in FIG. 35A.
Figure 36:
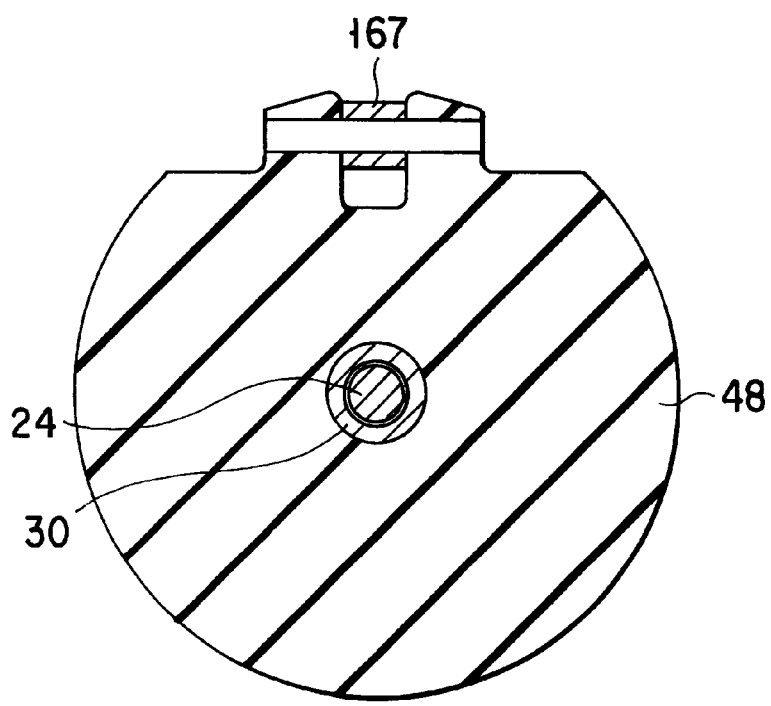
FIG. 36 is a sectional view taken in line S—S in FIG. 35A.

As shown in FIG. 34 (sectional view taken in line R—R in FIG. 33), the fixed handle 76 and the movable handle 77 include a holding mechanism 155 for holding the movable handle 77 in correct assembly position. This holding mechanism 155 includes hemispherical protrusions 156, 156 formed on the sides of the upper part of the movable handle 77 and annular protrusions 157, 157 formed on the inner side of the walls 150, 150 of the fixed handle 76.

Now, the operation of this embodiment will be explained.

In the case where the tool is assembled from the state separated into component parts, the first step is to assemble the treatment section drive unit 27 on the insertion section 3. Specifically, the coupler 27 of the treatment section drive unit 2 is progressively inserted into the sheath 29 from the forward end of the sheath 29, and until the butt surface of the connector 14 comes into contact with the butt surface 30a of the pipe 30, the treatment section drive unit 2 is pushed into the insertion section 3. At this time, the relative positions of the protrusions 16, 16 and the engaging groove 31 and the relative positions of the drive shaft 24 and the protrusions 144, 144 are shown in FIG. 32A. Under this condition, the protrusions 144, 144 are pushed outward by the drive shaft 24, so that the snap fit arms 143, 143 are elastically deformed outward.

From this state, the treatment section drive unit 2 is rotated with respect to the insertion section 3 by holding the holding members 6, 6 of the treatment section drive unit 2. Then, the state as shown in FIG. 32B and FIG. 30 is attained. Under this condition, the protrusions 16, 16 are located on the engaging section 34 of the engaging groove 31, and the butt surface 17 of the protrusion 16, 16 comes into contact with the front surface of the engaging section 34. At the same time, two parallel planes 26, 26 of the drive shaft 24 engage the parallel sections 145, 145 of the protrusions 144, 144 of the rotary engaging member 141. In other words, the treatment section drive unit 2 is rotatably assembled on the insertion section 3.

Next, the insertion section 3 with the treatment section drive unit 2 assembled thereon is assembled on the operating section 5. First, the movable handle 77 is operated in the opening direction to the correct assembly position (the position shown in FIG. 33). In the process, the walls 150, 150 of the fixed handle 76 are elastically deformed sideways, so that the protrusions 156, 156 of the movable handle 77 ride over the protrusions 157, 157 of the fixed handles 76 and engage between the protrusions 157, 157 as shown in FIG. 34. As a result, the movable handle 77 is held in correct assembly position.

Next, as shown in FIG. 33, the rotary engaging member 141 of the insertion section 3 and the coupler 27 of the treatment section drive unit 2 assembled on the insertion section 3 are progressively inserted into the small-diameter section 148 from the large-diameter section 147 of the insertion section holder 146. With the coupler 27 inserted in the inlet hole 89 of the movable handle 77, the insertion section 3 is pushed in further while rotating the movable handle 77 in the closing direction. As a result, the walls 150, 150 of the fixed handle 76 are elastically deformed so that the protrusions 156, 156 are disengaged from the protrusions 157, 157. From this state, the insertion section 3 is pushed in further until the butt surface 158 of the insertion section holder 146 comes into contact with the butt section 142 of the rotary engaging member 141. The coupler 27 comes to engage the engaging section 91. At the same time, the engaging protrusion 113 of the operating section engaging/disengaging member 111 of the insertion section 3 also comes to engage the engaging section 121 of the operating section 5 in the same manner as in the second embodiment, thereby completing the assembly work.

In this assembled state, the snap fit arm 143, which is accommodated in the small-diameter section 148 of the insertion section holder 146, cannot be elastically deformed outward. In other words, the rotation of the treatment section drive unit 2 is kept restricted with respect to the insertion section 3.

Next, the disassembly work will be explained. First, the insertion section 3 with the treatment section drive unit 2 assembled thereon is separated from the operating section 5. In this case, with the movable handle 77 operated in the opening direction up to the position indicated in FIG. 33, the insertion section 3 is separated from the operating section 5 by a technique similar to that in the second embodiment. After that, the treatment section drive unit 2 is separated from the insertion section 3 in the order reverse to the assembly work.

As described above, with the treatment tool for operation according to this embodiment, like the third embodiment, the disassembly and assembly of the component elements can be accomplished easily within a short time. Also, the treatment tool for operation according to this embodiment has no parts difficult to wash and therefore provides a suitable medical equipment requiring a high degree of cleanliness. Especially, the upward rotation of the lever 129 with the treatment section drive unit 2 separated from the insertion section 3 improves the washability of the interior of the insertion section 3.

Further, according to this embodiment, the engagement between the protrusions 153, 153 of the cover 152 and the holes 154, 154 of the walls 150, 150 holds the cover 152 always at the position indicated by solid line in FIG. 29. As a result, the drive shaft 24 of the treatment section drive unit 2 is electrically isolated from the operator. Therefore, the tube 28 is eliminated unlike in the first to third embodiments. Also, according to this embodiment, the neighborhood of the connection groove 88 of the movable handle 77 becomes easy to wash by rotating the cover 152 upward to the position indicated by two-dot chain in FIG. 29.

FIGS. 35A to 37 show a fifth embodiment of the invention. This embodiment is different from the fourth embodiment only in the connection between the insertion section 3 and the operating section 5. Therefore, only the components different from the fourth embodiment will be explained below.

As shown in FIGS. 35A and 35B, the knob 48 is formed with a guide hole 161. Also, the knob 48 has mounted thereon an operating section engaging/disengaging member (engaging/disengaging member) 162 movable along the guide hole 161. This operating section engaging/disengaging member (engaging/disengaging member) 162 is supported on the knob 48 in such a manner as to be movable only in vertical direction in FIG. 35A and FIG. 37 (sectional view taken in line T—T in FIG. 35A).

Figure 37:
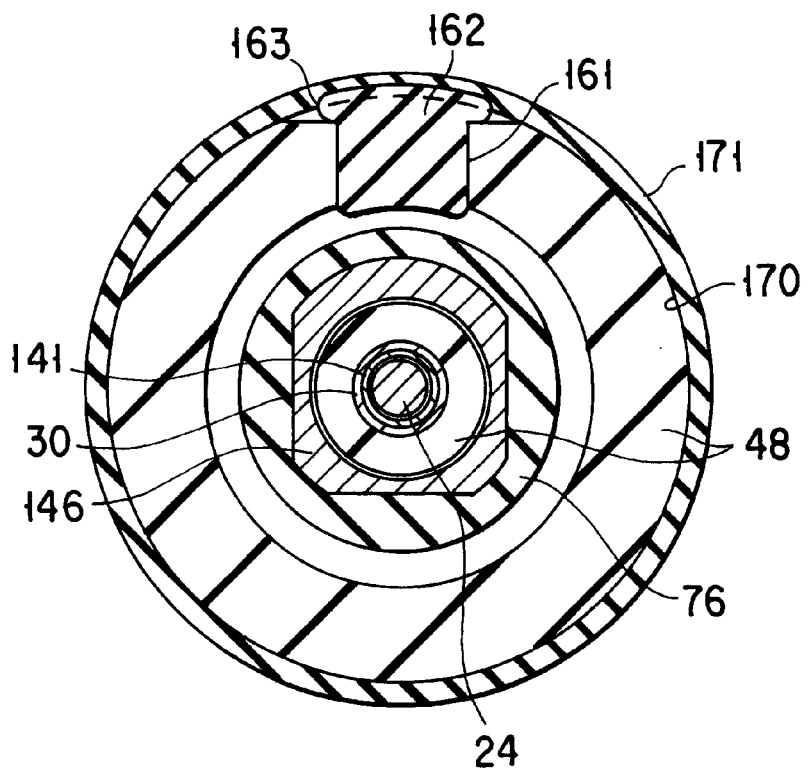
FIG. 37 is a sectional view taken in line T—T in FIG. 35A.
Figure 38:
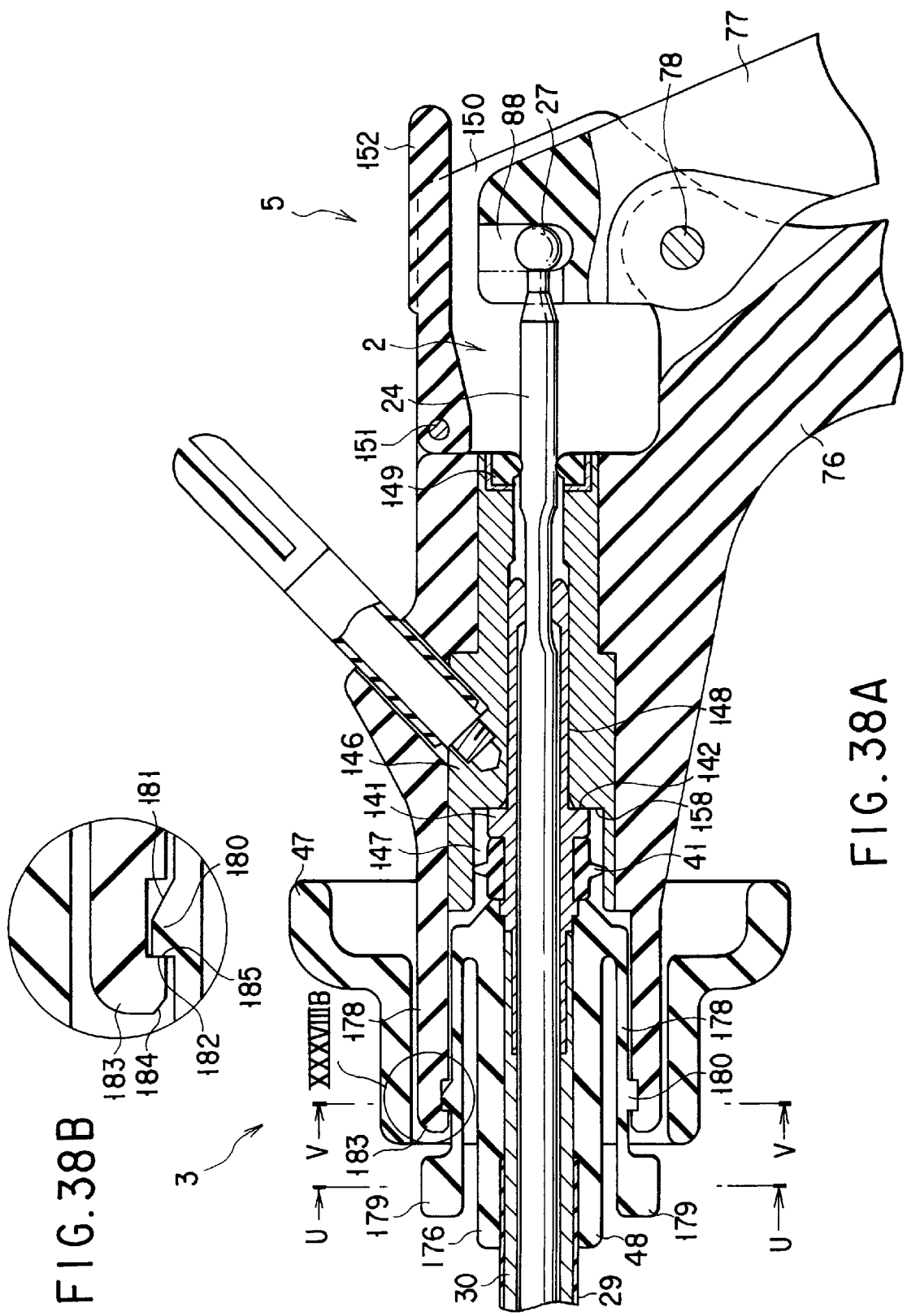
FIG. 38A is a partial sectional view of a treatment tool for operation according to a sixth embodiment of the invention.
FIG. 38B is an enlarged sectional view of a part XXXVIIIB shown in FIG. 38A.

In order to restrict the downward movement of the operating section engaging/disengaging member 162, an end of the operating section engaging/disengaging member 162 is formed with a large-diameter section 163 as shown in FIG. 37. By the way, in the state shown in FIG. 37, the large-diameter section 163 is in contact with the knob 48 and the operating section engaging/disengaging member 162 is located at the lower limit position. As shown in FIGS. 35A and 35B, the other end of the operating section engaging/disengaging member 162 is formed with a slope surface 164 and a butt surface 165. Also, a notch 166 is formed at the intermediate portion of the operating section engaging/disengaging member 162. Also, a lever 167 mounted rotatably on the knob 48 is located forward of the operating section engaging/disengaging member 162. An end of the lever 167 is formed with a pressure section 168 for enabling the operator to operate the tool with his/her fingers. The other end of the lever 167 is formed with an engaging section 169, which is in mesh with the notch 166. A groove 170 is formed in the outer periphery of the knob 48. A rubber ring (biasing means) 171 for pressing the operating section engaging/disengaging member 162 inward (downward in FIG. 35A) is arranged in the groove 170. By the way, the rubber ring 171 is formed of an elastic material such as synthetic rubber.

The upper forward end of the fixed handle 76 is formed with an annular engaging section 172 adapted to engage the operating section engaging/disengaging member 162. The engaging section 172 is formed with a slope surface 173 and a butt surface 174.

Next, the operation of this embodiment will be explained.

In the case where the insertion section 3 is assembled on the operating section 5, the insertion section 3 is pushed into the operating section 5 with the slope surface 164 of the operating section engaging/disengaging member 162 kept in contact with the slope surface 173 of the engaging section 172. As a result, the operating section engaging/disengaging member 162 moves outward (upward in FIG. 35A) by being guided by the guide hole 161 of the knob 48 against the elasticity of the rubber ring 171. Pushing the insertion section 3 further into the operating section 5 causes the operating section engaging/disengaging member 162 to move to the position indicated in FIGS. 35A and 37 by the restitutive power of the rubber ring 171 at the time point when the butt surface 142 of the rotary engaging member 141 comes into contact with the butt surface 158 of the insertion section holder 146. Thus, the butt surface 165 of the operating section engaging/disengaging member 162 comes into contact with the butt surface 174 of the engaging section 172. In other words, the insertion section 3 is completely assembled on the operating section 5.

In the case where the insertion section 3 is separated from the operating section 5, the pressure section 168 of the lever 167 is pushed in (downward in FIG. 35A) thereby to rotate the lever 167. By doing so, the operating section engaging/disengaging member 162 is moved outward (upward in FIG. 35A) by being guided by the guide hole 161 against the elasticity of the rubber ring 171 due to the operation of the engaging section 169 adapted to engage the notch 166. As a result, the operating section engaging/disengaging member 162 disengages from the engaging section 172, and the insertion section 3 becomes separable from the operating section 5. Consequently, the present embodiment can provide a similar effect to the fourth embodiment.

FIGS. 38A to 41 show a sixth embodiment of the invention. This embodiment is different from the fourth embodiment only in the connection between the insertion section 3 and the operating section 5. Therefore, only the component parts different from the fourth embodiment will be explained below.

Figure 39:
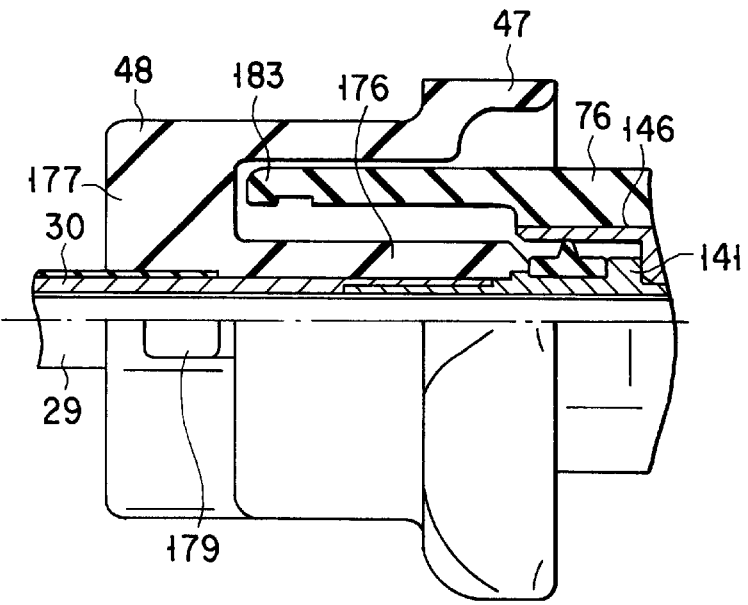
FIG. 39 is a partly-cutaway plan view of the treatment tool for operation shown in FIG. 38A.
Figure 40:
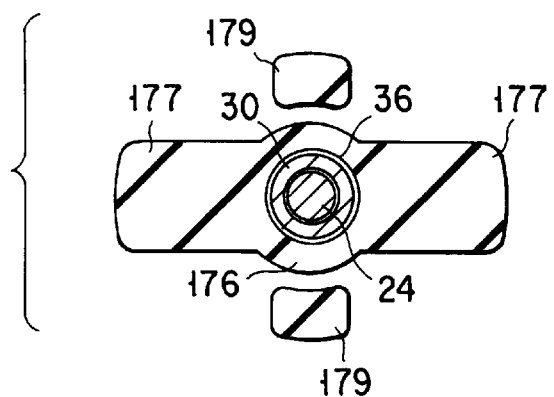
FIG. 40 is a sectional view taken in line U—U in FIG. 38A.
Figure 41:
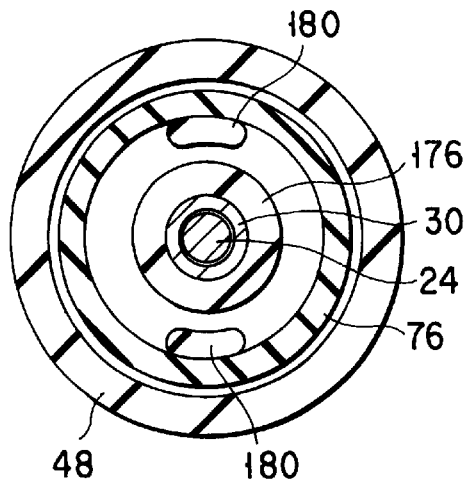
FIG. 41 is a sectional view taken in line V—V in FIG. 38A.

As shown in FIGS. 38A and 38B, the knob 48 is formed with a cylindrical section 176. As shown in FIGS. 39 and 40, two arms 177, 177 extend sideways from the cylindrical section 176. These arms 177, 177 couple the rotary operating section 47 to the cylindrical section 176. Two snap fit arms (biasing means) of cantilever type 178, 178 extend forward from the base end side of the cylindrical section 176. The outer peripheral surface at the forward end of each snap fit arm 178 is formed with a pressure section 179 for enabling the operator to operate the tool with his/her fingers. Also, a protrusion (engaging/disengaging member) 180 is projected from the outer peripheral surface of each snap fit arm 178 at a position rearward of the pressure section 179. This protrusion 180 is formed with a slope surface 181 and a butt surface 182.

The forward end of the upper portion of the fixed handle 76 is formed with an annular engaging section 183 adapted to engage the protrusions 180, 180. The engaging section 183 is formed with a slope surface 184 and a butt surface 185.

Now, the operation of this embodiment will be explained.

In the case where the insertion section 3 and the operating section 5 are assembled, the insertion section 3 is pushed into the operating section 5 with the slope surface 181 of each protrusion 180 kept in contact with the slope surface 184 of the engaging section 183. As a result, each snap fit arm 178 is elastically deformed inward so that each protrusion 180 is moved inward. When the insertion section 3 is further pushed in under this state, the protrusions 180, 180 move to the position indicated in FIGS. 38A and 38B at the time point when the butt surface 142 of the rotary engaging member 141 comes into contact with the butt surface 158 of the insertion section holder 146. Thus, the elastic deformation of each snap fit arm 178 is relaxed. At the same time, the butt surface 182 of the protrusion 180 and the butt surface 185 of the engaging section 183 come into contact with each other. In other words, the insertion section 3 is completely assembled on the operating section 5.

In separating the insertion section 3 from the operating section 5, the pressure section 179 of each snap fit arm 178 is pushed in to elastically deform each snap fit arm 178 inward, thereby moving each protrusion 180 inward. As a result, each protrusion 180 and the engaging section 183 disengage from each other, thus making it possible to separate the insertion section 3 from the operating section 5. Consequently, this embodiment has a similar effect to the fourth embodiment.

Figure 42:
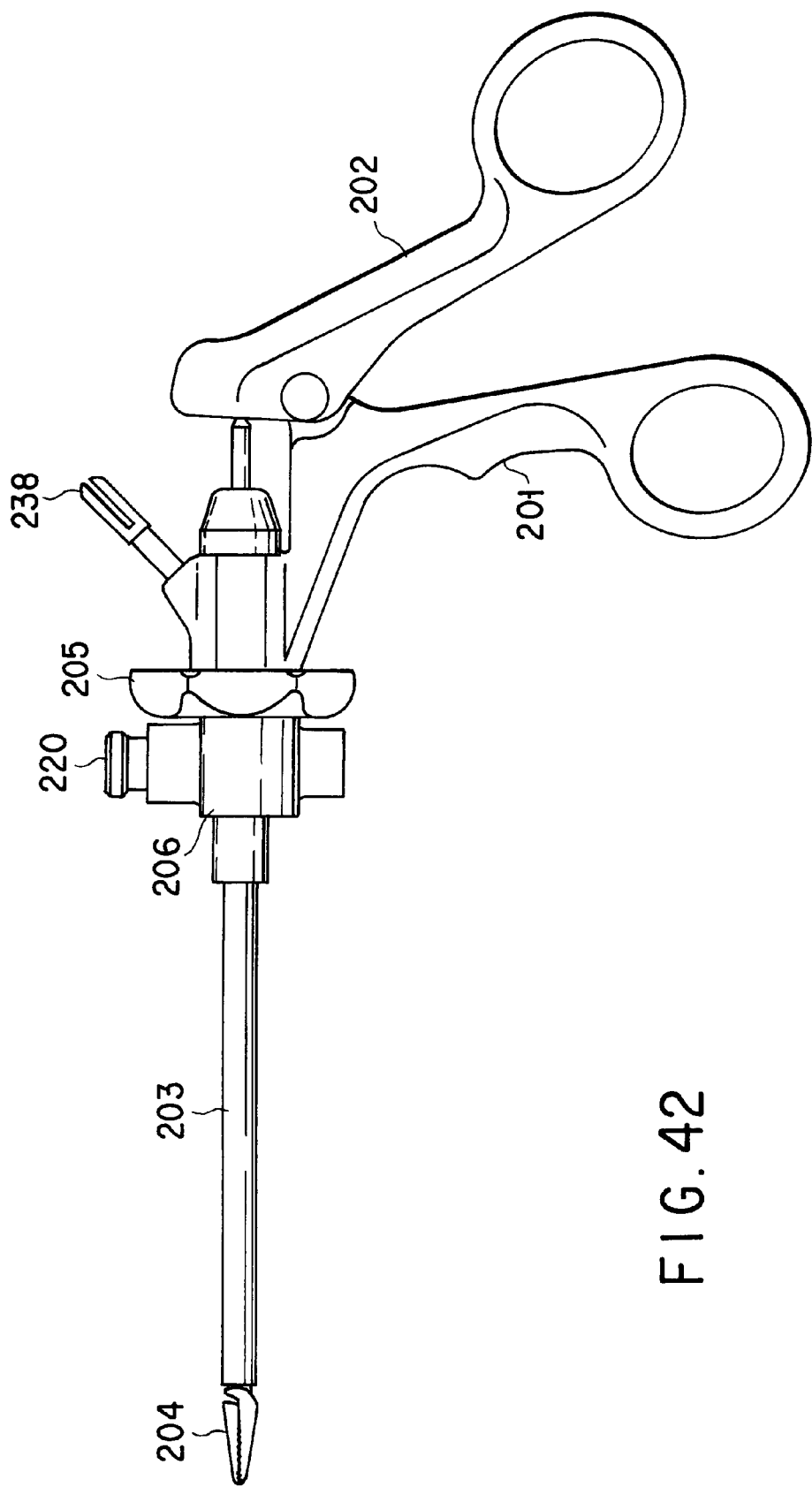
FIG. 42 is a side view of a treatment tool for operation according to a seventh embodiment of the invention.

FIGS. 42 to 47F show a seventh embodiment of the invention. As shown in FIG. 42, the treatment tool for operation according to this embodiment comprises a sheath unit having an insertion section 203, a treatment section drive unit mounted on the sheath unit and having a treatment member 204, and an operating body having a fixed operating section 201 and a movable operation section 202 connected openably (rotatably) to the fixed operating section 201. The insertion section 203 includes a rotary knob 205 and an operating section 206 for disassembly and assembly. Also, the operating section 206 is provided with a pin 238 for connection to a high-frequency current cord.

Figure 43A:
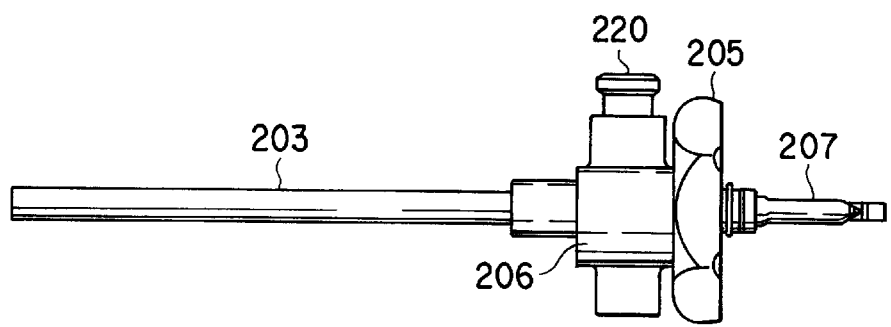
FIG. 43A is a side view of the sheath unit.
Figure 43B:
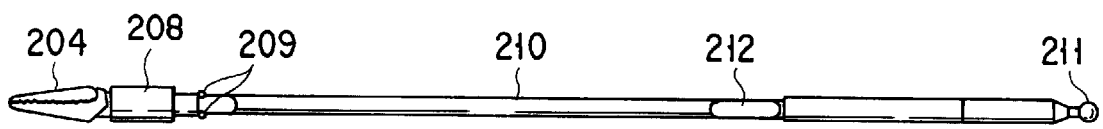
FIG. 43B is a side view of the treatment section drive unit.

FIG. 43A shows a sheath unit. As shown, the base end of the insertion section 203 is provided with a first connector 207 connected to the fixed operating section 201. FIG. 43B shows a treatment section drive unit. As shown, the treatment section drive unit includes a treatment member 204, a treatment member holder 208 and an operating shaft 210 connected to the treatment member 204. The treatment member 204 includes a pair of holding sections, which are connected to the treatment member holder 208 in such a manner that at least one of the holding members can be opened or closed. The base end of the treatment member holder 208 is provided with a second connector 209 connected to the sheath unit. A third connector 211 connected to the movable operating section 202 is arranged at the base end of the operating shaft 210. Also, the operating shaft 210 has a rotary engaging member 212 adapted to engage the sheath unit forward of the third connector 211. By the way, the treatment member 204, though shaped suitably for holding the tissue, is not limited to the shown shape but can assume another shape such as scissors.

Figure 43C:
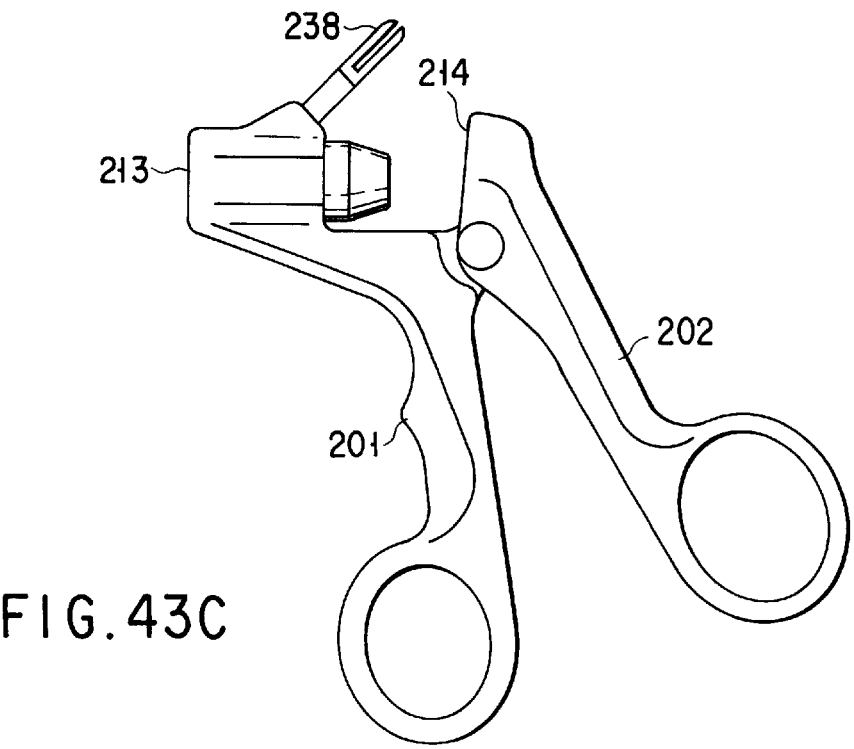
FIG. 43C is a side view of the operating section.

FIG. 43C shows an operating body. As shown, the fixed operating section 201 includes a first holder 213 adapted to engage the first connector 207 of the sheath unit and a second holder 214 combined with the third connector 211 of the treatment section drive unit.

Figure 44A:
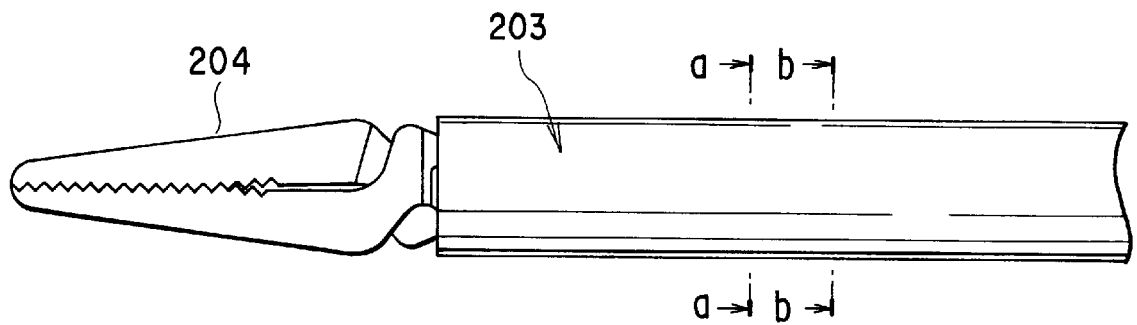
FIG. 44A is a diagram showing the forward end of the sheath unit.

FIG. 44A shows a sectional view of the forward end of the sheath unit. As shown, the insertion section 203 is configured of a pipe 215 and an outer pipe 216 made of an insulating material covered on the outer periphery of the pipe 215. The pipe 215 includes a third holder 217 combined with the treatment member holder 208 of the treatment section drive unit. This third holder 217 includes a first groove 218 extending axially of the insertion section 203 and a second groove 219 extending along the periphery of the insertion section 203.

Figure 44B:
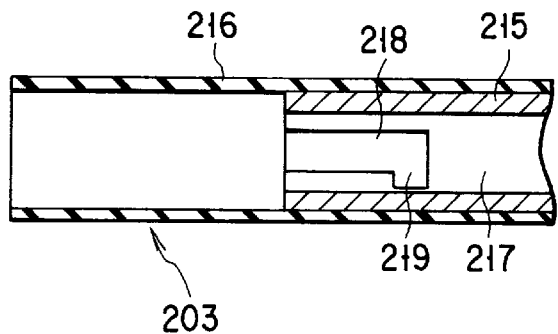
FIG. 44B is a sectional view of the unit shown in FIG. 44A.
Figure 44C:
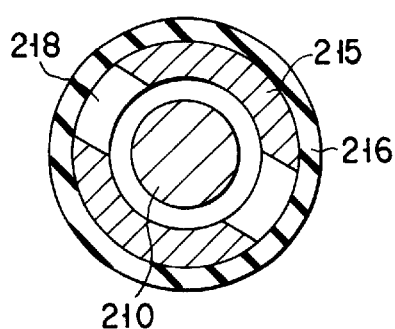
FIG. 44C is a sectional view taken in line a—a in FIG. 44A.
Figure 44D:
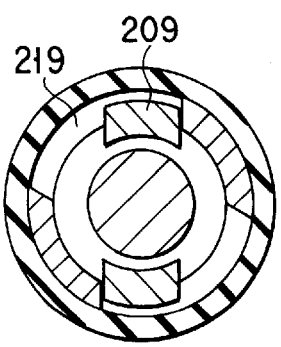
FIG. 44D is a sectional view taken in line b—b in FIG. 44A.

Sectional views of the insertion section 203 with the treatment tool for operation according to this embodiment in assembled state are shown in FIG. 44B (sectional view taken in line a—a in FIG. 44A) and FIG. 44C (sectional view taken in line b—b in FIG. 44A). In the assembled state, the second connector 209 engages the second groove 219 (see FIG. 44C) but not the first groove 218 (see FIG. 44B).

Figure 45A:
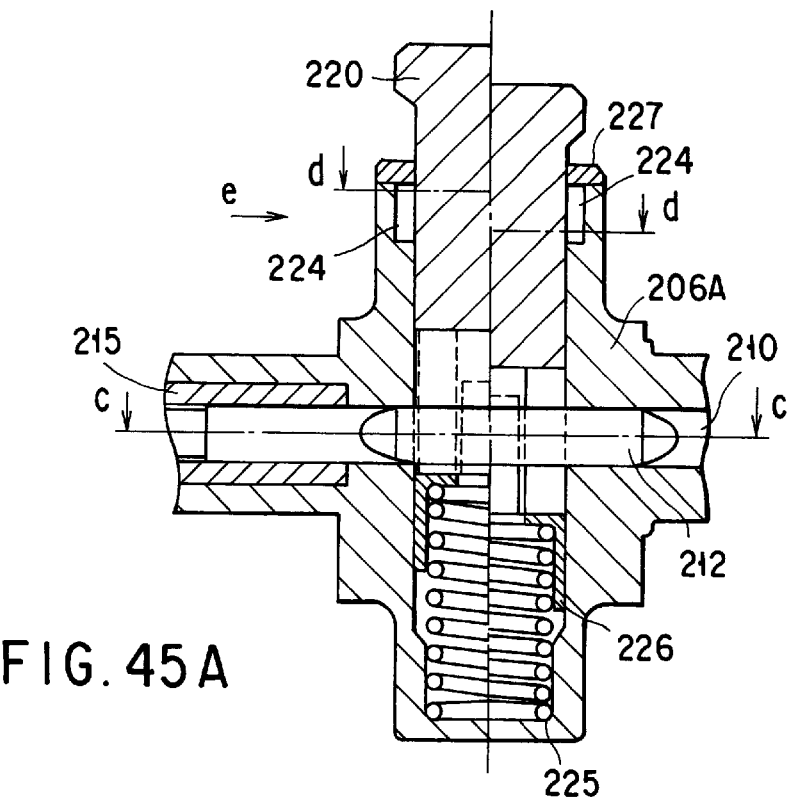
FIG. 45A is a sectional view of the rear end of the sheath unit.
Figure 45B:
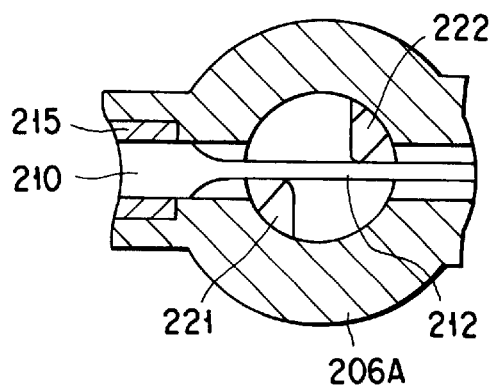
FIG. 45B is a sectional view taken in line c—c in FIG. 45A.

FIG. 45A shows a sectional view of the base end of the sheath unit. A button 220 is inserted in a housing 206A of the operating section 206. This button 220 is movable in the direction perpendicular to the length of the insertion section 203. As shown in FIG. 45B (sectional view taken in line c—c of FIG. 45A) and FIGS. 46A to 46D, the button 220 includes a first leg 221 and a second leg 222.

Figure 45C:
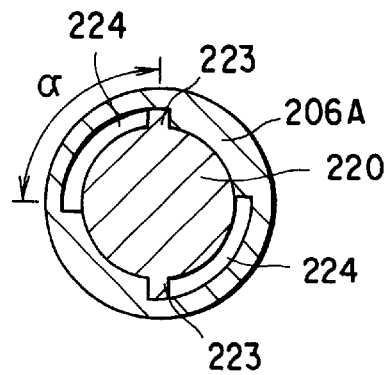
FIG. 45C is a sectional view taken in line d—d in FIG. 45A.
Figure 45D:
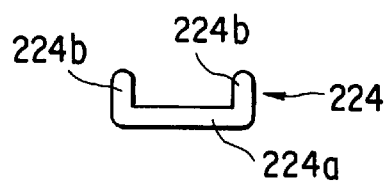
FIG. 45D is a view taken along the direction of arrow e in FIG. 45A.

As shown in FIG. 45C (sectional view taken in line d—d in FIG. 45A), a pin 223 is protruded from the button 220. This pin 223 engages the third groove 224 formed in the inner peripheral surface of the housing 206. In the drawing, a designates the rotational angle of the button 220. FIG. 45D (view along the direction of arrow e in FIG. 45A) shows the shape of the third groove 224.

As shown in FIG. 45A, the button 220 is urged upward by a spring 225. Also, the housing 206A has a holding section 227 for restricting the upward movement of the button 220. By the way, although the spring 225 directly presses the button 220 in the drawing, an intermediate member 226 can be inserted between the spring 225 and the button 220 so that the biasing force of the spring 225 may be exerted on the button 220 through the intermediate member 226.

As shown in FIG. 45B, according to this embodiment, as the rotary engaging member 212 of the treatment section drive unit is engaged between the legs 221 and 222 of the button 220, the rotation of the treatment section drive unit with respect to the sheath unit is restricted. By the way, in this case, the rotary engaging member 212 has a parallel portion sandwiched between the first leg 221 and the second leg 222.

FIG. 46 shows the button 220 in detail. When the button 220 rotates by α° (see FIG. 45C), the distance between the first leg 221 and the second leg 222 changes from L (state of FIG. 46A) to I (state of FIG. 46B). In the case where the distance between the first leg 221 and the second leg 222 is set to L, the third connector 211 of the treatment section drive unit is capable of passing between the first left 221 and the second leg 222. In the case where the distance between the legs 221 and 222 is set to I, on the other hand, the distance between the legs 221 and 222 is substantially equal to the width of the parallel section of the rotary engaging member 212 of the treatment section drive unit. Specifically, the second leg 222 is formed in steps. Thus, the second leg 222 is formed with a long portion 222A having a height H and a short portion 222B having a height h. According to this embodiment, with the rotation of the button 220 to the state shown in FIG. 46A, the distance between the long portion 222A and the first leg 221 is set to L in the range of the height (H–h) from the end of the long portion 222A to the end of the short portion 222B. Therefore, the third connector 211 can pass between the legs 221 and 222 in the range of height (H–h). Although the distance L is fixed over the entire range of height (H–h) in the drawing, the distance between the legs 221 and 222 is not necessarily fixed in the range of height (H–h) if the third connector 211 can pass between the legs 221 and 222 in the state of FIG. 46A.

Figure 46A:
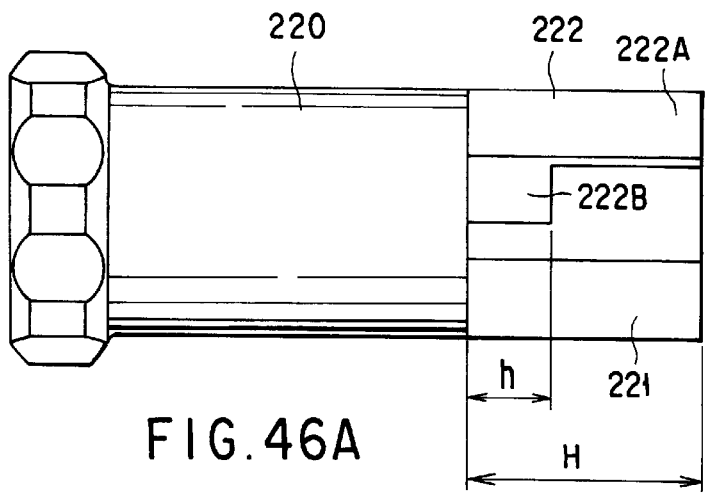
FIGS. 46A and 46C are side views of the button of the treatment tool for operation of FIG. 42.
Figure 46B:
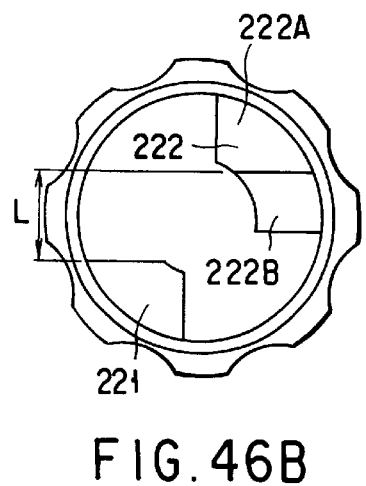
FIGS. 46B and 46D are front views of the button of the treatment tool for operation of FIG. 42.
Figure 46C:
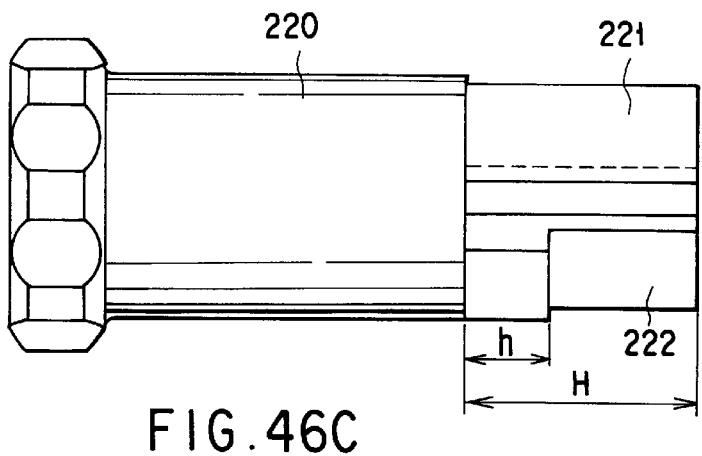
Figure 46D:
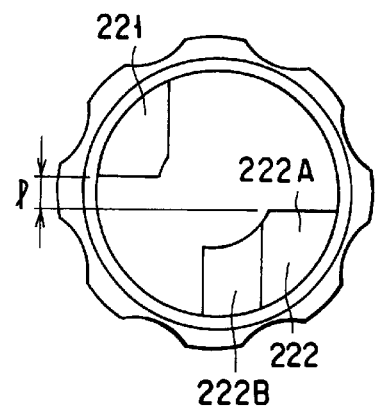
Figure 49:
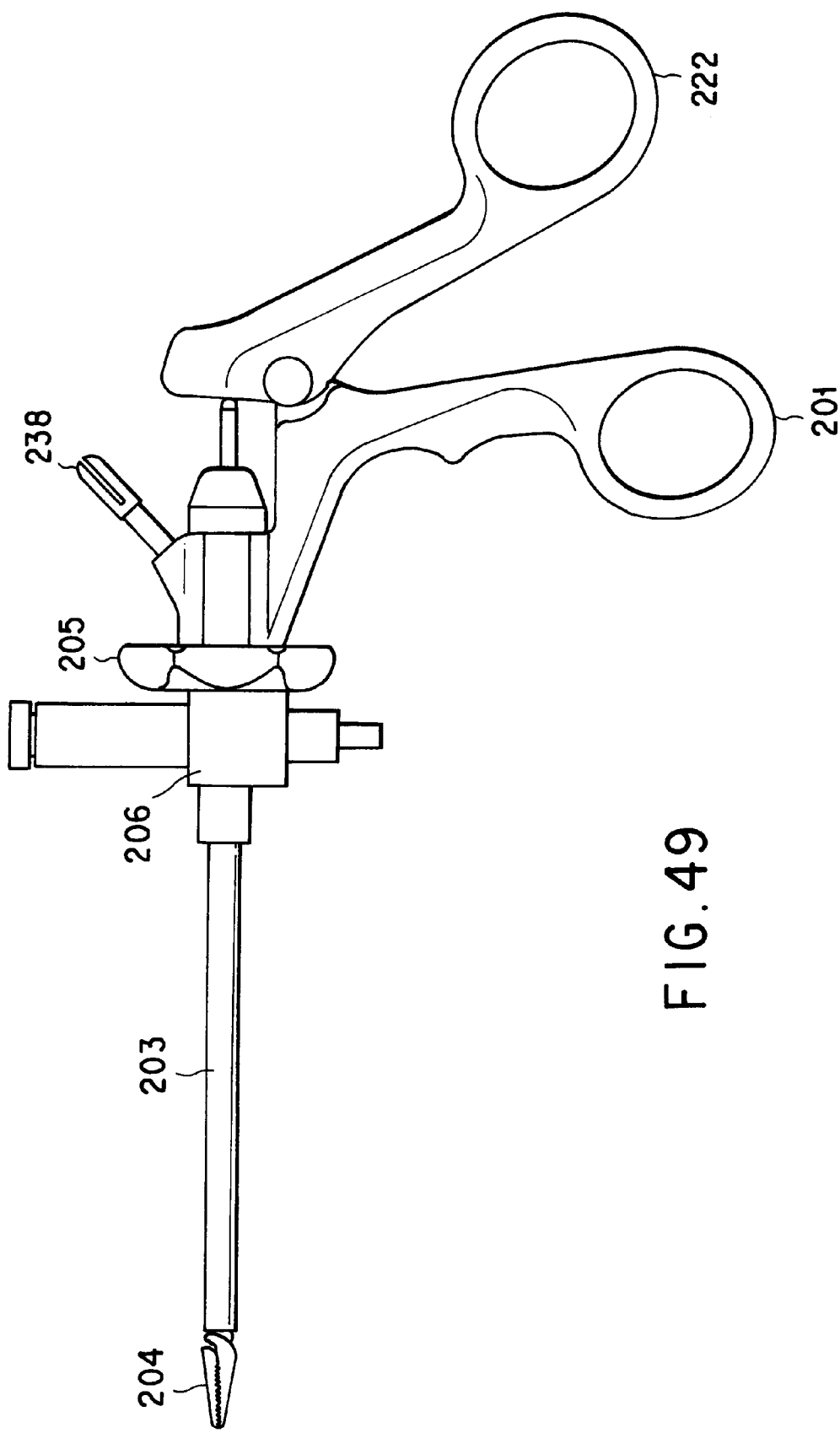
FIG. 49 is a side view of a treatment tool for operation according to a ninth embodiment of the invention.
Figure 50A:
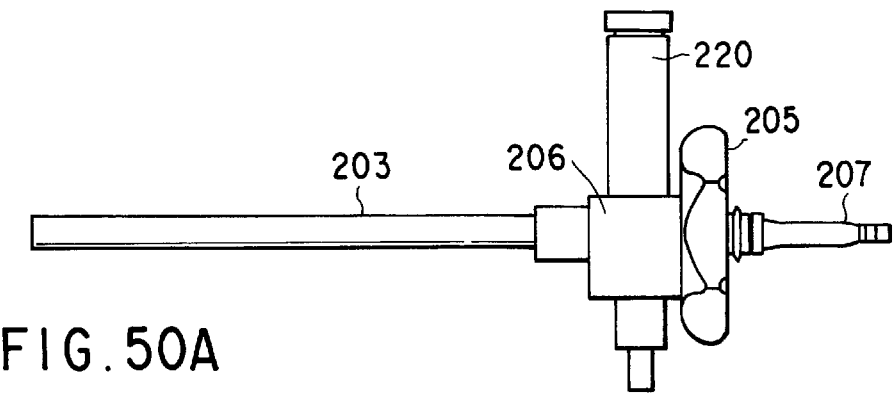
FIG. 50A is a side view of the sheath unit constituting the operating treatment unit of FIG. 49.
Figure 50B:
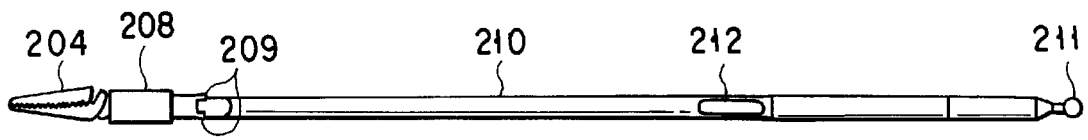
FIG. 50B is a side view of the treatment section drive unit constituting the treatment tool for operation of FIG. 49.
Figure 50C:
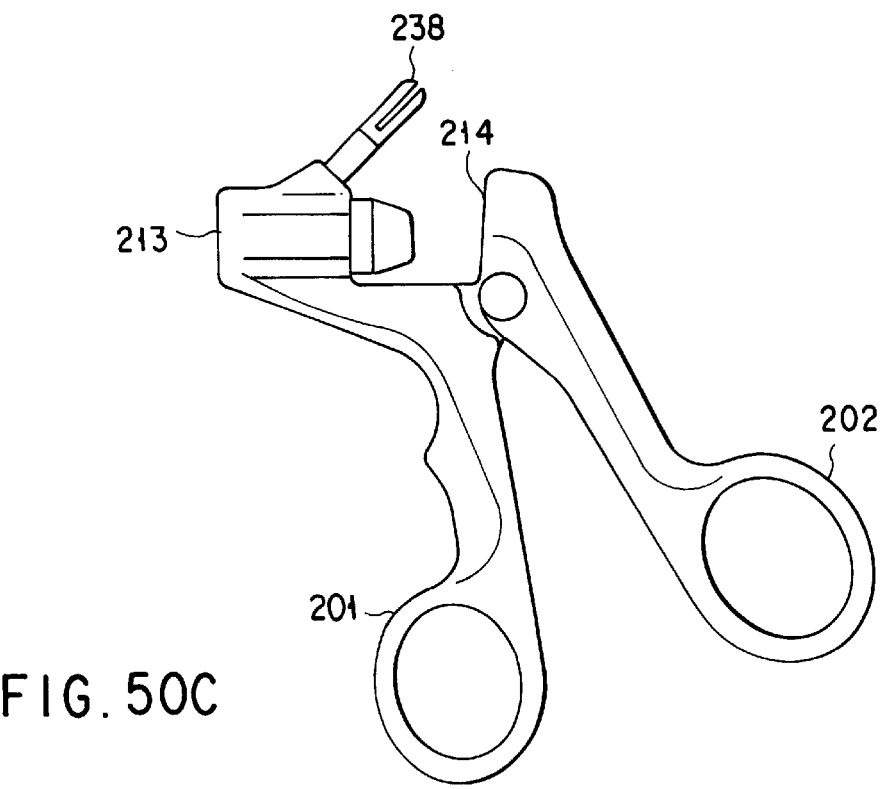
FIG. 50C is a side view of the operating section constituting the treatment tool for operation of FIG. 49.
Figure 51A:
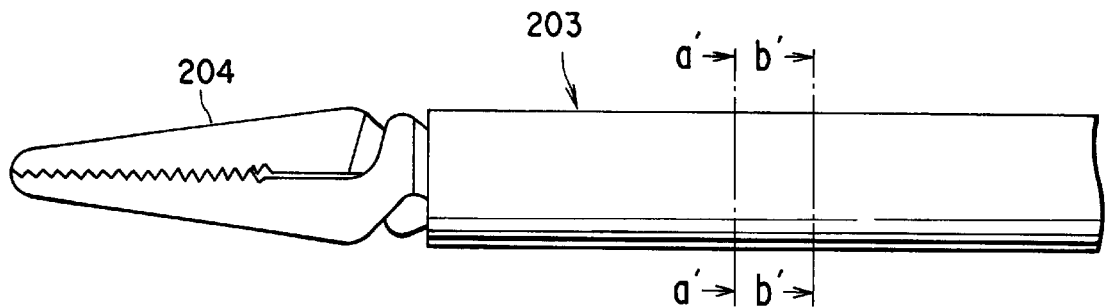
FIG. 51A is a side view of the forward end side of the treatment tool for operation of FIG. 49.
Figure 51B:
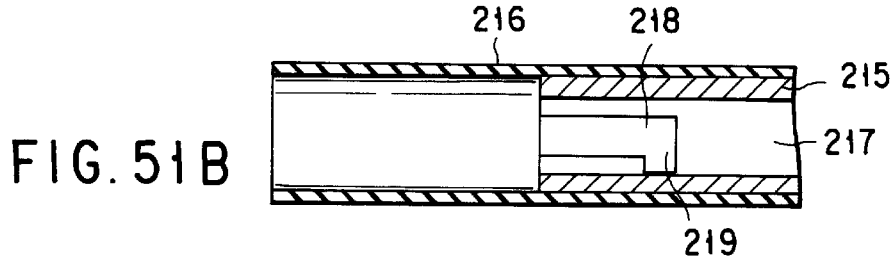
FIG. 51B is a sectional view of the tool shown in FIG. 51A.
Figure 51C:
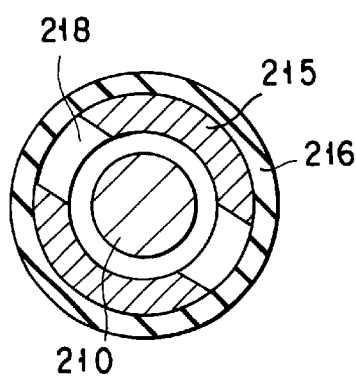
FIG. 51C is a sectional view taken in line a'—a' in FIG. 51A.
Figure 51D:
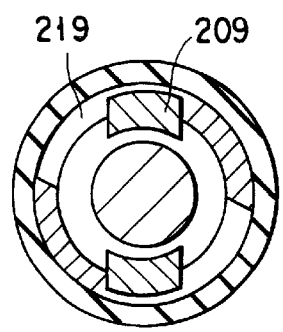
FIG. 51D is a sectional view taken in line b'—b' in FIG. 51A.

Also, according to this embodiment, with the rotation of the button 220 to the state shown in FIG. 46B, the distance between the long portion 222A and the first leg 221 is set to 1. In this case, the width of the second leg 222 is such that the range of height h is larger than the range of height (H–h). The distance between the legs 221 and 222 is always constant (=1) over the entire range of height H.

By the way, although the first leg 221 and the second leg 222 are cut out integrally from the button 220 according to this embodiment, the first leg 221 and the second leg 222 can be formed with pins independent of the button 220 as in the eighth embodiment described later.

Next, a method of assembling the treatment tool for operation according to this embodiment will be explained. First, upon insertion of the sheath unit into the operating body, the first connector 207 holds the sheath unit rotatably on the fixed operating section 201. Under this condition, the turning of the rotary knob 205 causes the insertion section 203 to rotate. Then, when the treatment section drive unit is inserted into the sheath unit, the third connector 211 of the treatment section drive unit is connected to the holder 214 of the movable operating section 202, while at the same time inserting the second connector 209 of the treatment drive unit into the third holder 217 of the sheath unit. At this time, the second connector 209 is inserted to such an extent as to reach the connector of the first groove 218 and the second groove 219. Under this condition, the rotation by pushing the button 220 causes the rotation of the rotary engaging member 212 of the treatment section drive unit, so that the second connector 209 engages the second groove 219. As a result, the axial movement of the treatment section drive unit with respect to the sheath unit is restricted. Also, the parallel section of the rotary engaging member 212 is engaged between the first leg 221 and the second leg 222 of the button 220, and the rotation of the treatment section drive unit with respect to the sheath unit is restricted. This series of operation will be described in detail below.

FIGS. 47A to 47E show stages of engagement between the legs 221, 222 of the button 220 and the rotary engaging member 212 of the operating shaft 210. FIG. 47A shows the state in which the first leg 221 and the second leg 222 are in contact with the upper and lower sides of the rotary engaging member 212. Under this condition, the second connector 209 of the treatment section drive unit is located at the connector (intersection) of the first groove 218 and the second groove 219 at the forward end of the sheath unit. Also, the treatment section drive unit is rotatable.

With the rotation of the button 220 from this state along the lateral path 224a (see FIG. 45A) of the third groove 224 in the direction of arrow in FIG. 47A, the rotary engaging member 212 develops a couple of forces and rotates the treatment section drive unit. As a result, the parallel section of the rotary engaging member 212 is sandwiched between the legs 221 and 222 as shown in FIG. 47B, thereby restricting the rotation of the treatment section drive unit. Also, in the state of FIG. 47B, the second connector 209 of the treatment section drive unit engages the second groove 219 and thus the movement of the treatment section drive unit along the axis is restricted. In other words, the movement of the treatment section drive unit is restricted in both axial direction and rotational direction.

FIG. 47C shows the state with the button 220 moved upward from the state of FIG. 47B, in which the rotation of the button 220 is restricted by causing the pin 223 of the button 220 to engage the longitudinal path 224b of the third groove 224.

The above-mentioned operation makes it possible to assemble the treatment section drive unit, the sheath unit and the operating body.

Now, a method of disassembling the treatment tool for operation according to this embodiment will be explained.

From the state of FIG. 47C, the button 220 is pushed down and rotated in the direction opposite to that for the assembly work. This rotation of the button 220 rotates the rotary engaging member 212, so that the second connector 209 moves from the position engaging the second groove 219 to the intersection between the first groove 218 and the second groove 219.

FIG. 47D shows the state in which the button 220 is pushed down and rotated along the direction of arrow from the assembled state shown in FIG. 47C. Under this condition, the short portion 222B of the second leg 222 comes in contact with the rotary engaging member 212. From this state, the button 220 is further rotated along the lateral path 224a of the third groove 224 in the direction of arrow. Then, a couple of forces develops in the rotary engaging member 212 thereby to rotate the treatment section drive unit.

FIG. 47E shows the state in which the rotary engaging member 212 is rotated by the short portion 222B of the second leg 222. In the process, the second connector 209 of the treatment section drive unit is located in the first groove 218 of the sheath unit. FIG. 47F shows the state in which the button 220 is pushed up along the longitudinal path 224b of the third groove 224 from the state of FIG. 47E. Under this condition, the rotation of the button 220 is restricted and the treatment section drive unit can move in both rotational direction and axial direction. After that, the treatment section drive unit is pulled off from the sheath unit which in turn is pulled off from the operating section.

As described above, according to this embodiment, the operating section, the sheath unit and the treatment section drive unit can be easily disassembled or assembled for an improved washability and sterilization. Also, the treatment section drive unit can be fixed and relaxed simply by operating the button 220. Therefore, the disassembly and assembly work can be very easily performed simply by operating the operator's side of the operating section and the insertion section.

FIGS. 48A to 48D show an eighth embodiment of the invention. This embodiment is different from the seventh embodiment only in the shape of the button 228.

As shown in FIGS. 48A to 48D, the button 228 includes a third leg 229, a fourth leg 230 and a fifth leg 231. These legs 229, 230, 231 are composed of pins and mounted on the body of the button 228. By the way, the third leg 229 corresponds to the first leg 221 of the seventh embodiment, and the fourth leg 230 and the fifth leg 231 correspond to the second leg 222 of the seventh embodiment.

The operation of this embodiment is the same as that of the seventh embodiment, and so is the basic effect. The effect unique to the present embodiment not found in the seventh embodiment is that the pins 229, 230, 231 are physically independent of the body of the button 220, and therefore can be easily machined. In contrast, the button 220 of the seventh embodiment is complicated in shape and difficult to machine.

FIGS. 49 to 52D show a ninth embodiment of the invention. The treatment tool for operation according to this embodiment has the same fundamental configuration as the seventh embodiment. Consequently, only those components different from the seventh embodiment will be explained below, while the common components are designated by the same reference numerals, respectively, and will not be described.

FIGS. 52A to 52D show sectional views of the base end of the sheath unit. The button 220 is movably inserted in the housing 206A of the operating section 206 in the direction at right angles to the length of the insertion section 203. The state before the button 220 is depressed is shown on the left side of FIG. 52A, and the state after the button 220 is depressed on the right side of FIG. 52A. The button 220 is formed with a slit 221. As shown in detail in FIG. 52C, the slit 221 includes a parallel section 222 in which the rotary engaging member 212 of the operating shaft 210 is fitted, a circular section 223 having a size sufficient to allow the third connector 211 of the treatment section drive unit to pass therethrough, and a shoulder 224 for pushing the rotary engaging member 212. Also, the button 220 includes O-rings 225, 226 for holding the hermetic state of the sliding surface of the button 220.

Next, a method of assembling the treatment tool for operation according to this embodiment will be explained.

First, upon insertion of the sheath unit into the operating body, the first connector 207 holds the sheath unit rotatably on the fixed operating section 201. When the rotary knob 205 is turned under this condition, the insertion section 203 is also turned. Then, upon insertion of the treatment section drive unit into the sheath unit, the third connector 211 of the treatment section drive unit is connected to the holder 214 of the movable operating section 202, while at the same time the second connector 209 of the treatment section drive unit is inserted into the third holder 217 of the sheath unit. At this time, the second connector 209 is inserted to reach the connector of the first groove 218 and the second groove 219.

Under this condition, the button 220 is pushed in. The rotary engaging member 212 of the operating shaft 210 is rotated by being pushed by the shoulder 224 of the slit 221, and fitted in the parallel section 222 of the slit 221. By doing so, the rotation of the treatment section drive unit is restricted. Also, at this time, the rotation of the treatment section drive unit causes the second connector 209 to engage the second groove 219 thereby restricting the movement of the treatment section drive unit in the direction along the axis.

Figure 52A:
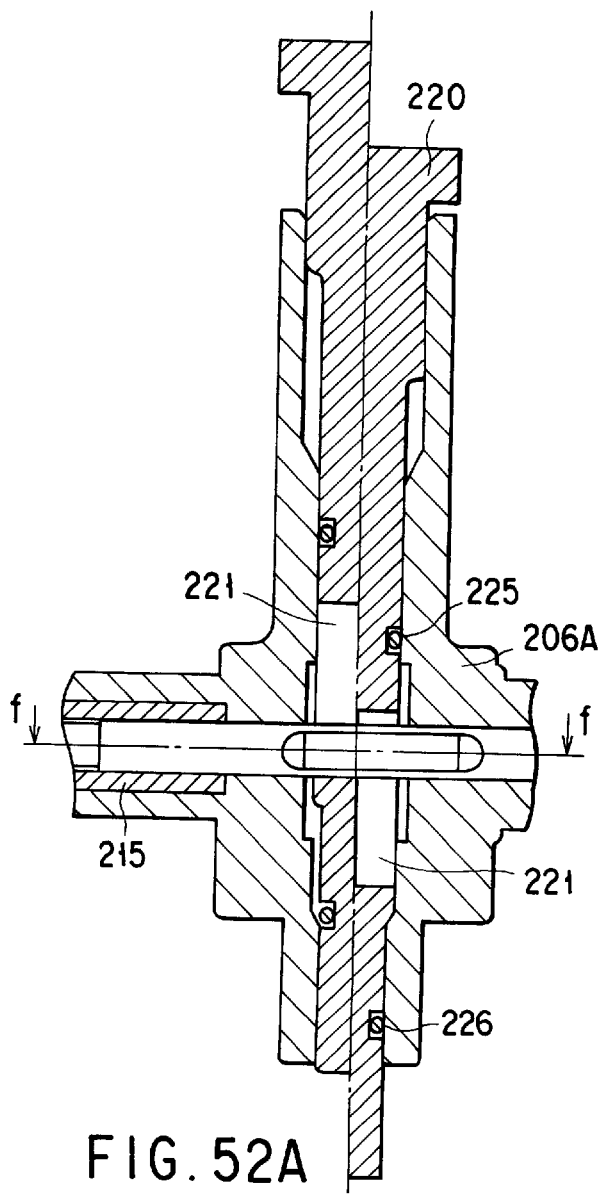
FIG. 52A is a sectional view of this side of the treatment tool for operation of FIG. 49.
Figure 52B:
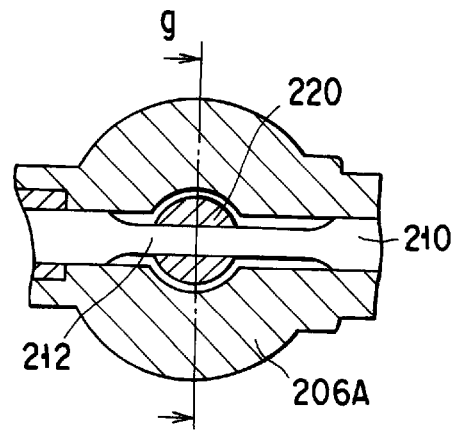
FIG. 52B is a sectional view taken in line f—f in FIG. 52A.
Figure 52C:
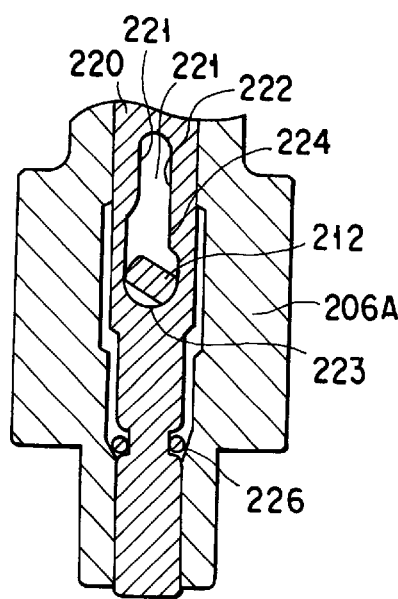
FIG. 52C is a sectional view taken in line g—g in FIG. 52B.
Figure 52D:
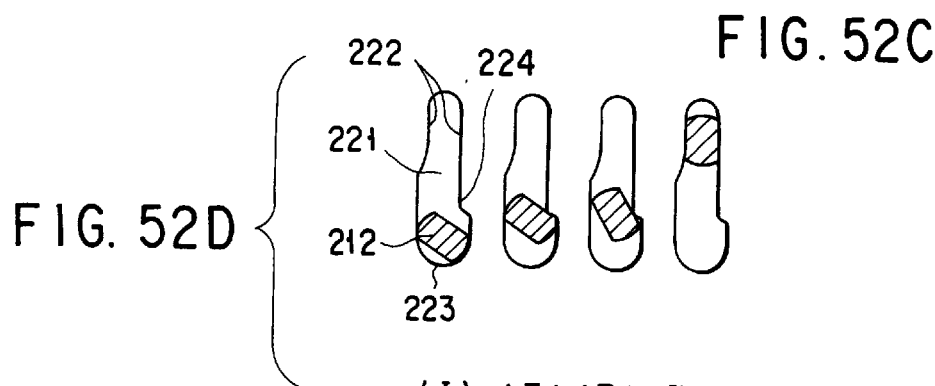
FIG. 52D is a diagram showing the operation of the button and the rotary engaging member of the operating shaft.

FIG. 52D shows the relative positions of the slit 221 and the rotary engaging member 212. In FIG. 52D, (I) designates the state before the button 220 is depressed. Under this condition, the rotary engaging member 212 is located at the circular section 223 of the slit 221 and can freely pass through the slit 221. (II) shows the state in which the button 220 is pushed and the shoulder 224 of the slit 221 has come into contact with the rotary engaging member 212. (III) shows the state in which the button 220 is pushed further downward from the state of (II) thereby to rotate the rotary engaging member 212. By the way, in this case, the portions of the slit 221 other than the shoulder 224 do not interfere with the rotary engaging member 212. (IV) shows the state in which the rotary engaging member 212 enters the parallel section 222 of the slit 221 and thereby restricts the rotation of the rotary engaging member 212.

The above-mentioned operation completes the assembly of the treatment section drive unit, the sheath unit and the operating section.

Now, a method of disassembling the treatment tool for operation according to this embodiment will be explained.

First, the button 220 is pulled up from the state (IV) of FIG. 52D, and the rotary engaging member 212 is located at the circular section 223 of the slit 221. Under this condition, the rotational direction of the rotary engaging member 212 is not limited, and therefore the rotary engaging member 212 can be rotated freely. Now, under this condition, the second connector 209 is moved to the intersection between the second groove 219 and the first groove 218 by rotating the treatment section drive unit by holding the treatment member 204. By doing so, the fixed state of the treatment section drive unit along the axial direction is released.

The above-mentioned operation can release the fixed state of the treatment section drive unit in rotational direction and axial direction. As a consequence, under this condition, the treatment section drive unit is pulled off from the sheath unit, which in turn is pulled off from the operating section, thus completing the disassembly work.

As described above, according to this embodiment, the operating section, the sheath unit and the treatment section drive unit can be easily disassembled and assembled for an improved washability and sterilization. Also, since the treatment section drive unit can be fixed simply by operating the button 220 at the time of assembly, the assembly operation is simple.

FIGS. 53 to 55B shows a tenth embodiment of the invention. The treatment tool for operation according to this embodiment has the same configuration as the ninth embodiment except for the operating section 227.

Figure 53:
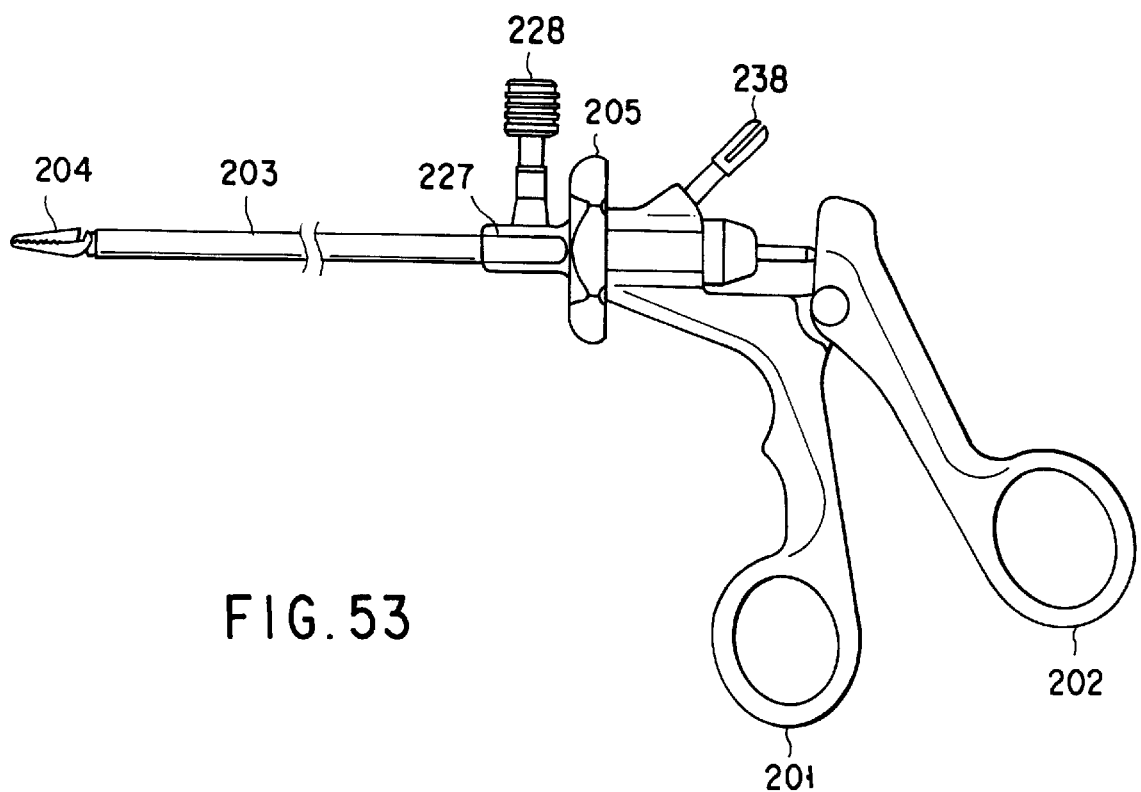
FIG. 53 is a side view of a treatment tool for operation according to a tenth embodiment of the invention.

As shown in FIG. 53, a rotary fixing member 228 is removably mounted at the base end side of the sheath unit. As shown in detail in FIGS. 54D and 55B, the rotary fixing member 228 includes a first leg 229 and a second leg 230. Also, the first leg 229 and the second leg 230 have different lengths. The rotary fixing member 228 is inserted from the opening formed in the operating section 227, and engages the rotary engaging member 212 of the operating shaft 210 thereby to restrict the rotation of the treatment section operating unit.

Figure 55A:
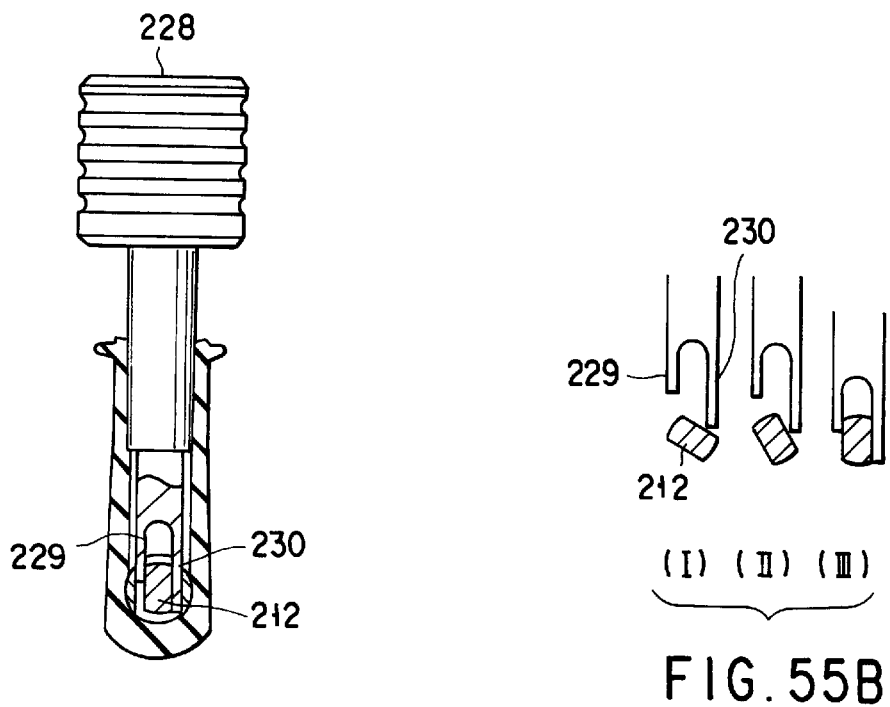
FIG. 55A is a sectional view of the base end of the treatment section of the treatment tool for operation of FIG. 53.
Figure 55B:
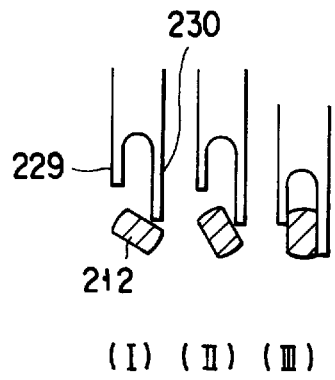
FIG. 55B is a diagram showing the operation of the rotary fixing member and the rotary engaging member of the operating shaft.

(I) of FIG. 55B shows the state in which the rotary fixing member 228 is pushed in downward so that the second leg 230 is in contact with the rotary engaging member 212. (II) shows the state in which the rotary fixing member 228 is pushed in further downward from the state of (I) to such an extent that the rotary engaging member 212 is rotated by the second leg 230. By the way, the length of the first leg 229 is set in such a manner as not to interfere with the rotary engaging member 212 under this state (II). (III) shows the state in which the rotary engaging member 212 is sandwiched between the first leg 229 and the second leg 230 to restrict the rotary engaging member 212. By the way, the length of the first leg 229 is set so that the first leg 229 can contact the parallel section of the rotary engaging member 212 under the state (III).

As described above, according to this embodiment, the operating section, the sheath unit and the treatment section drive unit can be easily disassembled and assembled. Thus the washability and sterilization are improved. Also, the assembly operation is simplified in view of the fact that the treatment section drive unit can be fixed at the time of assembly work simply by operating the rotary fixing member 228.

FIGS. 56 to 60 show a 11th embodiment of the invention. The treatment tool for operation according to this embodiment has the same configuration as that of the tenth embodiment except for the operating section 231.

Figure 56:
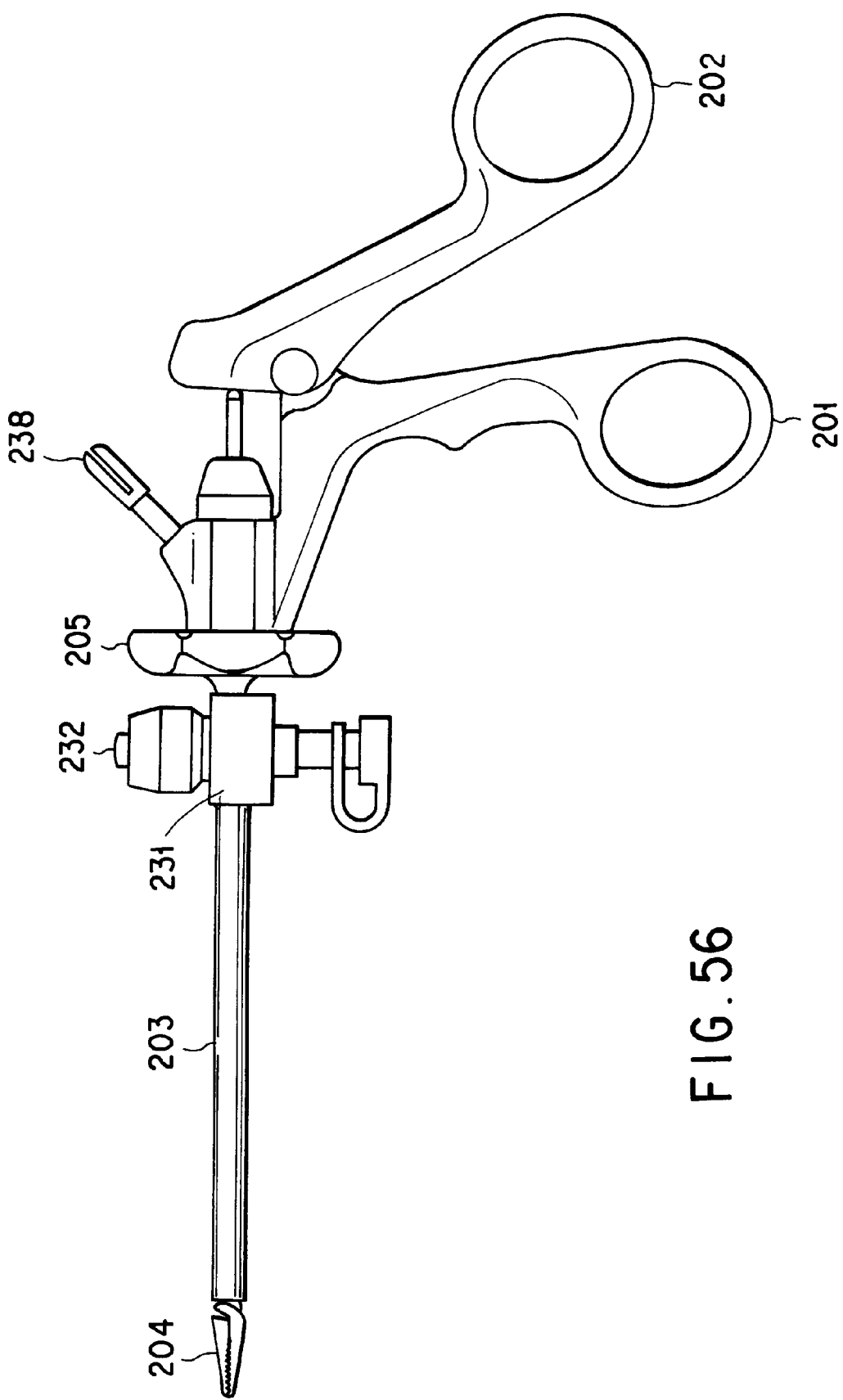
FIG. 56 is a side view of a treatment tool for operation according to a 11th embodiment of the invention.
Figure 57A:
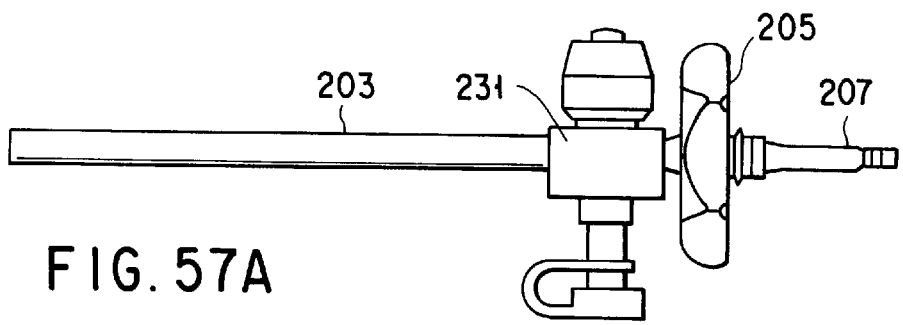
FIG. 57A is a side view of the sheath unit of the treatment tool for operation of FIG. 56.
Figure 57B:
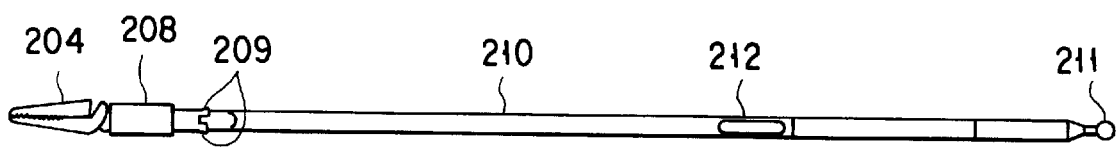
FIG. 57B is a side view of a treatment section operating unit.
Figure 57C:
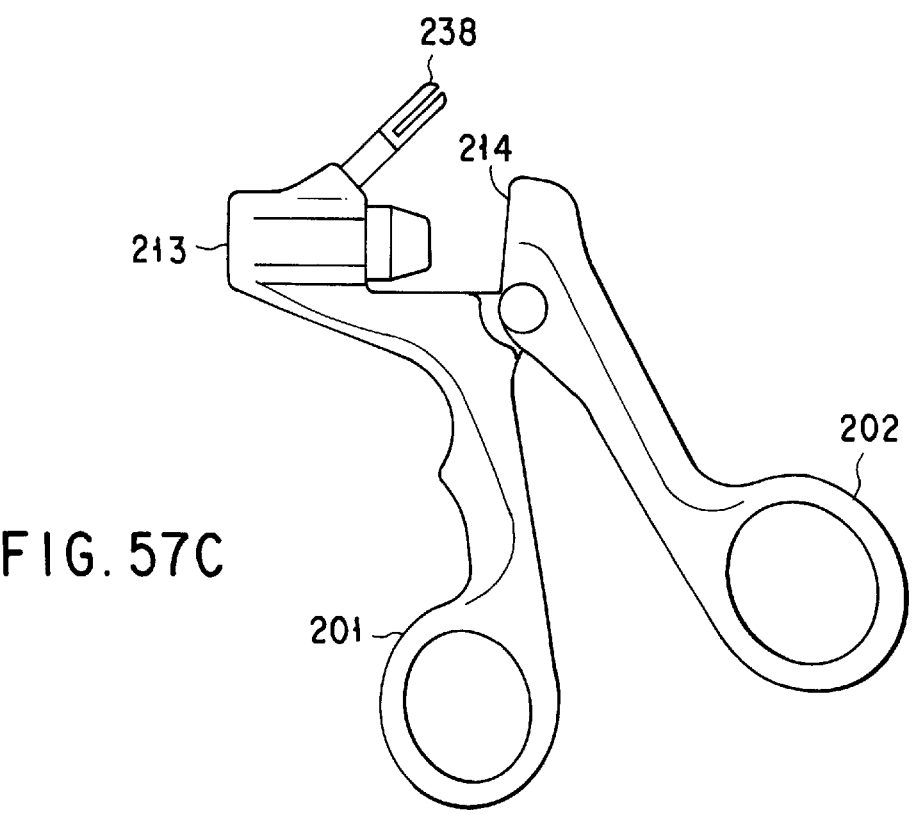
FIG. 57C is a side view of the operating section.
Figures 58A, 58B, 59:
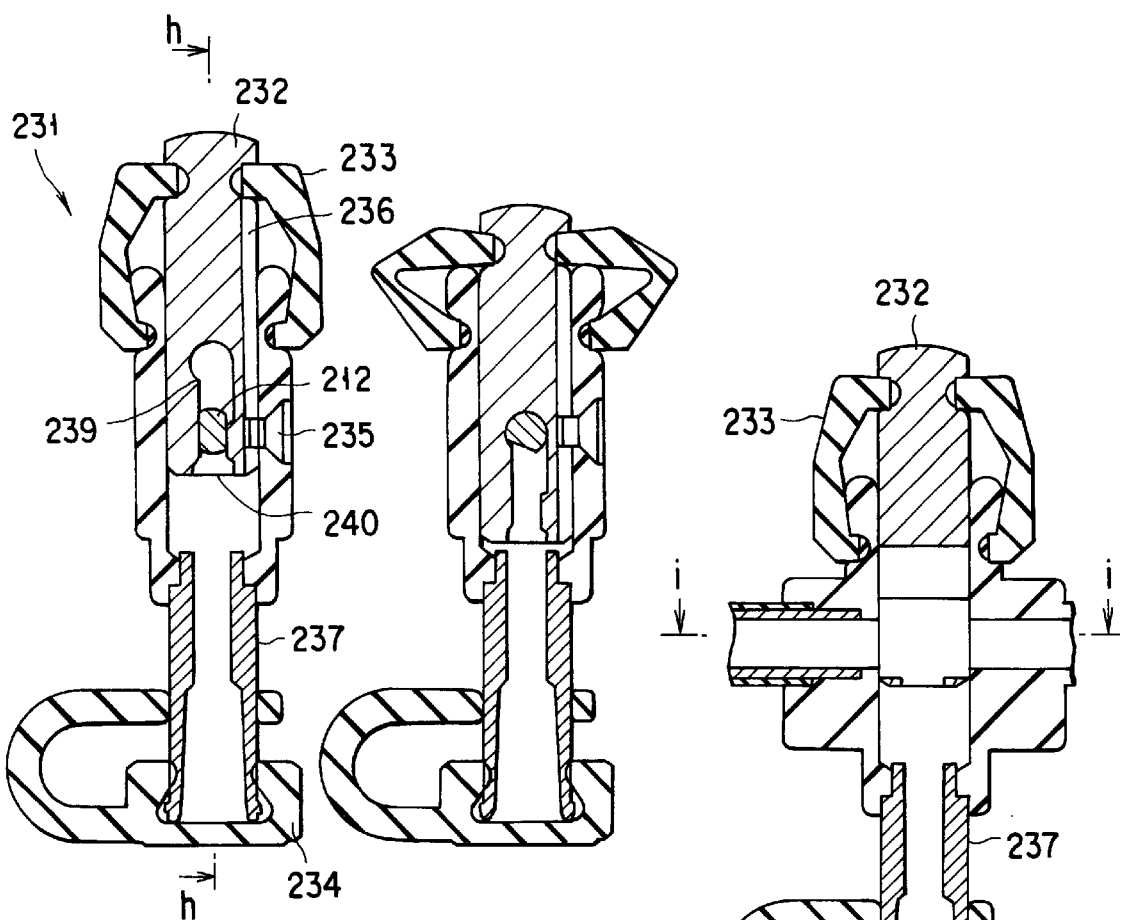
FIGS. 58A and 58B are sectional views of the operating section of the treatment tool for operation of FIG. 56.
FIG. 59 is a sectional view taken in line h—h in FIG. 58.
Figure 60:
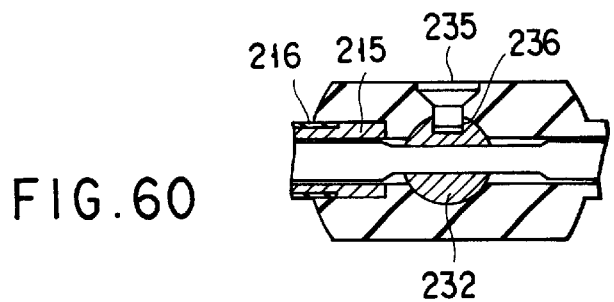
FIG. 60 is a sectional view taken in line i—i in FIG. 59.

As shown in FIG. 56, a button 232 is removably mounted on the operating section 231 of the sheath unit. FIG. 58A shows the state in which the button 232 engages the rotary engaging member 212 of the operating shaft 210 to restrict the rotation of the treatment section drive unit. FIG. 58B shows the state in which the restriction of rotation of the rotary engaging member 212 by the button 232 is relaxed. As shown, the button 232 is energized in combination with the rubber spring 233. Also, the button 232 has a positioning groove 236, and the operating section 231 has a positioning member 235. A washing port 237 and a rubber cap 234 are provided on the side opposite to the button 232. An opening 240 is formed on the washing port side of the button 232. The button 232 includes a shoulder 239 for rotating the rotary engaging member 212.

In this configuration, when the button 232 is pushed down, the button 232 ceases to interfere with the operating shaft 210. Upon release of the button 232, on the other hand, the biasing force of the rubber spring 233 causes the button 232 moves by being pushed out upward, and the rotary engaging member 212 and the treatment section drive unit are rotated by the shoulder 239. The relative positions of the button 232 and the rotary engaging member 212 are the same as those in the tenth embodiment The positioning member 235 and the positioning groove 236 fix the button 232 to the position where the operating shaft 210 can always be inserted. By supplying water from the washing port 237, the treatment tool as assembled can be washed to some degree. Also, the button 232 has an opening 240, through which the water supplied from the washing port 237 can enter the button 232.

As explained above, according to this embodiment, the operating section, the sheath unit and the treatment section drive unit can be easily disassembled and assembled with an improved washability and sterilization. Also, the treatment section drive unit can be fixed simply by operating the button 232 at the time of assemblage. Therefore, the assembling operation is simplified.

Figure 61:
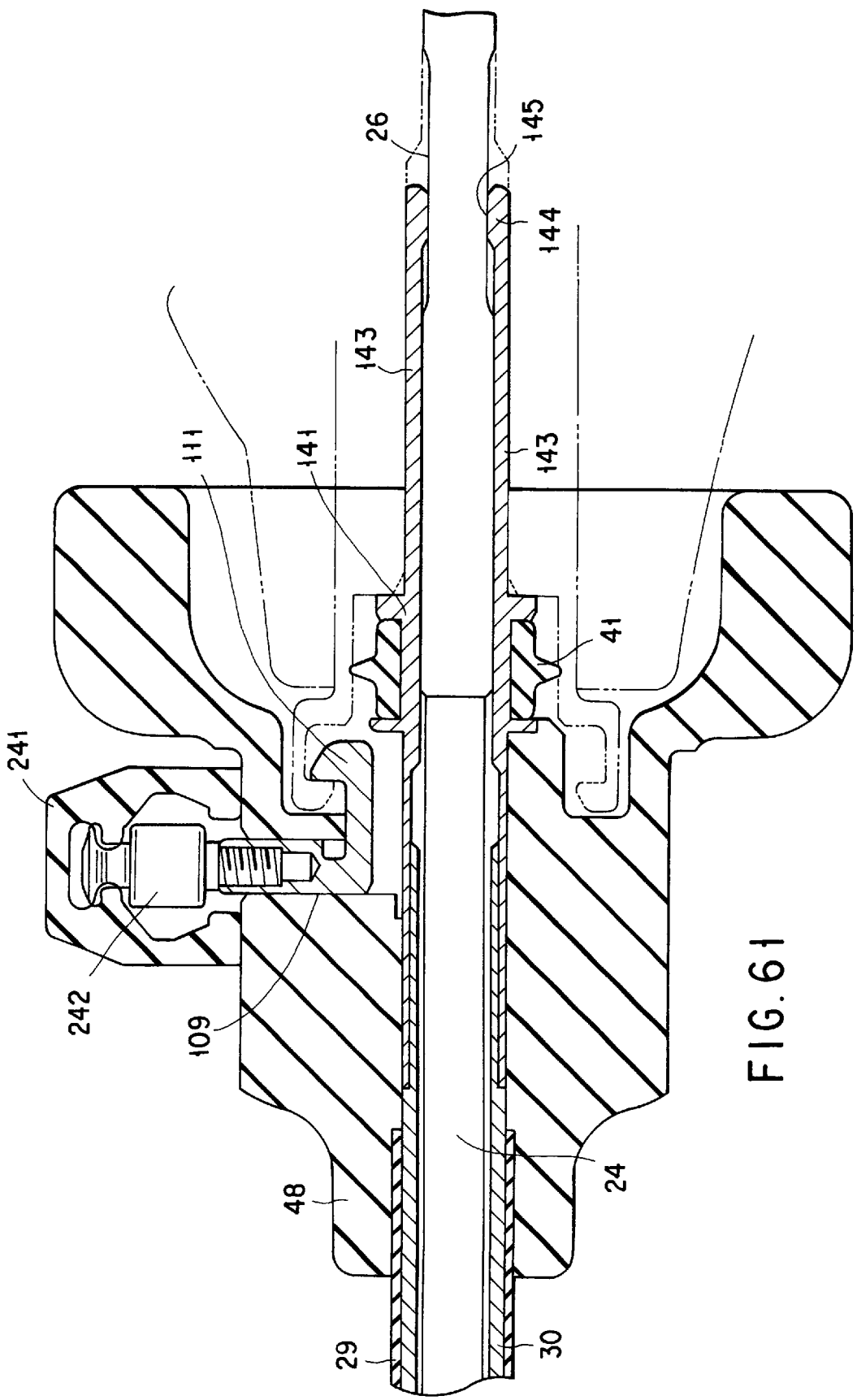
FIG. 61 is a side sectional view of a treatment tool for operation according to a 12th embodiment of the invention.
Figure 62:
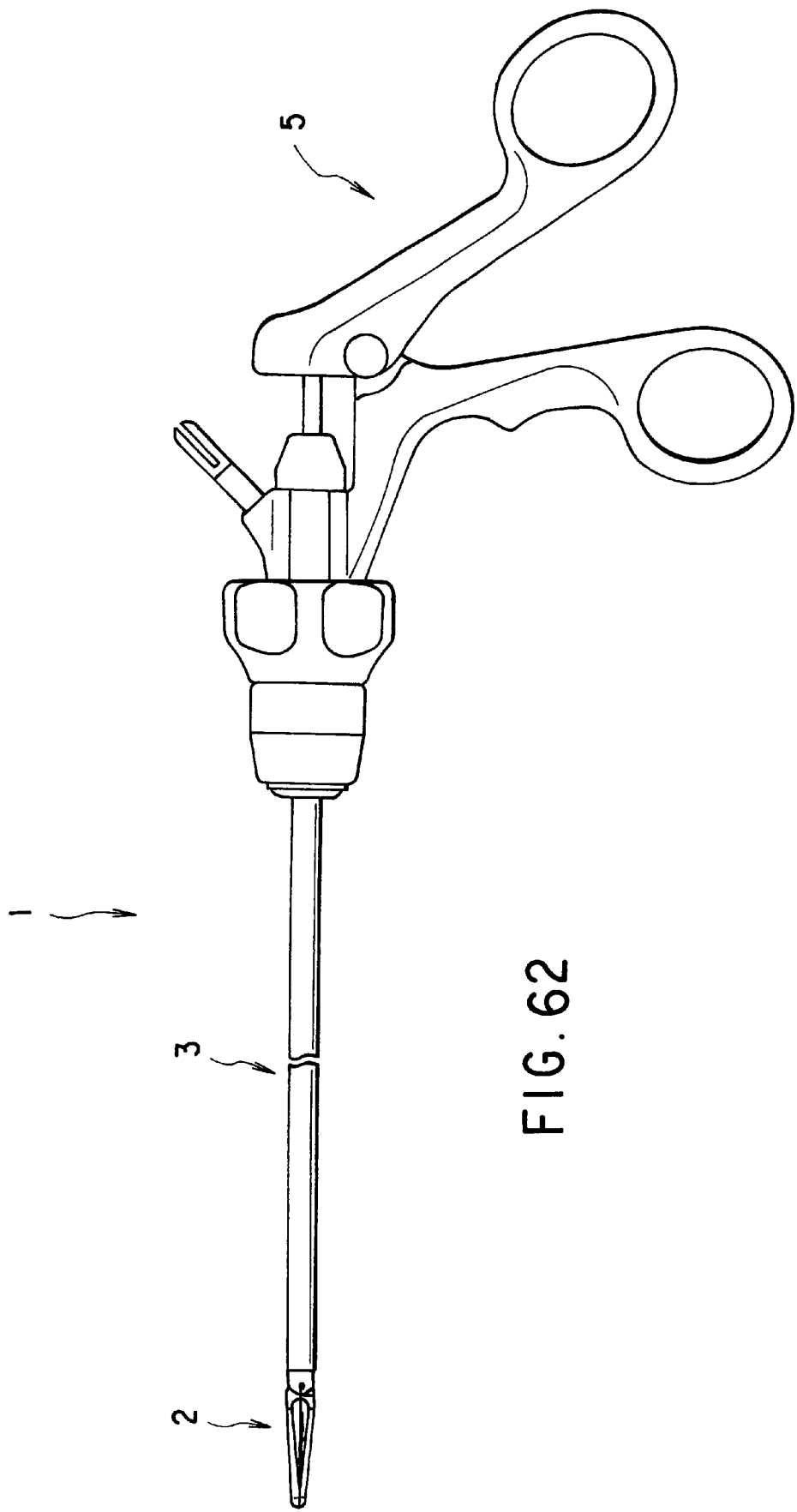
FIG. 62 is a side view of a treatment tool for operation according to a 13th embodiment of the invention.
Figure 67:
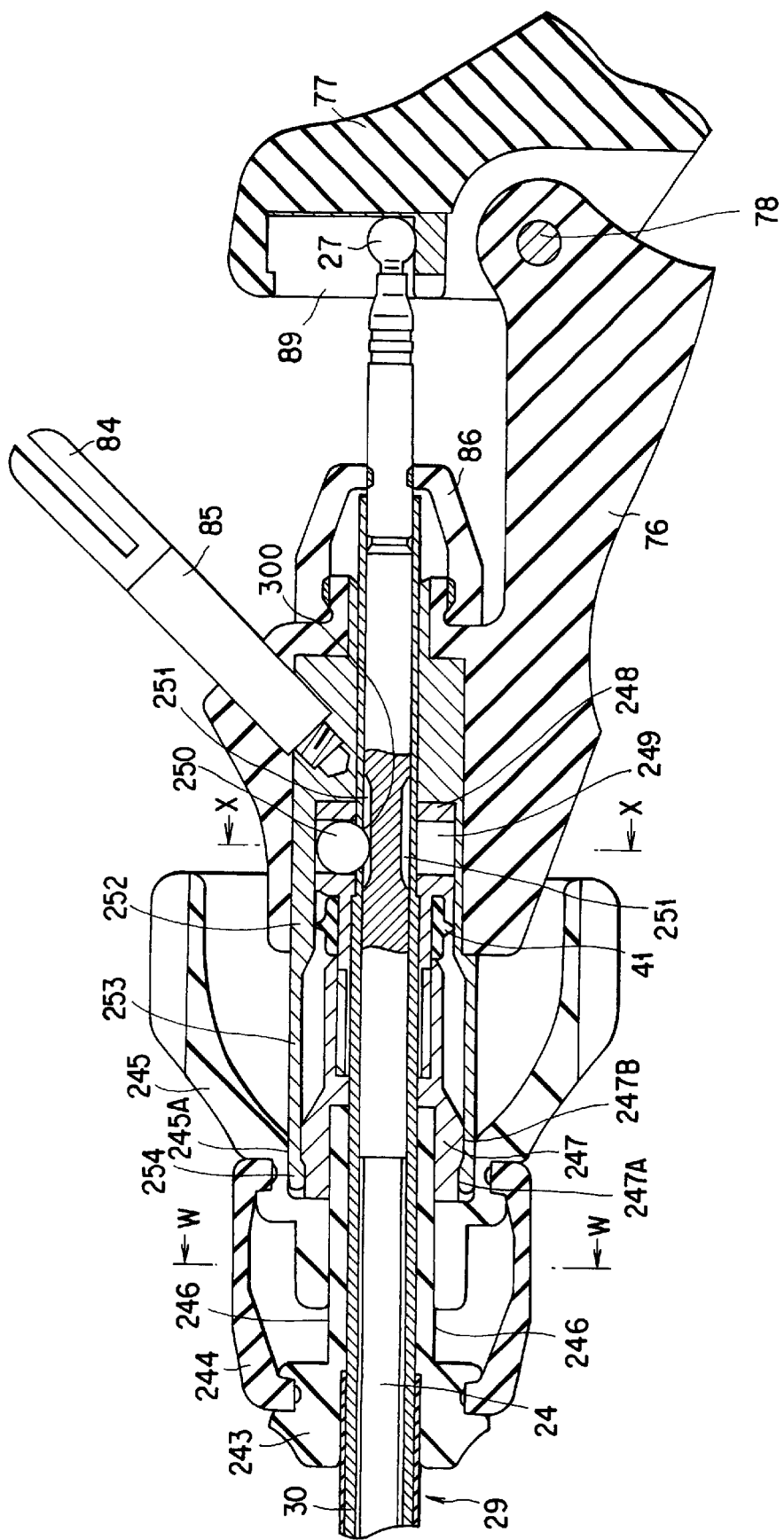
FIG. 67 is a sectional view of a coupler between the insertion section and the operating section.
Figure 68:
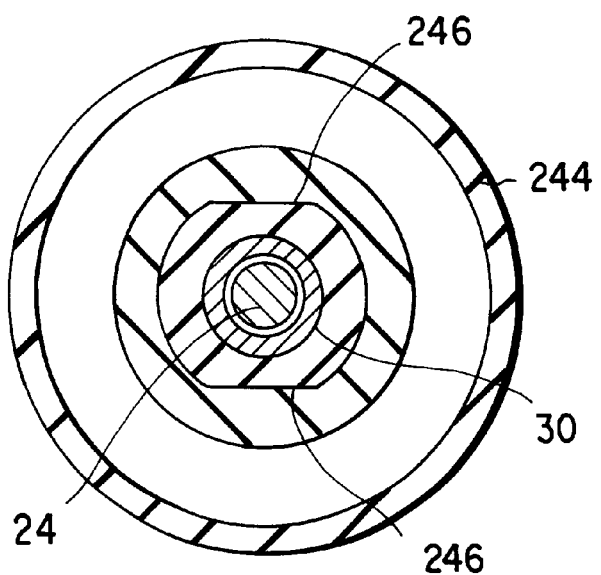
FIG. 68 is a sectional view taken in line W—W in FIG. 67.

FIG. 61 shows a 12th embodiment of the invention. This embodiment is a modification of the fourth embodiment shown in FIG. 29 and is different from the fourth embodiment only in the shape of the rubber spring 108. In the description that follows, therefore, the component parts shared with the fourth embodiment will be designated the same reference numerals as the corresponding component parts of the fourth embodiment and will not be described.

As shown, the rubber spring 241 according to this embodiment is made of an elastic material (ex. silicone rubber) having an electrically insulating characteristic, and removably engages the guide member 242 wholly covered thereby. The guide member 242 is fixed to the operating section engaging/disengaging member 111 through a screw.

The operating section engaging/disengaging member 111 according to the fourth embodiment is configured of a metal material to meet a high strength requirement. Also, a guide member 110 for connecting the operating section engaging/disengaging member 111 to the rubber spring 108 is desirably fixed on the operating section engaging/disengaging member 111 through a screw to secure a sufficient durability. Also, according to the fourth embodiment, the guide member 110 is partly exposed due to the shape of the rubber spring 108. Taking the treatment using a high-frequency current into consideration, therefore, the exposed part of the guide member 110 is required to be electrically insulated. A desirable material for electrically insulating the guide member 110 is a resin which is low in cost and easy to process. To secure a sufficient durability, it is not desirable to thread the resin and fix the engaging/disengaging member 242 along it.

With the configuration according to this embodiment, in contrast, the guide member 242 is fully covered by the rubber spring 241 having an electrically insulating characteristic, and therefore no problem as described above will not occur.

As described above, according to this embodiment, a similar effect to the fourth embodiment can be obtained. At the same time, since the guide member 242 is fully covered by the rubber spring 241 having an electrically insulating characteristic, the requirement is eliminated to mount an insulating resin on the guide member 242, thereby reducing the cost and improving the assembly characteristic.

FIGS. 62 to 72 show a 13th embodiment of the invention. This embodiment is a modification of the first embodiment, and has the same configuration as the first embodiment except for the means for restricting the rotation of the sheath 29 of the treatment section drive unit and the junction between the operating section 5 and the insertion section 3. Consequently, the component parts of this embodiment shared by the first embodiment will be designated by the same reference numerals as the corresponding parts of the first embodiment, respectively, and will not be described.

As shown in FIG. 64, the sheath body 243 is fixed at the base end of the sheath 29 of the insertion section 3. As shown in detail in FIG. 67, the sheath body 243 has two planes 246, 246 symmetric about the axis of the sheath body 243. A connector 247 connected to the operating section 5 is fixed at the base end of the sheath body 243. A butt member 248 is fixed at the base end of the connector 247. An annular packing 41 is integrated with the butt member 248. The forward end of the connector 247 is formed with a first cylindrical surface 247A and a second cylindrical surface 247B.

The butt member 248 is formed with a ball hole 249 for accommodating a ball 250. The inner diameter of an end of the ball hole 249 is set to the same value as the diameter of the ball 250. Also, the inner diameter of the other end of the ball hole 249 is set to a value smaller than the diameter of the ball 250 so that the ball 250 can be moved to a position free of the interference of the pipe 30 by the ball 250 and that the ball does not come off from the ball hole 249. The base end side of the pipe 30 is formed with a hole 300 at the position in opposed relation to the ball hole 249. This hole 300 has the inner diameter thereof set in such a manner that the ball 250 can move to the position where the ball 250 can settle within the range of the outer diameter of the butt member 248.

The plane section 246 of the sheath body 243 is covered with a rotary knob 245. This rotary knob 245 is unrotatably and axially slidably mounted on the plane section 246. Also, a rubber spring 244 is removably mounted between the forward end of the sheath body 243 and the rotary knob 245 for urging the rotary knob 245 toward the base end (operating section 5 side). A fixed hole 245A is formed in the inner depth of the rotary knob 245.

An insertion section connector 252 is fixed at the upper forward end of the fixed handle 76. A slotted snap fit arm 253 is arranged at the forward end of the insertion section connector 252. A protrusion 254 for engaging the cylindrical surface 247A of the connector 247 is formed inside of the forward end of the snap fit arm 253. The base end of the drive shaft 24 of the treatment section unit 2 is formed with two recesses 251, 251 having the same radius of curvature as the ball 250 and symmetric with each other about the center axis of the drive shaft 24.

By the way, the inner diameter of the snap fit arm 253 is set substantially equal to the outer diameter of the cylindrical surface 247 of the connector 247. Also, the outer diameter of the snap fit arm 253 is set substantially equal to the inner diameter of the fixed hole 245A of the rotary knob 245.

Next, an explanation will be given of the case in which a treatment tool for operation according to this embodiment is assembled.

Figure 69:
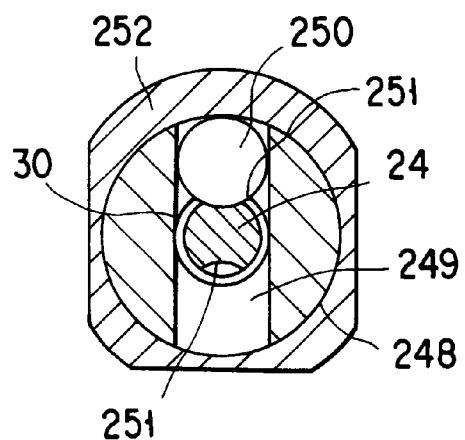
FIG. 69 is a sectional view taken in line X—X in FIG. 67.
Figure 70:
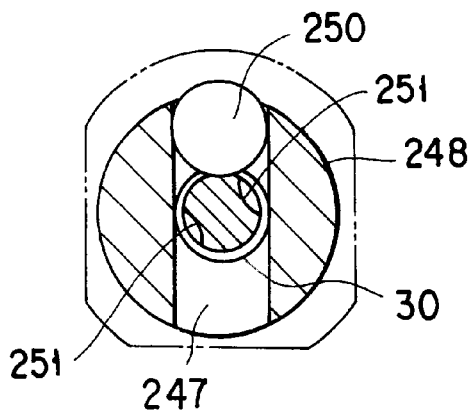
FIG. 70 is a sectional view taken in line X—X in FIG. 67 showing the state of the treatment section drive unit inserted in the insertion section with the operating section yet to be assembled.

The treatment section drive unit 2 and the sheath 29 are assembled the same way as in the fourth embodiment. In this case, with the passage of the base end of the drive shaft 24 through the neighborhood of the butt member 248 located at the base end of the sheath 29, the ball 250 moves outward as shown in FIG. 70. Under this condition, the rotation of the treatment section unit with respect to the sheath 29, as shown in FIG. 70, causes the ball 250 to drop into the recess 251 of the drive shaft 24 through the hole 300 of the pipe 30 and is settled within the range of the outer diameter of the butt member 248, as shown in FIG. 69. Under this condition, therefore, the insertion section connector 252 of the operating section 5 can be inserted into the treatment section unit 2.

Figure 71:
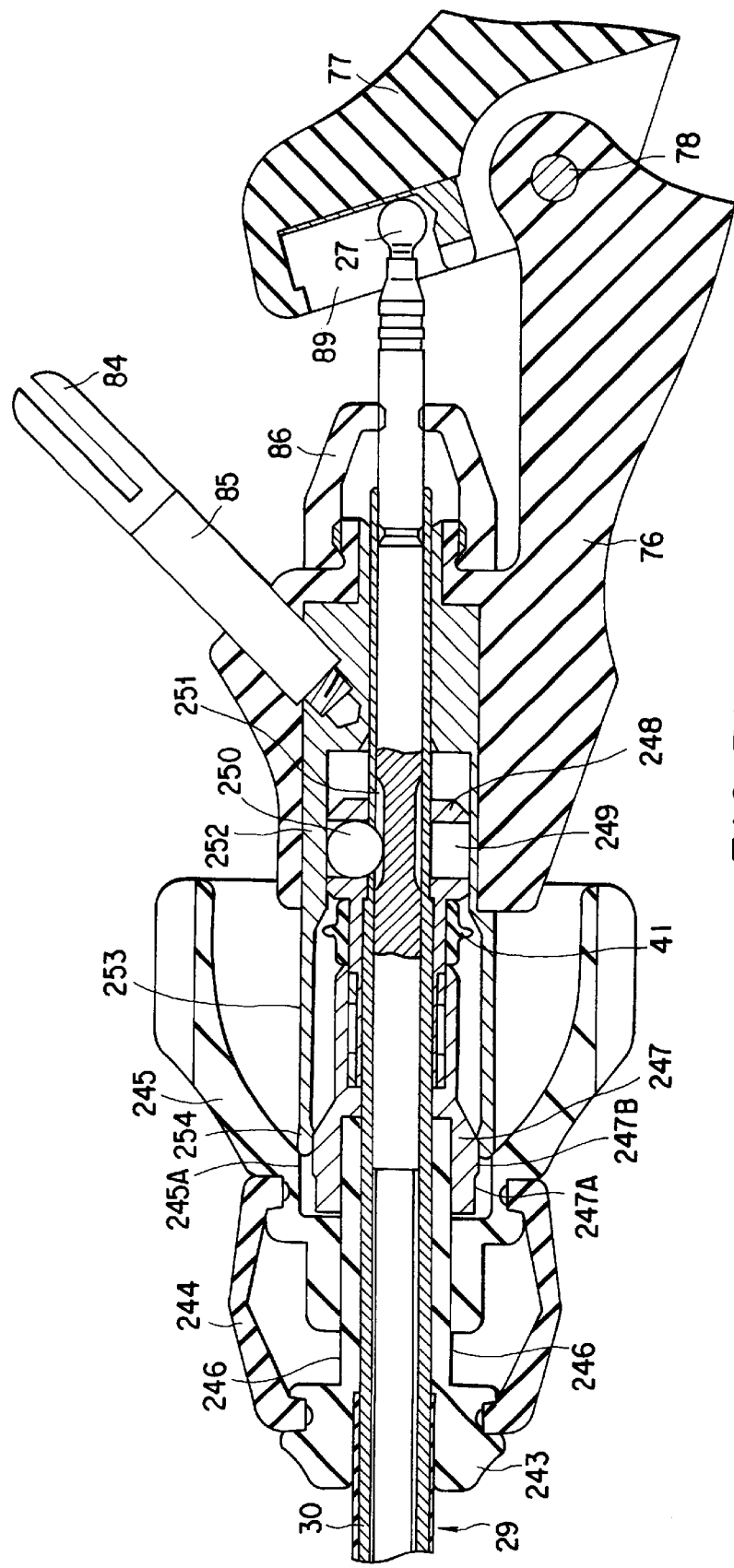
FIG. 71 is a side view of the coupler between the insertion section and the operating section during the post-assembly operation.

Then, the insertion section 3 on which the treatment section drive unit 2 is assembled is assembled on the operating section 5. The procedure for this operation is similar to that of the fourth embodiment. In this case, as shown in FIG. 71, the protrusion 254 at the forward end of the snap fit arm 253 overrides the cylindrical surface 247B of the connector 247, and therefore the snap fit arm 253 is elastically deformed outward. The snap fit arm 253 thus elastically deformed has an outer diameter larger than the inner diameter of the fixed hole 245A of the rotary knob 245. Therefore, the rotary knob 245 is forced out toward the forward end of the sheath 29 against the energizing force of the rubber spring 244. After the protrusion 254 overrides the cylindrical surface 245B, the outer diameter of the snap fit arm 253 is restored to the original size, and therefore the rotary knob 245 returns to the original position where it contacts the connector 247 by the biasing force of the rubber spring 244 (see FIG. 67).

Under this condition, even when the force toward the forward end of the sheath 29 is exerted, the snap fit arm 253 cannot be elastically deformed as the protrusion 254 engages the steps between the cylindrical surfaces 247A, 247B and fixedly fitted in the fixed hole 245A. Also, the rotary knob 245, which is fitted in the plane 246 of the sheath body 243, cannot rotate. Also, the ball 250 arranged at the base end of the sheath 29 is accommodated in the insertion section connector 252 and thus restricted from outward projection (see FIG. 69). Thus, the engagement between the ball 250 and the recess 251 prevents the rotation of the drive shaft 24 with respect to the pipe 30. Specifically, the treatment section drive unit 2 cannot rotate with respect to the insertion section 3. Consequently, with the rotation of the rotary knob 245, the treatment section drive unit 2 is rotated through the sheath body 243, the connector 247 and the butt member 248.

Now, the work of disassembling the treatment tool for operation according to this embodiment will be explained.

Figure 72:
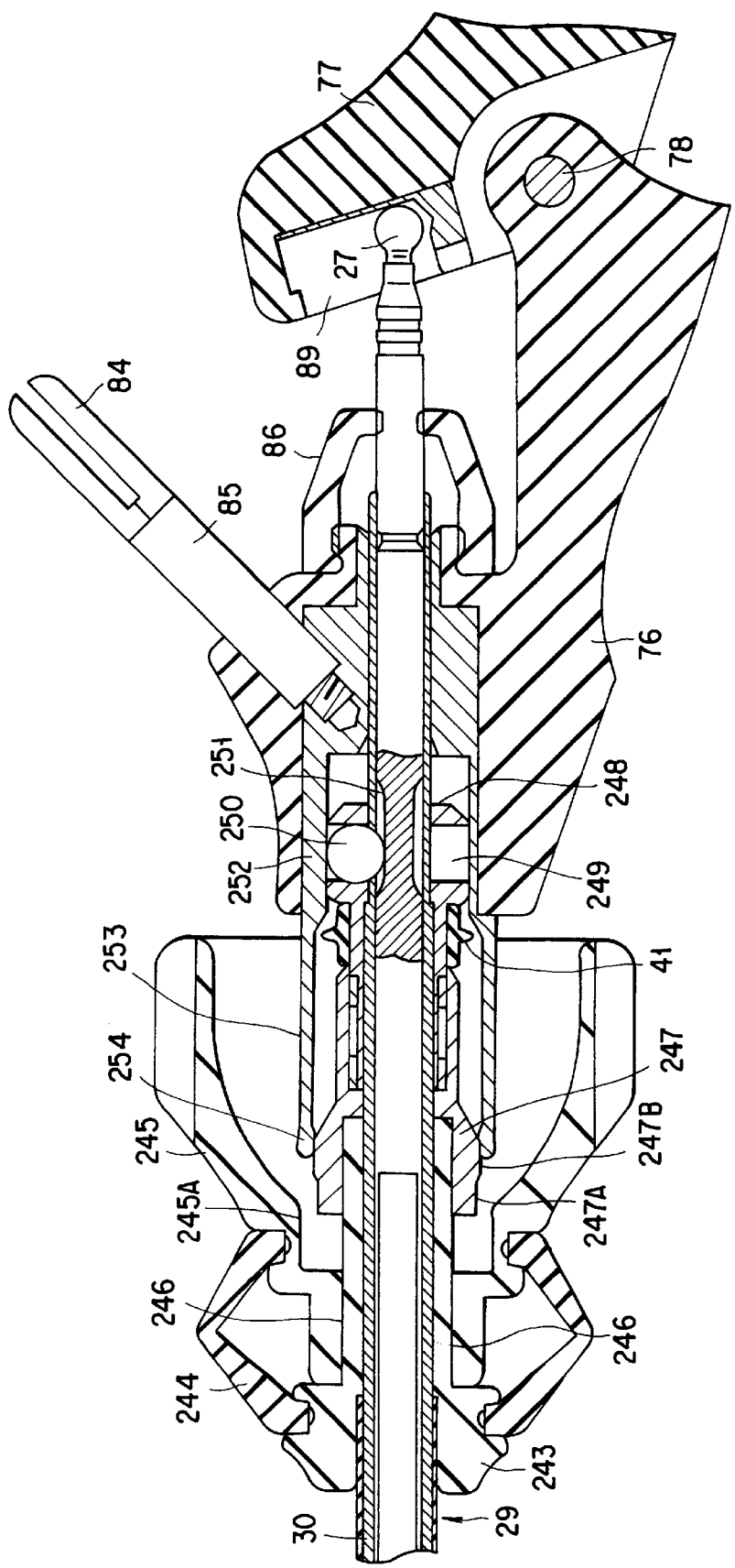
FIG. 72 is a sectional view showing the state in which the insertion section is removed from the operating section while pulling a rotary knob toward the forward end.

The order of disassembly is the same as in the fourth embodiment. Specifically, the first step is to pull the rotary knob 245 toward the forward end of the sheath 29 while opening the movable handle 77. When the rotary knob 245 is pulled forward, as shown in FIG. 72, it becomes possible for the snap fit arm 253 to be elastically deformed outward. By pulling the insertion section 3 toward the forward end with a force of not less than a predetermined magnitude, therefore, the insertion section 3 can be separated from the operating section 5. By the way, the insertion section 3 and the treatment drive unit 2 can be disassembled in the order reverse to the assembly work.

As described above, according to this embodiment, like in the third embodiment, the component elements can be disassembled and assembled easily within a short time. Also, the treatment tool for operation according to this embodiment has no parts difficult to wash and therefore is suitably used as a medical equipment meeting the requirement for a high degree of cleanliness. Also, since the treatment section drive unit 2 can be inserted in or removed from the insertion section 3 simply by moving the ball vertically, the disassembly and assembly work can be performed smoothly with only a small resistance. Further, the small number of parts required between the butt section of the operating section 5 and the insertion section 3 on the one hand and the engaging section of the operating section 5 and the insertion section 3 on the other hand, can minimize the play of the coupler between the insertion section 3 and the operating section 5 with the treatment section drive unit 2 assembled thereon without any assembly adjustment.

INDUSTRIAL APPLICABILITY

As described above, according to this invention, a treatment tool for operation requiring a high degree of cleanliness as a medical equipment is provided in which the component elements making up the treatment tool for operation can be easily disassembled or assembled within a short time.

What is claimed is:

1. A treatment tool for operation comprising:
   an insertion section inserted into a living body;
   an operating section connected removably to a base end of the insertion section, said operating section including a fixed handle and a movable handle which is openable and closable with respect to the fixed handle;
   a treatment section drive unit to which the insertion section is connectable, said treatment section drive unit including an operable treatment section arranged at a forward end of the insertion section, drive means for driving the treatment section, and a drive shaft for connecting the drive means to the operating section and transmitting an operating force from the operating section to the drive means for actuating the treatment section;
   an engaging/disengaging member which is arranged at the base end of the insertion section and which is engageable with a forward end of the operating section to enable connection between the insertion section and the operating section; and
   a biasing member which urges the engaging/disengaging member.

2. A treatment tool for operation according to claim 1, wherein said movable handle is rotatably mounted on said fixed handle.

3. A treatment tool for operation according to claim 1, further comprising a pressure section arranged in said insertion section for canceling an engaged state between said engaging/disengaging member and the forward end of the operating section.

4. A treatment tool for operation according to claim 3, wherein said biasing member is formed of an elastic material having an electrically insulating characteristic, and said pressure section is covered by said biasing member so as not to be exposed.

5. A treatment tool for operation according to claim 4, wherein said biasing member is made of silicone rubber.

6. A treatment tool for operation according to claim 1, further comprising a guide including a first sloped surface arranged at a forward end side of said operating section and a second sloped surface arranged at a forward end side of said engaging/disengaging member and having a shape substantially coinciding with said first sloped surface for guiding engagement between the forward end of said operating section and said engaging/disengaging member.

7. A treatment tool for operation according to claim 1, further comprising a connector for removably connecting said treatment section drive unit and said insertion section.

8. A treatment tool for operation according to claim 7, wherein said connector comprises:
   a protrusion formed at a forward end side of said treatment section drive unit;
   a first butt surface arranged at the forward end side of said treatment section drive unit;
   a substantially L-shaped engaging groove arranged at a forward end side of said insertion section and adapted to engage said protrusion;
   a second butt surface arranged at the forward end side of said insertion section and adapted to contact said first butt surface;
   an engaging surface arranged at a base end side of said drive shaft; and
   a rotary engaging member arranged at a base end side of said insertion section for engaging said engaging surface and restricting rotation of said drive shaft.

9. A treatment tool for operation according to claim 8, wherein:
   said rotary engaging member includes an elastic section adapted to be elastically deformed radially outward of the insertion section, and said fixed handle includes a housing for accommodating said elastic section, and
   radical outward deformation of said elastic section is restricted and an engaged state between said engaging surface and said rotary engaging member is held by accommodating said elastic section in said housing.

10. A treatment tool for operation according to claim 1, wherein an engaging section formed at a forward end of the fixed handle is arranged on a plane substantially perpendicular to a central axis of the insertion section and along a circumferential direction of the insertion section, thereby enabling the insertion section to rotate for 360 degrees with respect to the fixed handle.

11. A treatment tool for operation comprising:
    an insertion section inserted into a living body;
    an operating section connected removably to a base end of the insertion section, said operating section including a fixed handle and a movable handle which is openable and closable with respect to the fixed handle;
    a treatment section drive unit to which the insertion section is connectable, said treatment section drive unit including an operable treatment section arranged at a forward end of the insertion section, drive means for driving the treatment section, and a drive shaft for connecting the drive means to the operating section and transmitting an operating force from the operating section to the drive means for actuating the treatment section; and
    an engaging/disengaging unit arranged at the base end of the insertion section for connecting/disconnecting the insertion section with reference to the operating section, said engaging/disengaging unit including an engaging/disengaging member which is engageable with a forward end of the operating section and which is detachable and attachable with reference to the insertion section, and biasing means for urging the engaging/disengaging member in an engagement direction in which the engaging/disengaging member is brought into engagement with the forward end of the operating section;
    wherein said engaging/disengaging member is adapted to be disengaged from the operating section by pushing the engaging/disengaging unit in a direction opposite to said engagement direction.

* * * * *